(12) United States Patent
Hanai et al.

(10) Patent No.: US 7,651,688 B2
(45) Date of Patent: *Jan. 26, 2010

(54) METHOD OF MODULATING THE ACTIVITY OF FUNCTIONAL IMMUNE MOLECULES TO CD52

(75) Inventors: Nobuo Hanai, Machida (JP); Kazuyasu Nakamura, Machida (JP); Emi Hosaka, Machida (JP); Motoo Yamasaki, Machida (JP); Kazuhisa Uchida, Machida (JP); Toyohide Shinkawa, Machida (JP); Susumu Imabeppu, Ube (JP); Yutaka Kanda, Machida (JP); Naoko Yamane, Machida (JP); Hideharu Anazawa, Tokyo (JP)

(73) Assignee: Kyowa Hakko Kirin Co., Ltd, Tokyo (JP)

( * ) Notice: Subject to any disclaimer, the term of this patent is extended or adjusted under 35 U.S.C. 154(b) by 59 days.

This patent is subject to a terminal disclaimer.

(21) Appl. No.: 11/686,915

(22) Filed: Mar. 15, 2007

(65) Prior Publication Data

US 2007/0166304 A1    Jul. 19, 2007

Related U.S. Application Data

(62) Division of application No. 11/126,176, filed on May 11, 2005, now Pat. No. 7,214,775, which is a division of application No. 09/958,307, filed as application No. PCT/JP00/02260 on Apr. 7, 2000, now abandoned.

(30) Foreign Application Priority Data

Apr. 9, 1999  (JP)  .............................. P. 11-103158

(51) Int. Cl.
*A61K 39/00* (2006.01)
*A61K 39/395* (2006.01)
(52) U.S. Cl. ................. 424/133.1; 424/138.1
(58) Field of Classification Search ........... None
See application file for complete search history.

(56) References Cited

U.S. PATENT DOCUMENTS

| | | | |
|---|---|---|---|
| 4,350,683 A | 9/1982 | Galfre |
| 4,721,777 A | 1/1988 | Uemura |
| 4,757,018 A | 7/1988 | Brown |
| 4,816,567 A | 3/1989 | Cabilly |
| 4,849,509 A | 7/1989 | Thurin |
| 5,272,070 A | 12/1993 | Lehrman |
| 5,453,363 A | 9/1995 | Rudolph |
| 5,464,764 A | 11/1995 | Capecchi |
| 5,614,385 A | 3/1997 | Oppermann |
| 5,658,789 A | 8/1997 | Quaranta |
| 5,665,569 A | 9/1997 | Ohno |
| 5,672,502 A | 9/1997 | Birch |
| 5,728,568 A | 3/1998 | Sullivan |
| 5,830,470 A | 11/1998 | Nakamura |
| 5,858,983 A | 1/1999 | Seed et al. |
| 5,880,268 A | 3/1999 | Gallatin |
| 5,891,996 A | 4/1999 | Mateo |
| 5,922,845 A | 7/1999 | Deo |
| 5,932,703 A | 8/1999 | Godiska |
| 5,935,821 A | 8/1999 | Chatterjee |
| 5,977,316 A | 11/1999 | Chatterjee |
| 6,018,032 A | 1/2000 | Koike |
| 6,054,304 A | 4/2000 | Taniguchi et al. |
| 6,129,913 A | 10/2000 | Ames |
| 6,150,132 A | 11/2000 | Wells |
| 6,169,070 B1 | 1/2001 | Chen |
| 6,238,894 B1 | 5/2001 | Taylor |
| 6,245,332 B1 | 6/2001 | Butcher |
| 6,291,219 B1 | 9/2001 | Taniguchi |
| 6,350,868 B1 | 2/2002 | Weston |
| 6,437,098 B1 | 8/2002 | Shitara |
| 6,455,043 B1 | 9/2002 | Grillo-Lopez |
| 6,488,930 B1 | 12/2002 | Wu |
| 6,498,015 B1 | 12/2002 | Godiska |
| 6,602,684 B1 | 8/2003 | Umana et al. |
| 6,737,056 B1 | 5/2004 | Presta |
| 6,762,174 B1 | 7/2004 | Taub |
| 6,946,292 B2 | 9/2005 | Kanda et al. |
| 6,986,890 B1 | 1/2006 | Shitara |
| 6,989,145 B2 | 1/2006 | Shitara |
| 7,033,589 B1 | 4/2006 | Reff et al. |
| 7,138,117 B1 | 11/2006 | Wu |
| 7,214,775 B2 * | 5/2007 | Hanai et al. .............. 530/387.1 |
| 7,297,775 B2 | 11/2007 | Idusogie |
| 2002/0019341 A1 | 2/2002 | Butcher |
| 2002/0098527 A1 | 7/2002 | Shitara |
| 2002/0160015 A1 | 10/2002 | Wells |
| 2002/0187930 A1 | 12/2002 | Wells |
| 2003/0115614 A1 | 6/2003 | Kanda |
| 2003/0157108 A1 | 8/2003 | Presta |
| 2003/0158389 A1 | 8/2003 | Idusogie |
| 2003/0170813 A1 | 9/2003 | Suga |
| 2003/0175273 A1 | 9/2003 | Shitara |

(Continued)

FOREIGN PATENT DOCUMENTS

CA    2424602    4/2002

(Continued)

OTHER PUBLICATIONS

Hale (J of Biological Regulators and Homeostatic Agents, 2001, 15:386-391).*

(Continued)

*Primary Examiner*—Laura B Goddard
(74) *Attorney, Agent, or Firm*—Sughrue Mion, PLLC

(57) ABSTRACT

The invention relates to a method for controlling the activity of an immunologically functional molecule, such as an antibody, a protein, a peptide or the like, an agent of promoting the activity of an immunologically functional molecule, and an immunologically functional molecule having the promoted activity.

3 Claims, 12 Drawing Sheets

U.S. PATENT DOCUMENTS

| | | |
|---|---|---|
| 2003/0190316 A1 | 10/2003 | Kakuta |
| 2004/0002077 A1 | 1/2004 | Taira |
| 2004/0072290 A1 | 4/2004 | Umana et al. |
| 2004/0093621 A1 | 5/2004 | Shitara |
| 2004/0110282 A1 | 6/2004 | Kanda |
| 2004/0110704 A1 | 6/2004 | Yamane |
| 2004/0132140 A1 | 7/2004 | Satoh |
| 2005/0048647 A1 | 3/2005 | Taira |
| 2005/0074843 A1 | 4/2005 | Umana |
| 2005/0160485 A1 | 7/2005 | Taniguchi |
| 2005/0187380 A1 | 8/2005 | Shitara |
| 2005/0216958 A1 | 9/2005 | Yamane |
| 2005/0226867 A1 | 10/2005 | Iida et al. |
| 2005/0262593 A1 | 11/2005 | Kanda et al. |
| 2005/0272916 A1 | 12/2005 | Hanai et al. |
| 2005/0276805 A1 | 12/2005 | Hanai et al. |
| 2005/0287138 A1 | 12/2005 | Iida et al. |
| 2006/0024800 A1 | 2/2006 | Hanai et al. |
| 2006/0063254 A1 | 3/2006 | Kanda et al. |
| 2006/0064781 A1 | 3/2006 | Kanda et al. |
| 2006/0078990 A1 | 4/2006 | Kanda et al. |
| 2006/0078991 A1 | 4/2006 | Kanda et al. |
| 2006/0223147 A1 | 10/2006 | Nishiya |
| 2007/0010009 A1 | 1/2007 | Kanda et al. |
| 2007/0111281 A1 | 5/2007 | Sondermann |
| 2007/0166300 A1 | 7/2007 | Hanai |
| 2007/0166301 A1 | 7/2007 | Hanai |
| 2007/0166302 A1 | 7/2007 | Hanai |
| 2007/0166303 A1 | 7/2007 | Hanai |
| 2007/0166304 A1 | 7/2007 | Hanai |
| 2007/0166305 A1 | 7/2007 | Hanai |
| 2008/0261301 A1 | 10/2008 | Kanda |

FOREIGN PATENT DOCUMENTS

| | | |
|---|---|---|
| EP | 0481791 | 4/1992 |
| EP | 623352 | 11/1994 |
| EP | 0625574 | 11/1994 |
| EP | 0811691 | 12/1997 |
| EP | 0816503 | 1/1998 |
| EP | 882794 | 9/1998 |
| EP | 0292965 | 11/1998 |
| EP | 1092037 | 4/2001 |
| EP | 1109570 | 6/2001 |
| EP | 1 176 195 A1 | 1/2002 |
| EP | 1174148 | 1/2002 |
| EP | 1254666 | 11/2002 |
| EP | 1266663 | 12/2002 |
| EP | 1314437 | 5/2003 |
| EP | 1331266 | 7/2003 |
| EP | 1443961 | 8/2004 |
| EP | 1498485 | 1/2005 |
| EP | 1498490 | 1/2005 |
| EP | 1498491 | 1/2005 |
| EP | 1500698 | 1/2005 |
| EP | 1676910 | 7/2006 |
| EP | 1705251 | 6/2009 |
| FR | 2708467 | 2/1995 |
| JP | 62194459 | 8/1987 |
| JP | 62244441 | 10/1987 |
| JP | 6189781 | 7/1994 |
| JP | 7502497 | 3/1995 |
| JP | 9500894 | 1/1997 |
| JP | 9049836 | 2/1997 |
| JP | 10257893 | 9/1998 |
| JP | 11127890 | 5/1999 |
| JP | 2002539079 | 11/2002 |
| JP | 2002544173 | 12/2002 |
| JP | 2003350165 | 10/2003 |
| JP | 2005058111 | 3/2005 |
| WO | 86005807 | 10/1986 |
| WO | 86005817 | 10/1986 |
| WO | WO 91/19501 | 12/1991 |
| WO | 93008837 | 5/1993 |
| WO | 93022335 | 11/1993 |
| WO | 94000136 | 1/1994 |
| WO | 94002616 | 2/1994 |
| WO | WO 94/16094 | 7/1994 |
| WO | 94022478 | 10/1994 |
| WO | 95003826 | 2/1995 |
| WO | 95024494 | 9/1995 |
| WO | 96007429 | 3/1996 |
| WO | 96023068 | 8/1996 |
| WO | 96026268 | 8/1996 |
| WO | 97010354 | 3/1997 |
| WO | 97/27303 | 7/1997 |
| WO | 97/30087 | 8/1997 |
| WO | 97033978 | 9/1997 |
| WO | 97/37683 | 10/1997 |
| WO | 98/54964 | 12/1998 |
| WO | 99015666 | 4/1999 |
| WO | 99025380 | 5/1999 |
| WO | 99037329 | 7/1999 |
| WO | 99/54342 | 10/1999 |
| WO | WO 99/54342 | 10/1999 |
| WO | 99/64618 | 12/1999 |
| WO | 00000219 | 1/2000 |
| WO | 00012113 | 3/2000 |
| WO | 00034490 | 6/2000 |
| WO | 00041724 | 7/2000 |
| WO | 00042074 | 7/2000 |
| WO | 00049153 | 8/2000 |
| WO | 00/61739 | 10/2000 |
| WO | 00059547 | 10/2000 |
| WO | 00062790 | 10/2000 |
| WO | 0064262 | 11/2000 |
| WO | 00066160 | 11/2000 |
| WO | 00067791 | 11/2000 |
| WO | 00067795 | 11/2000 |
| WO | 00073481 | 12/2000 |
| WO | 01060405 | 8/2001 |
| WO | 01064754 | 9/2001 |
| WO | 01077181 | 10/2001 |
| WO | 02002793 | 1/2002 |
| WO | 02010743 | 2/2002 |
| WO | 02012347 | 2/2002 |
| WO | 02031140 | 4/2002 |
| WO | 02046186 | 6/2002 |
| WO | 03018635 | 3/2003 |
| WO | WO 03/035835 | 5/2003 |
| WO | 03046186 | 6/2003 |
| WO | 03055993 | 7/2003 |
| WO | 03063767 | 8/2003 |
| WO | 03085089 | 10/2003 |
| WO | 03085107 | 10/2003 |
| WO | 03085118 | 10/2003 |
| WO | 06020114 | 2/2006 |

OTHER PUBLICATIONS

Hale et al (J Immunol Methods, 1987, 103:59-67).*
Rothman et al (Molecular Immunology, 1989, 26:1113-1123, IDS).*
Trubion Pharmaceuticals poster (Apr. 2008).*
Shitara et al (J Immunological Methods, 1994, 167:271-278, IDS).*
Shinkawa et al (J Biological Chemistry, 2003, 278:3466-3473, IDS).*
Genentech (Products- product information- facts about Rituxan), p. 1-3.*
Umana et al (Nature Biotechnology, Feb. 1999, 17:176-180).*
Rothman, R.J., et al., Molecular Immunology, vol. 26, No. 12, pp. 1113-1123 (1989) " Antibody—Dependent Cytotoxicity Mediated By Natural Killer Cells Is Enhanced by Castanospermine—Induced Alterations of IgG Glycosylation".
U.S. Appl. No. 09/958,307, filed Oct. 2001, Kanda et al.

Furukawa et al Protein, Nucleic Acid and Enzyme, 43, 2309-2317 (1998).
Maly et al, Cell, vol. 86, 643-653, Aug. 23, 1996.
Wright et al. Tibtech, 15, 26-32 (1997).
Breton et al, Glycobiology, 8, No. 1, 87-94 (1998).
Asano et al, The EMBO Journal, vol. 16, No. 8, pp. 1850-1857 (1997).
Shitara et al. Journal of Immunological Methods, 167, 271-278 (1994).
Oriol et al. Glycobiology, 9, No. 4, 323-334 (1999).
Raju, et al. (2000) Glycobiology, 10(5): 477-86.
Stryer (1988) Biochemistry, 3rd Ed., Freeman and Co., New York, NY, pp. 35-37.
Shinkawa, et al. (2003) J. Biol. Chem., 278(5): 3466-73.
Jones, et al. (2001) Pharmacogenomics J., 1(2): 126-34.
Lifely, et al. (1995) Glycobiology, 5(8): 813-22.
U.S. Appl. No. 60/337,642, filed Oct. 2001, Presta.
U.S. Appl. No. 60/347,694, filed Jan. 2002, Presta.
U.S. Appl. No. 60/082,581, filed Apr. 1998, Umana et al.
Wilson et al, "Structural analysis of N-glycans from allergenic grass, ragweed and tree pollens: Core 1,3-linked fucose and xylose present in all pollens examined", Glycoconjugate Journal 15(11):1055-1070 (1998).
Boyd et al, Molecular Immunology, 1995, vol. 32, No. 17/18, pp. 1311-1318.
Clark, Chem. Immunol. 1997, vol. 65, pp. 88-110.
Ohyama et al, The Journal of Biological Chemistry, 1998, vol. 273, No. 23, pp. 14582-14587.
Sullivan et al, The Journal of Biological Chemistry, 1998, vol. 273, No. 14, pp. 8193-8202.
Ripka et al, Archives of Biochemistry and Biophysics, 1986, vol. 249, No. 2, pp. 533-545.
Ripka et al, Somatic Cell and Molecular Genetics, 1986, vol. 12, No. 1 pp. 51-62.
Shields et al, The Journal of Biological Chemistry, 2002, vol. 277, No. 30, pp. 26733-26740.
Jefferies et al (BioChem J. 268 :529-537 (1990).
Routier et al (Glycoconjugate Journal 14 :201-207 (1997)).
Potelligent™Technology, BioWa, Inc, internet address: biowa.com/news/pdf/Bio2003%20&%20Anti-Cancer%20BioWa%20Non%20Confidential.pdf#search=%22Potelligent%20Technology%20BioWa%2C%20Inc.%20pdf%22, Jul. 21, 2004.
Yamane-Ohnuki et al, Biotechnology & Bioengineering, vol. 87, No. 5, Sep. 5, 2004.
Rituxan product insert, 2 pages, © 2004 IDEC Pharmaceuticals Corporation and Genentech Inc.
Nose, J Immunology (1990) vol. 145, No. 3, 910-914.
Shinkawa et al, *The Journal of Biological Chemistry*, 278, 3466-3473 (2003).
U.S. Appl. No. 60/337,642, filed Oct. 2001, Presta.
U.S. Appl. No. 60/347,694, filed Jan. 2002, Presta.
U.S. Appl. No. 60/082,581, filed Apr. 1998, Umana et al.
Ohyama et al, The Journal of Biological Chemistry, 1998, vol. 273, No. 23, pp. 14582-14587.
Sullivan et al, The Journal of Biological Chemistry, 1998, vol. 273, No. 14, pp. 8193-8202.
Ripka et al, Archives of Biochemistry and Biophysics, 1986, vol. 249, No. 2, pp. 533-545.
Ripka et al, Somatic Cell and Molecular Genetics, 1986, vol. 12, No. 1 pp. 51-62.
Shields et al, The Journal of Biological Chemistry, 2002, vol. 277, No. 30, pp. 26733-26740.
Routier et al (Glycoconjugate Journal 14:201-207 (1997).
Shitara et al, "A new vector for the high level expression of chimeric antibodies in myeloma cells", Journal of Immunological Methods 167(1-2):271-278 (1994).
Wilson et al, "Structural analysis of N-glycans from allergenic grass, ragweed and tree pollens: Core ∀ 1, 3-linked fucose and xylose present in all pollens examined", Glycoconjugate Journal 15(11):1055-1070 (1998).
Lifely et al, Glycobiology, 1995, vol. 5, No. 8, pp. 813-822.
Boyd et al, Molecular Immunology, 1995, vol. 32, No. 17/18, pp. 1311-1318.
Clark, Chem. Immunol. 1997, vol. 65, pp. 88-110.
Shinkawa et al, The Journal of Biological Chemistry, 2003, vol. 278, No. 5, pp. 3466-3473.
Jefferis et al (Biochem J. 268:529-537 (1990)).
Jensen et al (Ann Hematol, 1998, 77:89-91).
Genentech (Products—product Information—Facts About RITUXAN, p. 1-3, printed May 2, 2006.
Reff et al (Blood, 1994, 83:435-445).
U.S. Appl. No. 60/572,899, filed May 2004, Mitsuo Satoh.
Abbas et al., Cellular and Molecular Immunology, 2$^{nd}$ Ed., by WB Saunders Co., Philidelphia, PA, p. 219 (1994).
Alabyev et al., Developmental & Comparative Immunology, 24:765-770 (2000).
Anders et al., Exp. Nephrol., 8:181-193 (2000).
Andrew et al., J. Immunol., 166(1):103-111 (2001).
Atkinson et al., Canadian J. of Biochem. and Cell Biology, 62(12):1343-1350 (1984).
Awwad et al., Cancer Immunological Immunother., 38:23-30 (1994).
Bartunkova et al., APMIS, 108(6):409-416 (2000).
Becker et al., Biochemica et Biophysica Acta., 1455:193-204 (1999).
Bei et al., J. of Immunological Methods, 182(2):245-255 (1995).
Bendig, Methods: A Companion to Methods in Enzymology, 8:83-93 (1995).
Berg et al., Biotechniques, 14(6):972-978 (1993).
Bibila et al., Biotechnol. Prog., 10(1):87-96 (1994).
Bishop, Reprod. Nutr. Dev., 36:607-618 (1998).
Biswas et al., Cancer Research, 66(13):6816-6825 (2006).
Blumenthal et al., American J. of Pathology, 156(5):1581-1588 (2000).
Blumenthal et al., "Unique Molecular Markers in Human Endometriosis: Implications for Diagnosis and Therapy", Expert Reviews in Molecular Medicine, pp. 1-12 (Nov. 2001).
Bonecchi et al., J. Exp. Med., 87(1):129-134 (1998).
Bonin et al., PNAS, 94:2085-2090 (1997).
Brady et al., Curr. Top. Microbiol. Immunol., 2005:1-18(1996).
Brams et al., Int. Immunopharmacol., 1:277-294 (2001).
Brekke et al., Mol. Immunol., 30:1419-1425 (1993).
Brinkman-Van Der Linden et al., J. of Biological Chemistry, 271(24):14492-14495 (1996).
Broad et al., Cytotechnology, 5:47-55 (1991).
Brown et al., Proc. Natl. Acad. Sci., USA, 88(7):2663-2667 (1991).
Burgess et al., J. of Cell Bio., 111:2129-2138 (1990).
Byrd et al., J. of Biological Chemistry, 257(24):14657-14666 (1982).
Cambi et al., Cellular Microbiology, 7(4):481-488 (2005).
Cameron, Mol. Biotech, 7:253-265 (1997).
Canadian Office Action dated Jul. 31, 2007 (Ca 2,424,602).
Capecchi et al., Scientific American, 270:34-41 (1994).
Cartoon et al., Blood, 99(3):754-758 (2002).
Caspi et al., J. of Biological Chemistry, 278(40):38740-38748 (2003).
Castro et al., Research School of Biosciences, United Kingdom., 19:27-36 (1995).
Chantry et al., Current Drug Targets- Inflammation & Allergy, 1:109-116 (2002).
Chen et al., Journal of Pharmaceutical Sciences, 83(12):1657-1661 (1994).
Christensen et al., Glycobiology, 10(9):931-939 (2000).
Chuntharapai et al., Meth. Enzymol., 288:15-27 (1997).
Clarke et al., Glycobiology, 9(2):191-202 (1999).
Clemetson et al., Blood, 96(13):4046-4054 (2000).
Co et al., Proc. Natl. Acad. Sci, 88(7):2869-2873 (1991).
Co et al., Cancer Res., 56:1118-1125 (1996).
Cooper et al., Eur. J. lmmunol. 33:666-675 (2003).
Cragg et al., Blood, 103:2738-2743 (2004).
Czuczman et al., Journal of Clinical Oncology, 17(1): 268-276 (1999).
D'Ambrosio et al., J. of Immunology, Cutting Edge, 0022-1767/98/502.00, pp. 5111-5115 (1998).
da Silva et al., the Journal of Immunology, 168:4462-4471 (2002).
Davies et al., Biotechnology and Bioengineering, 74(4):288-294 (2001).

Denning et al., Nat. Biotech, 19:559-562 (2001).
Dermer, Bio/Technology, 12:320 (1994).
Dharmacon siRNA design for AB025198, accessed http://www.dharmacon.com/DesignCenter/DesignCenterPage.aspx on Apr. 15, 2008.
Dharmacon siRNA design for AF042377, accessed http://www.dharmacon.com/DesignCenter/DesignCenterPace.aspx on Apr. 15, 2008.
Domagala et al., Med. Sci., Monit., 7(2):325-331 (2001).
Domino et al., Molecular and Cellular Biology, 21(24):8336-8345 (2001).
Duncan et al.; *Molecular Immunology*, 44:3641-3652 (2007).
Edmunds et al., Blood, 91(12):4561-4571 (1998).
Elbashir et al., Nature, 411:494-498 (2001).
Environmental Conditions for Cell Growth, Part 2C.
EP 00969908- Supplementary European Search Report dated Apr. 18, 2005.
EP 00969908.3 - Office Action issued Jul. 30, 2007.
EP 01974718.7-Supplementary European Search Report dated May 19, 2005.
EP 01974718.7 Supplementary European Search Report dated Jun. 1, 2005.
EP 03723096 Supplementary European Search Report dated Oct. 27, 2006.
EP 02793391 Supplementary European Search Report dated Mar. 28, 2006.
EP 03723097 Supplementary European Search Report dated Sep. 11, 2006.
EP 03723098 Supplementary European Search Report dated Nov. 14, 2006.
EP 03723099.2 Supplementary European Search Report dated Nov. 14, 2006.
EP 03720896 Supplementary European Search Report dated Jul. 22, 2005.
EP 03720897.2 Supplementary European Search Report dated Jul. 18, 2006.
EP 04773700 Supplementary European Search Report dated Aug. 21, 2008.
EP 04773766.3 Supplementary European Search Report dated Oct. 16, 2006.
EP 04773768.9 European Search Report dated Mar. 10, 2009.
EP 04773769 Supplementary European Search Report dated Feb. 7, 2007.
EP 04773774.7 Supplementary European Search Report dated Aug. 28, 2007.
EP 04773775 Supplementary European Search Report dated Nov. 27, 2008.
EP 04773776 Supplementary European Search Report dated Nov. 19, 2007.
EP 04773776.2 Supplementary Partial European Search Report dated Aug. 2, 2007.
EP 04801651.3 Supplementary European Search Report dated Feb. 20, 2008.
EP 05768941 European Search Report dated Dec. 27, 2007.
EP 05799028 Supplementary European Search Report dated Mar. 10, 2008.
Ersdal-Badju et al., Biochem. J., 310:323-330 (1995).
Ferrara et al., Biotechnology and Bioengineering; 93(5):851-861 (2006).
Finne et al., Inter. J. of Cancer, 43(2):300-304 (1989).
Flieger et al., Hybridoma, 18(1):63-68 (1999).
Frade et al., J. Clin. Invest., 100(3):497-502 (1997).
Franzen et al., J. Biol. Chem., 255(11):5090-5093 (1980).
Freshney, Culture of Animal Cells, A Manual of Basic Techniques, Alan R. Liss, Inc., New York, p. 4 (1983).
Friedberg et al., British Journal of Hematology, 117:828-834 (2002).
Garone et al., Biochem., 35:8881-8889 (1996).
Gawlitzek et al., Biotechnology and Bioengineering, 68(6):637-646 (2000).
Gerard et al., Nature Inimunol. 2:108-115 (2001).
Ginaldi et al, Leukemia Research, 22(2):185-191 (1998).
Glycine Msds, Mallinckrodt chemicals, p. 1-6 (2005).
Goeddel, Chest, 116:1-8 (1999).
Goldenberg, Clinical Therapeutics, 21(2):309-317 (1999).
Gomez et al., Mol. Biol. Evol., 21:266-275 (2004).
Grabenhorst et al., Glycoconjugate Journal., 16(2):81-97 (1999).
Griffiths, Microscopy Research and Technique, 41(5):344-358 (1998).
Hackett et al., J. of Clinical Microbiology, 36(5):1277-1284 (1998).
Hagberg et al., Medical Oncolology, 22:191-194 (2005).
Haidar et al., Eur. J. Haematol., 70:330-332 (2003).
Hallouin et al., Inter. J. of Cancer, 80(4):606-611 (1999).
Hanson et al., Molecular and Cellular Biology, 15(1):45-51 (1995).
Harada et al., Sanfujinka Chiryo, 86(6):1048-1054 (2003).
Hasty et al., "Gene targeting vectors for mammalian cells", In: Joyner Al, editor, Gene Targeting, New York: Oxford University Press, pp. 1-31 (Year).
Hayashi et al.; DNA Sequence; 11(1-2):91-96 (2000).
He et al., J. Immunol., 160(2):1029-1035 (1998).
Hennett et al., Biochemica et Biophysica Acta, 1473(1):123-136 (1999).
Hirose et al., Thrombosis Research, 119:631-641(2007).
Hirschberg, Journal of Clinical Investigation, 108(1):3-6 (2001).
Holschneider et al., Int. J. Dev. Neuroscience, 18(6):615-618 (2000).
Horowitz et al., Proc. Natl. Acad. Sci., USA, 85:8678-8682 (1988).
Houdebine, J. Biotech., 34:269-287 (1994).
Huang et al., J. of Biol. Chemistry, 275(40):31353-31360 (2000).
Humpherys et al., Science, 293:95-97 (2001).
Hunter et al., Current Biology, 9:R440-R442 (1999).
Idusogie et al., The Journal of Immunology, 164:4178-4184 (2000).
Iellem et al., J. Exp. Med., 194(6):847-853 (2001).
iHOP, www.ihop-net.org, p. 1.
Imai et al., International Immunology, 11(1):81-88 (1999).
Javaud et al., Molecular Biology and Evolution, 17(11):1661-1672 (2000).
Jen et al., Stem Cells, 18:307-319 (2000).
Joshi et al., Curr. Opin. Plant Biol., 8:223-226, Abstract (2005).
Jones et al., Blood, 96(2):685-690 (2000).
JP 2000611663 - Telephonic Correspondence Record issued Apr. 15, 2009 (and attached Third Party Observation).
Junghans et al., Cancer Res., 50(5):1495-1502 (1990).
Kabat et al., Sequences of proteins of immunological interest, 4th Edition, pp. 307-308 (1987).
Kanazawa et al., Cancer Immunology Immunotherapy, 49(4-5):253-258 (2000).
Kanda et al.; Biotechnology and Engineering, 94(4):680-688 (2006).
Kanda et al., J. of Biotechnology, 130(3):300-310 (2007).
Kappel et al., Current Opinion in Biotechnology, 3:548-553 (1992).
Kashmiri et al., Methods, 36:25-34 (2005).
Kawai et al., Nature, 409(6821):685-690 (2001).
Keen et al., Biology Research Division, United Kingdom., 17:193-202 (1995).
Kilmartin et al.; J. of Cell Biology, 93:576-582 (1982).
Kim et al., Arch. Pharm. Res., 20(4):297-305 (1997).
Kirchhoff, Biology of Reproduction, 50:896-902 (1994).
Kojima et al., Journal of Biochemistry, 124:726-737 (1998).
Koyama et al., Int. J. Gynecol. Obstet., 43:45-50 (1993).
Kruszewska et al., Glycobiology, 10(10):983-991 (2000).
Kubota et al, J. of Immunology, 145(11):3924-3931 (1990).
Kuroiwa et al., Nature Genetics, 36(7):775-780 (2004).
Kushihata et al., Transplantation, 78(7):995-1001 (2004).
Kusumoto, lgaku no Ayumi (Progress Med. Sc), 190(5):522-529 (1999).
Ladisch et al., *The Lancet*, pp. 136-138 (1985).
Landolfi et al., J. Immunol., 166(3):1748-1754 (2001).
Lazar et al., Mol. & Cell Bio., 8:1247-1252 (1988).
Lederman et al., Mol. Immunol. 28:1171-1181(1991).
Letter from Terry Kramer dated May 9, 2005 and Third Party Submission dated May 9, 2005 (received May 12, 2005).
Leonard et al., Immunological Reviews, 148:97-114 (1995).
Li et al., Acta Pharmacologicia Sinica, 21(11):1005-1010 (2000).
Liu et al., Mechanisms of Development, 116:227-230 (2002a).
Liu et al., J. of Cancer Res. and Clinical Oncology, 128(4):189-196 (2002b).
Lubiniecki et al., Dev. Biol. Stand., 99:153-156 (1999).
Lubke et al., Nature Genetics, 28(1):73-76 (2001).

Luhtala et al., Poultry Science, 77:1858-1873 (1998).
Luhn et al., Nature Genetics, 28(1):69-72 (2001).
Lyons et al., Current Biology, 15:513-524 (2005).
Ma et al., Glycobiology, 16(12):158R-184R (2006).
MacEwan; Cellular Signaling, 14:477-492 (2002).
Majeau et al., Journal of Immunology, 152:2753-2767 (1994).
Manfredi et al., Cancer Res., 59:5392-5397 (1999).
Marshall et al., Blood, 103(5):1755-1762 (2004).
Martinez-Duncker et al., Glycobiology, 14(1):13-25 (2004).
Merck Manuals Online Medical Library, Whitehouse Station, NJ: Merck Research Laboratories, 2006-2007, retrieved Oct. 2007, http://www.merck.com/mmpe/print/sec11ch143/ch143b.html, Hodgkin lymphoma, p. 1-5.
Merck Manuals Online Medical Library, Whitehouse Station, NJ: Merck Research Laboratories, 2006-2007, retrieved Oct. 2007, http://www.merck.com/mmpe/print/sec11ch142/ch142a.html, Leukemia, pages1-4.
Michaelsen et al., Scandinavian Journal of Immunology, 32:517-528 (1990).
Moreadith et al., J. Mol. Med., 75:208-216 (1997).
Mori et al., Biotechnology and Bioengineering, 88(7):901-908 (2004).
Mueller et al., J. of Immunology, 144(4):1382-1386 (1990).
Mullins et al., Journal of Clinical Investigation, 97(7):1557-1560 (1996).
Murray et al., the Annals of Pharmacotherapy, 31:1335-1338 (1997).
Nakamura et al., Cancer Research, 54:1511-1516 (1994).
Nakamura et al., Cancer Research, 59(20):5323-5330 (1999).
Nakamura et al., Molecular Immunology, 37:1035-1046 (2000).
Natsumi et al., J. of Immunol. Methods, 306:93-103 (2005).
Nishii et al., Br. J. Haematol., 91:169-172 (1995).
Niwa et al., Clinical Cancer Research, 10:6248-6255 (2004).
Norderhaug et al., European Journal of Immunology, 21:2379-2384 (1991).
Okajima et al., Cell, 111(6):893-904 (2002).
Okazaki et al., Seikagaku, 77:45-50 (2005).
Olson et al., Arch. Biochem. Biophys., 341(2):212-221 (1997).
Omasa et al., Journal of Bioscience and Bioengineering, 106(2):168-173 (2008).
Onishi, Igaku no Ayumi (Progress Med. Sci.), 190(5):481-485 (1999).
Onizuka et al., Cancer Research, 59:3128-3133 (1999).
Ozturk et al., Journal of Biotechnology, 16:259-278 (1990).
Padlan et al., PNAS, 86:5938-5942 (1989).
Pastuszak et al.; J. of Biological Chemistry, 273(46):30165-30174 (1998).
PCT/JP2004/015315 International Search Report dated Feb. 1, 2005.
PCT/JP2004/015317 International Search Report dated Feb. 1, 2005.
PCT/JP2004/015325 International Search Report dated Feb. 1, 2005.
PCT/JP2005/014408 International Preliminary Report on Patentability dated Feb. 6, 2007.
Pearson, Nature, 415(6867):8-9 (2002).
Peipp et al.; *Blood*., 112:2390-2399 (2008).
Pierrot et al., Biochemical and Biophysical Res. Comm., 288:328-339 (2001).
Polejaeva et al., Theriogenology, 53(1): 117-126 (2000).
Power et al., J. Of Biological Chemistry, 270(33):19495-19500 (1995).
Prati et al., Biotechnology and Bioengineering, 59(4):445-450 (1998).
Priatel et al., Glycobiology, 7(1):45-56 (1997).
Pulczynski et al., Blood, 6:1549-1557 (1993).
Pulglielli et al., The J. of Biological Chemistry, 274(50):35596-35600 (1999).
Queen et al., Proc. Natl. Acad. Sci., 86(24):10029-10033 (1989).
Rader et al., PNAS, 95:8910-8915 (1998).
Rasmussen et al., Cytotechnology, 28:31-42 (1998).
Reitman et al., J. of Biological Chemistry, 255(20):9900-9906 (1980).
Reynolds et al., Nature Biology, 3:326-330 (2004).
Riechman et al., Nature, 332:323-327 (1988).
Ritter et al., Semin. Cancer Biol., 2:401-409 (1991).

Roos et al., Hematologically Important Mutations: Leukocytes Adhesion Deficiency, Blood Cells, Molecules, and Diseases, 276(6):1000-1004 (2001).
Rudikoff et al., Proc. Natl. Adac. Sci., USA, 79:1979-1983 (1982).
Rulicke et al., Experimental Physiology, 85:589-601 (2000).
Ruohola et al., Cancer Research, 61(10):4229-4237 (2001):.
Schianova et al., Curr. Pharm. Design, 10:769-784 (2004).
Schimanski et al., World J. Gastroenterol., 14:4721-4724 (2008).
Scott et al., *Cytokine*, 12(7):858-866 (2000).
Seffernick et al., J. Bacteriol. 183(8):2405-2410 (2001).
Shafi et al., PNAS, 97(11):5735-5739 (2000).
Sharp, Genes & Development, 15:485-490 (2001).
Shibuya et al., Biol. Chem., 383:1573-1579 (2002).
Shields et al., The Journal of Biological Chemistry, 276(9):6591-6604 (2001).
Shinoda et al., Glycobiology Journal, 15:1079-1083 (1998).
Shoji-Hosaka et al., Journal of Biochemistry, 140(6):777-783 (2006).
Sigmund, Arteroscler. Throm. Vasc. Biol., 20:1425-1429 (2000).
Sims et al., The Journal of Immunology, 151(4):2296-2308 (1993).
Slevin et al., Int. J of Cancer, 82:412-423 (1999).
Smith et al., J.of Cell Biology, 158(4):801-815 (2002).
Sondel et al., Cancer Journal from Scientific American, 3(Suppl. 1):S121-S127 (1997).
Sorbera et al., Drugs of the Future, 26(6):527-532 (2001).
Sousa et al., The J. of Biological Chemistry, 278(9):7624-7629 (2003).
Staudacher et al., Biochemica et Biophysica Acta, 1473:216-236 (1999).
Stein et al., *J. Mol. Evol.*, 50:397-412 (2000).
Stevenson et al., Bioscience Report., 5(12):1071-1077 (1985).
Suzuki et al., International Immunology, 11(4):553-559 (1999).
Suzuki et al., Clinical Cancer Research, 13(6):1875-1882 (2007).
Tachibana et al., In Vitro Cell. and Dev. Biology Animal, 31(4):261-262 (1995).
Takahashi et al., Glycobiology, 10(5):503-510 (2000).
Takeuchi, Igaku no Ayumi (Progress Med. Sci.), 190(5):474-480 (1999).
Tao et al., Journal of Experimental Medicine, 178:661-667 (1993).
Tijsterman et al., Annu. Rev. Genet., 36:489-519 (2002).
Tonetti et al., The Journal of Biological Chemistry, 271(44):27274-27279 (1996).
Treumann et al., J. of Biological Chemistry, 270(11):6088-6099 (1995).
Tutt et al., The Journal of Immunology, 161:3176-3185 (1998).
Umana et al., Nature Biotechnology, 17:176-180 (1999).
Umana et al, drugdisc.com/2005/brochure.pdf, May 12, 2005 (2005).
Valve et al., Laboratory Investigation, 81(6):815-826 (2001).
Van Den Berg et al., Am. J. of Pathology, 154(6):1685-1691 (1999).
Van Der Kolk et al., Leukemia, 17:1658-1664 (2003).
Wall, Theriogenology, 45:57-68 (1996).
Wall et al., J. Dairy Sci. 80:2213-2224 (1997).
Wang et al., Proc. Natl., Acad. Sci., USA, 102(44):15791-15796 (2005).
Wang et al., Journal of Biological Chemistry, 273(14):8112-8118 (1998).
Wells et al., Inflamm. Res. 48:353-362 (1999).
Wheeler et al., Theriogenology, 56:1345-1369 (2001).
Wild et al., Cells Tissues Organs, 172:161-173 (2002).
Willer et al., Proc. Natl. Acad. Sci., USA, 101(39):14126-14131 (2004).
Witkowski et al., Biochemistry, 38(36):11643-11650 (1999).
Wolf et al., Experimental Physiology, 85(6):615-625 (2000).
Wu et al., J. of Clinical Investigation, 100(5):1059-1070 (1997).
Xia et al., Biochem. J., 293:633-640 (1993).
Yamaguchi et al., Glycobiology, 10(6):637-643 (2000).
Yamaguchi et al., Biochemical & Biophysical Res. Comm., 291:554-559 (2002).
Yanagidani et al., J. of Biochemistry, 121(3):626-632 (1997).
Yanagimachi, Mol. Cell Endocrinol., 187:241-248 (2002).
Yokoi et al., Cancer Research, 65:10371-10380 (2005).
Yoneyama et al., J. Clin. Invest., 102(11):1933-1941 (1998).
Youn et al., Blood, 89(12):4448-4460 (1997).
Yuyama et al., Cancer, 75(6):1273-1280 (1995).

Zeitlin etal., Nature Biotechnology, 16:1361-1364 (1998).
Zettimeissl et al., J. Biol. Chem., 264(35):21153-21159 (1989).
Zhou et al., Biotechnology and Bioengineering, 55(5):783-792 (1997).
Zhou et al., Cytotechnology, 22(1-3): 239-250 (1996).
Zhou et al.. Genbank Accession No. NP 058589, J. Biol. Chem., 281(50):38343-38350 (2006).
Zhou et al., Genbank Accession No. NM 016893, J. Biol., Chem., 281(50):38343-38350 (2006).
Zhou et al., Nucleic Acids Research, 30(7):1664-1669 (2002).
Restriction Requirement issued Apr. 28, 2004 in U.S. Appl. No. 09/958,307.
Response to Restriction Requirement filed May 26, 2004 in U.S. Appl. No. 09/958,307.
Non-Final OA issued Jun. 16, 2004 in U.S. Appl. No. 09/958,307.
1.111 Amendment filed Nov. 22, 2004 in U.S. Appl. No. 09/958,307.
Supplemental 1.111 Amendment filed Dec. 14, 2004 in UU.S. Appl. No. 09/958,307.
Final OA issued Mar. 1, 2005 in U.S. Appl. No. 09/958,307.
1.116 Amendment filed May 2, 2005 in U.S. Appl. No. 09/958,307.
Supplemental 1.116 Amendment filed May 11, 2005 in U.S. Appl. No. 09/958,307.
Advisory Action issued May 12, 2005 in U.S. Appl. No. 09/958,307.
Advisory Action issued May 23, 2005 in U.S. Appl. No. 09/958,307.
Restriction Requirement issued Jan. 27, 2006 in U.S. Appl. No. 11/126,176.
Response to Restriction Requirement and Preliminary Amendment filed Mar. 27, 2006 in U.S. Appl. No. 11/126,176.
Non-Final OA issued May 19, 2006 in U.S. Appl. No. 11/126,176.
1.111 Amendment filed Aug. 21, 2006 in U.S. Appl. No. 11/126,176.
Final OA issued Nov. 15, 2006 in U.S. Appl. No. 11/126,176.
1.116 Amendment filed Nov. 21, 2006 in U.S. Appl. No. 11/126,176.
Notice of Allowance issued Dec. 28, 2006 in U.S. Appl. No. 11/126,176.
Restriction Requirement issued Jul. 17, 2007 in U.S. Appl. No. 11/126,299.
Response to Restriction Requirement filed Aug. 17, 2007 in U.S. Appl. No. 11/126,299.
Non-Final OA issued Nov. 1, 2007 in U.S. Appl. No. 11/126,299.
1.111 Amendment and Terminal Disclaimer filed Apr. 4, 2008 in U.S. Appl. No. 11/126,299.
Final OA mailed Jul. 8, 2008 in U.S. Appl. No. 11/126,299.
RCE and 1.114 Response filed Dec. 31, 2008 in U.S. Appl. No. 11/126,299.
Non-Final OA issued Apr. 16, 2009 in U.S. Appl. No. 11/126,299.
Restriction Requirement issued May 17, 2007 in U.S. Appl. No. 11/126,298.
Response to Restriction Requirement filed Jun. 15, 2007 in U.S. Appl. No. 11/126,298.
Non-Final OA issued Aug. 24, 2007 in U.S. Appl. No. 11/126,298.
1.111 Amendment filed Feb. 22, 2008 in U.S. Appl. No. 11/126,298.
Non-Final OA issued May 15, 2008 in U.S. Appl. No. 11/126,298.
1.111 Amendment filed Aug. 15, 2008 in U.S. Appl. No. 11/126,298.
Final OA issued Nov. 28, 2008 in U.S. Appl. No. 11/126,298.
1.116 Amendment and Terminal Disclaimer filed Feb. 2, 2009 in U.S. Appl. No. 11/126,298.
Advisory Action issued Feb. 27, 2009 in U.S. Appl. No. 11/126,298.
Notice of Allowance issued Mar. 16, 2009 in U.S. Appl. No. 11/126,298.
RCE filed Jun. 16, 2009, in U.S. Appl. No. 11/126,298.
Non-Final OA issued Oct. 1, 2008 in U.S. Appl. No. 11/686,379.
1.111 Amendment and Terminal Disclaimer filed Jan. 2, 2009 in U.S. Appl. No. 11/686,379.
Notice of Allowance issued Apr. 28, 2009 in U.S. Appl. No. 11/686,379.
Non-Final OA issued Oct. 1, 2008 in U.S. Appl. No. 11/686,391.
1.111 Amendment and Terminal Disclaimer filed Jan. 2, 2009 in U.S. Appl. No. 11/686,391.
Notice of Allowance issued May 1, 2009 in U.S. Appl. No. 11/686,391.
Non-Final OA issued Oct. 2, 2008 in U.S. Appl. No. 11/686,404.
1.111 Amendment and Terminal Disclaimer filed Jan. 2, 2009 in U.S. Appl. No. 11/686,404.

Notice of Allowance issued Feb. 24, 2009 in U.S. Appl. No. 11/686,404.
RCE filed May 25, 2009 in U.S. Appl. No. 11/686,404.
Notice of Allowance issued Jun. 26, 2009, in U.S. Appl. No. 11/686,404.
Non-Final OA issued Oct. 1, 2008 in U.S. Appl. No. 11/686,458.
1.111 Amendment and Terminal Disclaimer filed Jan. 2, 2009 in U.S. Appl. No. 11/686,458.
Notice of Allowance issued Feb. 24, 2009 in U.S. Appl. No. 11/686,458.
RCE filed May 25, 2009 in Ussn 11/686,458.
Notice of Allowance issued Jun. 26, 2009, in U.S. Appl. No. 11/686,458.
Non-Final OA issued Sep. 30, 2008 in U.S. Appl. No. 11/686,906.
1.111 Amendment and Terminal Disclaimer filed Dec. 30, 2008 in U.S. Appl. No. 11/686,906.
Notice of Allowance issued Feb. 24, 2009 in U.S. Appl. No. 11/686,906.
RCE filed May 25, 2009 in U.S. Appl. No. 11/686,906.
Notice of Allowance issued Jun. 26, 2009 in U.S. Appl. No. 11/686,906.
Non-Final OA issued Dec. 10, 2008 in U.S. Appl. No. 11/686,911.
1.111 Amendment and Terminal Disclaimer filed Jun. 10, 2009 in U.S. Appl. No. 11/686,911.
Notice of Allowance issued Jul. 10, 2009 in U.S. Appl. No. 11/686,911.
Non-Final OA issued Dec. 10, 2008, in U.S. Appl. No. 11/686,920.
1.111 Amendment and Terminal Disclaimer filed Apr. 10, 2009 in U.S. Appl. No. 11/686,920.
Notice of Allowance issued May 18, 2009 in U.S. Appl. No. 11/686,920.
Non-Final OA issued May 19, 2005 in U.S. Appl. No. 10/110,997.
1.111 Amendment filed Nov. 21, 2005 in U.S. Appl. No. 10/110,997.
Non-Final OA issued Feb. 8, 2006 in U.S. Appl. No. 10/110,997.
1.111 Amendment filed Aug. 4, 2006 in U.S. Appl. No. 10/110,997.
Final OA issued Nov. 2, 2006 in U.S. Appl. No. 10/110,997.
1.116 Amendment filed Mar. 1, 2007 in U.S. Appl. No. 10/110,997.
Advisory Action issued Mar. 22, 2007 in U.S. Appl. No. 10/110,997.
RCE filed Apr. 2, 2007 in U.S. Appl. No. 10/110,997.
Final OA issued Jul. 5, 2007 in U.S. Appl. No. 10/110,997.
Non-Final OA issued Sep. 12, 2007 in U.S. Appl. No. 10/110,997.
1.111 Amendment filed Feb. 7, 2008 in U.S. Appl. No. 10/110,997.
Notice of Non-Compliant Amendment issued Jun. 17, 2008 in U.S. Appl. No. 10/110,997.
Response to Notice of Non-Compliant Amendment filed Jul. 9, 2008 in U.S. Appl. No. 10/110,997.
Notice of Allowance issued Nov. 3, 2008 in U.S. Appl. No. 10/110,997.
Restriction Requirement issued Jun. 17, 2003 in U.S. Appl. No. 09/971,773.
Response to Restriction Requirement filed Sep. 17, 2003 in U.S. Appl. No. 09/971,773.
Notice of Non-Responsive Response issued Oct. 7, 2003 in U.S. Appl. No. 09/971,773.
Response to Notice of Non-Response Response filed Dec. 8, 2003 in U.S. Appl. No. 09/971,773.
Non-Final OA issued Feb. 13, 2004 in U.S. Appl. No. 09/971,773.
1.111 Amendment filed Aug. 12, 2004 in U.S. Appl. No. 09/971,773.
Final OA issued Nov. 3, 2004 in U.S. Appl. No. 09/971,773.
1.116 Amendment filed Dec. 17, 2004 in U.S. Appl. No. 09/971,773.
Advisory Action issued Jan. 25, 2005 in U.S. Appl. No. 09/971,773.
1.116 Amendment filed Feb. 2, 2005 in U.S. Appl. No. 09/971,773.
Advisory Action issued Mar. 21, 2005 in U.S. Appl. No. 09/971,773.
Notice of Allowance issued Apr. 5, 2005 in U.S. Appl. No. 09/971,773.
Supplemental Submission under 37 C.F.R. § 1.116 filed Dec. 28, 2004, in U.S. Appl. No. 09/971,773.
Restriction Requirement issued Sep. 22, 2006 in U.S. Appl. No. 11/131,212.
Response to Restriction Requirement filed Oct. 18, 2006 in U.S. Appl. No. 11/131,212.
Non-Final OA issued Jan. 12, 2007 in U.S. Appl. No.11/131,212.

1.111 Amendment and Terminal Disclaimer filed Jul. 12, 2007 in U.S. Appl. No. 11/131,212.
Non-Final OA issued Sep. 7, 2007 in U.S. Appl. No. 11/131,212.
1.111 Amendment filed Mar. 6, 2008 in U.S. Appl. No. 11/131,212.
Non-Final OA issued Jun. 5, 2008 in in U.S. Appl. No. 11/131,212.
1.111 Amendment and Terminal Disclaimer filed Jul. 29, 2008 in U.S. Appl. No. 11/131,212.
Final OA issued Nov. 24, 2008 in U.S. Appl. No. 11/131,212.
1.116 Amendment and Terminal Disclaimer filed Feb. 24, 2009 in U.S. Appl. No. 11/131,212.
Advisory Action issued Apr. 6, 2009 in U.S. Appl. No. 11/131,212.
RCE, 1.114 Amendment and Terminal Disclaimer filed Apr. 23, 2009 in U.S. Appl. No. 11/131,212.
Non-Final Office Action issued Jul. 9, 2009 in U.S. Appl. No. 11/131,212.
Non-Final OA issued Sep. 11, 2007 in U.S. Appl. No. 11/218,473.
Non-Final OA issued Oct. 18, 2007 in U.S. Appl. No. 11/218,473.
1.111 Amendment filed Apr. 18, 2008 in U.S. Appl. No. 11/218,473.
Final OA issued Jul. 25, 2008 in U.S. Appl. No. 11/218,473.
RCE and 1.114 Response and Terminal Disclaimers filed Nov. 25, 2008 in U.S. Appl. No. 11/218,473.
Non-Final OA issued Mar. 5, 2009 in U.S. Appl. No. 11/218,473.
1.111 Amendment filed Jun. 5, 2009 in U.S. Appl. No. 11/218,473.
Restriction Requirement issued Oct. 31, 2006 in U.S. Appl. No. 11/240,579.
Response to Restriction Requirement and Preliminary Amendment filed Nov. 30, 2006 in U.S. Appl. No. 11/240,579.
Non-Final OA issued Mar. 9, 2007 in U.S. Appl. No. 11/240,579.
Non-Final OA issued May 10, 2007 in U.S. Appl. No. 11/240,579.
1.111 Amendment filed Nov. 13, 2007 in in U.S. Appl. No. 11/240,579.
Final OA issued Feb. 14, 2008 in U.S. Appl. No. 11/240,579.
Notice of Appeal filed Aug. 14, 2008 in U.S. Appl. No. 11/240,579.
RCE and 1.114 Amendment filed Oct. 14, 2008 in U.S. Appl. No. 11/240,579.
Non-Final OA issued Jan. 7, 2009 in U.S. Appl. No. 11/240,579.
1.111 Amendment filed Apr. 7, 2009 in U.S. Appl. No. 11/240,579.
Restriction Requirement issued Dec. 5, 2006 in U.S. Appl. No. 11/287,324.
Response to Restriction Requirement filed Jan. 3, 2007 in U.S. Appl. No. 11/287,324.
Non-Final OA issued Mar. 22, 2007 in U.S. Appl. No. 11/287,324.
1.111 Amendment filed Sep. 24, 2007 in U.S. Appl. No. 11/287,324.
Notice of Allowance issued Jan. 7, 2008 in U.S. Appl. No. 11/287,324.
Restriction Requirement issued Dec. 5, 2006 in U.S. Appl. No. 11/287,359.
Response to Restriction Requirement filed Jan. 3, 2007 in U.S. Appl. No. 11/287,359.
Non-Final OA issued Mar. 22, 2007 in U.S. Appl. No. 11/287,359.
Non-Final OA issued Apr. 19, 2007 in U.S. Appl. No. 11/287,359.
1.111 Amendment and Terminal Disclaimer filed Jul. 19, 2007 in U.S. Appl. No. 11/287,359.
Final OA issued Oct. 3, 2007 in U.S. Appl. No. 11/287,359.
1.116 Amendment filed Feb. 22, 2008 in U.S. Appl. No. 11/287,359.
Supplemental 1.116 Amendment fijed Mar. 3, 2008 in U.S. Appl. No. 11/287,359.
Advisory Action issued Mar. 17, 2008 in U.S. Appl. No. 11/287,359.
Supplemental 1.116 Response and Terminal Disclaimer filed Mar. 25, 2008 in U.S. Appl. No. 11/287,359.
Notice of Appeal filed Apr. 3, 2008 in U.S. Appl. No. 11/287,359.
Notice of Allowance issued May 2, 2008 in U.S. Appl. No. 11/287,359.
Non-Final OA issued Sep. 17, 2007 in U.S. Appl. No. 11/279,748.
Non-Final OA issued Oct. 18, 2007 in U.S. Appl. No. 11/279,748.
1.111 Amendment (with Terminal Disclaimers) filed Mar. 18, 2008 in U.S. Appl. No. 11/279,748.
Election of Species Requirement issued Jun. 13, 2008 in U.S. Appl. No. 11/279,748.
Response to Election of Species filed Jul. 14, 2008 in U.S. Appl. No. 11/279,748.
Final Office Action issued Sep. 30, 2008 in U.S. Appl. No. 11/279,748.
1.116 Amendment (with Terminal Disclaimer) filed Dec. 29, 2008 in U.S. Appl. No. 11/279,748.
Advisory Action issued Feb. 11, 2009 in U.S. Appl. No. 11/279,748.
Request for Continued Examination filed Feb. 27, 2009, in U.S. Appl. No. 11/279,748.
Non-Final Office Action issued May 28, 2009, in U.S. Appl. No. 11/279,748.
Restriction Requirement issued Apr. 21, 2004 in U.S. Appl. No. 10/327,663.
Response to Restriction Requirement and Preliminary Amendment filed May 21, 2004 in U.S. Appl. No. 10/327,663.
Restriction Requirement issued Jul. 29, 2004 in U.S. Appl. No. 10/327,663.
Response to Restriction Requirement filed Aug. 27, 2004 in U.S. Appl. No. 10/327,663.
Non-Final OA issued Nov. 9, 2004 in U.S. Appl. No. 10/327,663.
1.111 Amendment filed Feb. 3, 2005 in U.S. Appl. No. 10/327,663.
Non-Final OA issued Apr. 7, 2005 in U.S. Appl. No. 10/327,663.
Restriction Requirement issued Feb. 10, 2006, in U.S. Appl. No. 10/409,616.
Response to Restriction Requirement filed Apr. 10, 2006, in U.S. Appl. No. 10/409,616.
Non-Final Office Action issued Jun. 14, 2006, in U.S. Appl. No. 10/409,616.
1.111 Amendment (with IDS) filed Nov. 14, 2006, in U.S. Appl. No. 10/409,616.
Final Office Action issued Sep. 17, 2007, in U.S. Appl. No. 10/409,616.
1.116 Amendment filed Feb. 21, 2008, in U.S. Appl. No. 10/409,616.
Advisory Action issued Mar. 17, 2008, in U.S. Appl. No. 10/409,616.
Notice of Appeal filed Mar. 17, 2008, in U.S. Appl. No. 10/409,616.
Request for Continued Examination (with 1.114c Amendment) filed Apr. 4, 2008, in U.S. Appl. No. 10/409,616.
Notice of Non-Compliant Amendment issued Jul. 10, 2008, in U.S. Appl. No. 10/409,616.
Response to Notice of Non-Compliant Amendment filed Aug. 1, 2008, in U.S. Appl. No. 10/409,616.
Non-Final Office Action issued Jan. 23, 2009, in U.S. Appl. No. 10/409,616.
Restriction Requirement issued Jul. 26, 2004, in U.S. Appl. No. 10/409,609.
Response to Restriction Requirement filed Sep. 27, 2004, in U.S. Appl. No. 10/409,609.
Non-Final Office Action issued Nov. 18, 2004, in U.S. Appl. No. 10/409,609.
Notice of Abandonment issued Sep. 6, 2005, in U.S. Appl. No. 10/409,609.
Restriction Requirement issued Nov. 16, 2006, in U.S. Appl. No. 11/127,173.
Response to Restriction Requirement filed Dec. 13, 2006, in U.S. Appl. No. 11/127,173.
Non-Final Office Action issued Mar. 9, 2007, in U.S. Appl. No. 11/127,173.
1.111 Amendment filed Sep. 10, 2007, in U.S. Appl. No. 11/127,173.
Non-Final Office Action issued Dec. 4, 2007, in U.S. Appl. No. 11/127,173.
Non-Final Office Action issued May 22, 2008, in U.S. Appl. No. 11/127,173.
1.111 Amendment filed Aug. 22, 2008, in U.S. Appl. No. 11/127,173.
Restriction Requirement issued Nov. 26, 2008, in U.S. Appl. No. 11/127,173.
Response to Restriction Requirement issued Dec. 29, 2008, in U.S. Appl. No. 11/127,173.
Final Office Action issued Mar. 19, 2009, in U.S. Appl. No. 11/127,173.
Restriction Requirement issued Sep. 7, 2005, in U.S. Appl. No. 10/409,600.
Response to Restriction Requirement filed Oct. 6, 2005, in U.S. Appl. No. 10/409,600.
Notice of Non-Compliant Amendment issued Dec. 12, 2005, in U.S. Appl. No. 10/409,600.
Response to Notice of Non-Compliant Amendment filed Jan. 9, 2006, in U.S. Appl. No. 10/409,600.

Non-Final Office Action issued Mar. 6, 2006, in U.S. Appl. No. 10/409,600.
1.111 Amendment (with Declaration and IDS) filed Sep. 6, 2006, in U.S. Appl. No. 10/409,600.
Final Office Action issued Nov. 27, 2006, in U.S. Appl. No. 10/409,600.
1.116 Amendment (with Declaration) filed Apr. 27, 2007, in U.S. Appl. No. 10/409,600.
Non-Final Office Action issued May 30, 2007, in U.S. Appl. No. 10/409,600.
1.111 Amendment filed Nov. 30, 2007, in U.S. Appl. No. 10/409,600.
Restriction Requirement issued Apr. 30, 2008, in U.S. Appl. No. 10/409,600.
Response to Restriction Requirement and 1.111 Amendment filed May 30, 2008, in U.S. Appl. No. 10/409,600.
Notice of Non-Complaint Amendment mailed Jun. 6, 2008, in U.S. Appl. No. 10/409,600.
Response to Notice of Non-Complaint Amendment and Supplemental 1.111 Amendment filed Jun. 16, 2008, in U.S. Appl. No. 10/409,600.
Non-Final Office Action issued Jan. 6, 2009, in U.S. Appl. No. 10/409,600.
1.111 Amendment filed Apr. 6, 2009, in U.S. Appl. No. 10/409,600.
Final Office Action issued Jun. 22, 2009, in U.S. Appl. No. 10/409,600.
Restriction Requirement issued Aug. 24, 2005, in U.S. Appl. No. 10/409,598.
Amendment (Response to Restriction Requirement) filed Nov. 25, 2005, in U.S. Appl. No. 10/409,598.
Non-Final Office Action issued Jan. 30, 2006, in U.S. Appl. No. 10/409,598.
1.111 Amendment filed Jul. 26, 2006, in U.S. Appl. No. 10/409,598.
Final Office Action issued Oct. 31, 2006, in U.S. Appl. No. 10/409,598.
1.116 Amendment filed Feb. 28, 2007, in U.S. Appl. No. 10/409,598.
Advisory Action issued Mar. 14, 2007, in U.S. Appl. No. 10/409,598.
Request for Continued Examination filed Mar. 30, 2007, in U.S. Appl. No. 10/409,598.
Non-Final Office Action issued Jul. 5, 2007, in U.S. Appl. No. 10/409,598.
1.111 Amendment filed Jan. 4, 2008, in U.S. Appl. No. 10/409,598.
Non-Final Office Action issued Apr. 4, 2008, in U.S. Appl. No. 10/409,598.
1.111 Amendment filed Aug. 4, 2008, in U.S. Appl. No. 10/409,598.
Final Office Action issued Oct. 27, 2008, in U.S. Appl. No. 10/409,598.
1.116 Amendment filed Jan. 30, 2009, in U.S. Appl. No. 10/409,598.
Advisory Action issued Feb. 27, 2009, in U.S. Appl. No. 10/409,598.
Request for Continued Examination filed Mar. 26, 2009, in U.S. Appl. No. 101409,598.
Notice of Allowance and Issue Fee(s) Due issued May 8, 2009, in U.S. Appl. No. 10/409,598.
Restriction Requirement issued Jul. 13, 2005, in U.S. Appl. No. 10/409,611.
Response to Restriction Requirement filed Aug. 11, 2005, in U.S. Appl. No. 10/409,611.
Non-Final Office Action issued Oct. 12, 2005, in U.S. Appl. No. 10/409,611.
1.111 Amendment (with Declaration and Ids) filed Apr. 11, 2006, in U.S. Appl. No. 10/409,611.
Final Office Action issued Jun. 14, 2006, in U.S. Appl. No. 10/409,611.
Notice of Appeal filed Dec. 14, 2006, in U.S. Appl. No. 10/409,611.
Notice of Abandonment issued Jul. 12, 2007, in U.S. Appl. No. 10/409,611.
Request to Withdrawal Abandonment, Request for Continued Examination, 116 Amendment and Information Disclosure Statement filed Jul. 13, 2007, in U.S. Appl. No. 10/409,611.
Communication, Withdrawal of Abandonment issued Jul. 24, 2007, in U.S. Appl. No. 10/409,611.
Decision on Petition issued Dec. 14, 2007, in U.S. Appl. No. 10/409,611.
Non-Final Office Action issued Apr. 21, 2008, in U.S. Appl. No. 10/409,611.
Decision on Petition issued Jul. 9, 2008, in U.S. Appl. No. 10/409,611.
1.111 Amendment filed Jul. 21, 2008, in U.S. Appl. No. 10/409,611.
Supplemental Submission filed Aug. 6, 2008, in U.S. Appl. No. 10/409,611.
Notice of Non-Complaint Amendment issued Nov. 14, 2008, in U.S. Appl. No. 10/409,611.
Response to Notice of Non-Compliant Amendment filed Dec. 15, 2008, in U.S. Appl. No. 10/409,611.
Final Office Action issued Apr. 13, 2009, in U.S. Appl. No. 10/409,611.
Restriction Requirement issued Aug. 22, 2005, in U.S. Appl. No. 10/409,608.
Amendment (Response to Restriction Requirement) filed Nov. 22, 2005, in U.S. Appl. No. 10/409,608.
Restriction Requirement issued Feb. 6, 2006, in U.S. Appl. No. 10/409,608.
Response to Restriction Requirement filed Mar. 27, 2006, in U.S. Appl. No. 10/409,608.
Non-Final Office Action issued May 31, 2006, in U.S. Appl. No. 10/409,608.
1.111 Amendment (with Sequence Listing and IDS) filed Nov. 30, 2006, in U.S. Appl. No. 10/409,608.
Final Office Action issued Feb. 22, 2007, in U.S. Appl. No. 10/409,608.
Notice of Appeal filed Aug. 22, 2007, in U.S. Appl. No. 10/409,608.
Request for Continued Examination and 1.114(c) Amendment filed Mar. 19, 2008, in U.S. Appl. No. 10/409,608.
Non-Final Office Action issued Jun. 6, 2008, in U.S. Appl. No. 10/409,608.
1.111 Amendment filed Sep. 26, 2008, in U.S. Appl. No. 10/409,608.
Final Office Action issued Dec. 31, 2008, in U.S. Appl. No. 10/409,608.
1.116 Amendment filed May 29, 2009, in U.S. Appl. No. 10/409,608.
Advisory Action issued Jun. 3, 2009, in U.S. Appl. No. 10/409,608.
RCE and Terminal Disclaimer filed Jun. 19, 2009, in U.S. Appl. No. 10/409,608.
Non-Final OA issued Oct. 12, 2006 in U.S. Appl. No. 10/803,100.
Non-Final OA issued Apr. 30, 2008 in U.S. Appl. No. 11/783,487.
Non-Final OA issued May 12, 2009 in U.S. Appl. No. 12/261,997.
Restriction Requirement issued Feb. 3, 2009 in U.S. Appl. No. 10/575,261.
Response to Restriction Requirement filed Mar. 3, 2009 in U.S. Appl. No. 10/575,261.
Election of Species Requirement issued May 26, 2009 in U.S. Appl. No. 10/575,261.
Restriction Requirement issued Jun. 20, 2006 in U.S. Appl. No. 10/959,326.
Response to Restriction Requirement filed Jul. 20, 2006 in U.S. Appl. No. 10/959,326.
Supplemental Response to Restriction Requirement and Preliminary Amendment filed Aug. 21, 2006 in U.S. Appl. No. 10/959,326.
Non-Final OA issued Oct. 5, 2006 in U.S. Appl. No. 10/959,326.
Restriction Requirement issued Apr. 8, 2008 in U.S. Appl. No. 11/730,992.
Restriction Requirement issued Oct. 23, 2006 in U.S. Appl. No. 10/959,310.
Response to Restriction Requirement filed Apr. 23, 2007 in U.S. Appl. No. 10/959,310.
Non-Final OA issued Jul. 6, 2007 in U.S. Appl. No. 10/959,310.
Restriction Requirement issued Sep. 14, 2006 in U.S. Appl. No. 10/959,322.
Response to Restriction Requirement filed Oct. 18, 2006 in U.S. Appl. No. 10/959,322.
Non-Final OA issued Mar. 21, 2007 in U.S. Appl. No. 10/959,322.
1.111 Amendment filed Sep. 19, 2007 in U.S. Appl. No. 10/959,322.
Final OA issued Apr. 28, 2008 in U.S. Appl. No. 10/959,322.
1.116 Amendment filed Aug. 28, 2008 in U.S. Appl. No. 10/959,322.
Advisory Action issued Sep. 19, 2008 in U.S. Appl. No. 10/959,322.
RCE and 1.114 Amendment filed Oct. 16, 2008 in U.S. Appl. No. 10/959,322.

Non-Final OA issued Dec. 5, 2008 in U.S. Appl. No. 10/959,322.
1.111 Response filed Apr. 2, 2009 in U.S. Appl. No. 10/959,322.
Restriction Requirement issued Feb. 28, 2007 in U.S. Appl. No. 10/959,309.
Response to Restriction Requirement filed Apr. 2, 2007 in U.S. Appl. No. 10/959,309.
Non-Final OA issued Jun. 14, 2007 in U.S. Appl. No. 10/959,309.
1.111 Amendment filed Dec. 14, 2007 in U.S. Appl. No. 10/959,309.
Final OA issued Apr. 2, 2008 in U.S. Appl. No. 10/959,309.
1.116 Amendment filed Aug. 1, 2008 in U.S. Appl. No. 10/959,309.
Advisory Action issued Aug. 14, 2008 in U.S. Appl. No. 10/959,309.
RCE filed Sep. 2, 2008 in U.S. Appl. No. 10/959,309.
Non-Final OA issued Oct. 10, 2008 in U.S. Appl. No. 10/959,309.
Restriction Requirement issued Jun. 26, 2008 in U.S. Appl. No. 10/575,253.
Response to Restriction Requirement filed Sep. 26, 2008 in U.S. Appl. No. 10/575,253.
Non-Final OA issued Jan. 13, 2009 in U.S. Appl. No. 10/575,253.
Restriction Requirement issued Apr. 1, 2009 in U.S. Appl. No. 10/575,096.
Response to Restriction requirement filed May 29, 2009 in U.S. Appl. No. 10/575,096.
Restriction Requirement issued Jun. 12, 2009 in U.S. Appl. No. 10/575,096.
Restriction Requirement issued Jun. 12, 2007 in U.S. Appl. No. 11/196,503.
Response to Restriction Requirement filed Jul. 12, 2007 in U.S. Appl. No. 11/196,503.
Supplemental Response to Restriction Requirement filed Sep. 6, 2007 in U.S. Appl. No. 11/196,503.
Non-Final OA issued Nov. 13, 2007 in U.S. Appl. No. 11/196,503.
1.111 Amendment filed Feb. 21, 2008 in U.S. Appl. No. 11/196,503.
Final OA issued May 7, 2008 in U.S. Appl. No. 11/196,503.
1.116 Amendment filed Jul. 28, 2008 in U.S. Appl. No. 11/196,503.
Advisory Action issued Aug. 15, 2008 in U.S. Appl. No. 11/196,503.
RCE and 1.114 Amendment filed Sep. 5, 2008 in U.S. Appl. No. 11/196,503.
Non-Final OA issued Oct. 10, 2008 in U.S. Appl. No. 11/196,503.
1.111 Response and Terminal Disclaimer filed Mar. 10, 2009 in U.S. Appl. No. 11/196,503.
Final Office Action issued Jun. 22, 2009, in U.S. Appl. No. 11/196,503.
Restriction Requirement issued Sep. 11, 2007 in U.S. Appl. No. 11/491,501.
Response to Restriction Requirement filed Oct. 11, 2007 in U.S. Appl. No. 11/491,501.
Non-Final Office Action issued Feb. 6, 2008 in U.S. Appl. No. 11/491,501.
1.111 Amendment filed Jul. 7, 2008 in U.S. Appl. No. 11/491,501.
Notice to Comply issued Oct. 28, 2008 in U.S. Appl. No. 11/491,501.
Response to Notice to Comply filed Nov. 13, 2008 in U.S. Appl. No. 11/491,501.
Notice to Comply issued Feb. 25, 2009 in U.S. Appl. No. 11/491,501.
Response to Notice to Comply filed Mar. 18, 2009 in U.S. Appl. No. 11/491,501.
Restriction Requirement issued Jun. 14, 2002 in U.S. Appl. No. 09/796,744.
Response to Restriction Requirement filed Jul. 15, 2002 in U.S. Appl. No. 09/796,744.
Non-Final OA issued Oct. 16, 2002 in U.S. Appl. No. 09/796,744.
1.111 Amendment filed Mar. 17, 2003 in U.S. Appl. No. 09/796,744.
Non-Final OA issued Jun. 2, 2003 in U.S. Appl. No. 09/796,744.
1.111 Amendment and 1.132 Declaration filed Dec. 2, 2003 in U.S. Appl. No. 09/796,744.
Final OA issued Feb. 25, 2004 in U.S. Appl. No. 09/796,744.
1.116 Amendment and 1.132 Declaration filed Jul. 26, 2004 in U.S. Appl. No. 09/796,744.
Advisory Action issued Aug. 24, 2004 in U.S. Appl. No. 09/796,744.
Notice of Appeal filed Aug. 25, 2004 in U.S. Appl. No. 09/796,744.
RCE filed Sep. 7, 2004 in U.S. Appl. No. 09/796,744.
Non-Final OA issued Nov. 5, 2004 in U.S. Appl. No. 09/796,744.
1.111 Amendment filed Nov. 30, 2004 in U.S. Appl. No. 09/796,744.
Notice of Allowance issued Feb. 22, 2005 in U.S. Appl. No. 09/796,744.
Restriction Requirement issued Feb. 6, 2007 in U.S. Appl. No. 11/094,718.
Response to Restriction Requirement filed Mar. 16, 2007 in U.S. Appl. No. 11/094,718.
Non-Final OA issued May 30, 2007 in U.S. Appl. No. 11/094,718.
1.111 Amendment filed Oct. 29, 2007 in U.S. Appl. No. 11/094,718.
Final OA issued Dec. 21, 2007 in U.S. Appl. No. 11/094,718.
1.116 Amendment filed May 21, 2008 in U.S. Appl. No. 11/094,718.
Advisory Action issued Jun. 13, 2008 in U.S. Appl. No. 11/094,718.
RCE filed Jun. 20, 2008 in U.S. Appl. No. 11/094,718.
Non-Final OA issued Sep. 16, 2008 in U.S. Appl. No. 11/094,718.
1.111 Amendment filed Dec. 16, 2008 in U.S. Appl. No. 11/094,718.
Final OA issued Mar. 13, 2009 in U.S. Appl. No. 11/094,718.
1.116 Amendment filed Jun. 15, 2009 in U.S. Appl. No. 11/094,718.
Advisory Action issued Jun. 24, 2009 in U.S. Appl. No. 11/094,718.
RCE filed Jul. 13, 2009 in U.S. Appl. No. 11/094,718.
Restriction Requirement issued Jul. 12, 2005 in U.S. Appl. No. 10/231,452.
Response to Restriction Requirement filed Aug. 12, 2005 in U.S. Appl. No. 10/231,452.
Notice of Non-Compliant Response issued Sep. 28, 2005 in U.S. Appl. No. 10/231,452.
Response to Notice of Non-Compliant Response filed Oct. 25, 2005 in U.S. Appl. No. 10/231,452.
Non-Final OA issued Jan. 10, 2006 in U.S. Appl. No. 10/231,452.
1.111 Amendment filed Jul. 13, 2006 in U.S. Appl. No. 10/231,452.
Final OA issued Sep. 21, 2006 in U.S. Appl. No. 10/231,452.
Notice of Appeal filed Mar. 21, 2007 in U.S. Appl. No. 10/231,452.
1.116 Amendment and Terminal Disclaimer filed Apr. 5, 2007 in U.S. Appl. No. 10/231,452.
Advisory Action issued Apr. 24, 2007 in U.S. Appl. No. 10/231,452.
RCE filed May 21, 2007 in U.S. Appl. No. 10/231,452.
Non-Final OA issued Jul. 31, 2007 in U.S. Appl. No. 10/231,452.
Petition to Withdraw Terminal Disclaimer of Apr. 5, 2007 filed Oct. 31, 2007 in U.S. Appl. No. 10/231,452.
1.111 Amendment filed Nov. 30, 2007 in U.S. Appl. No. 10/231,452.
Decision on Petition issued on Jan. 3, 2008 in U.S. Appl. No. 10/231,452.
Final OA issued Feb. 20, 2008 in U.S. Appl. No. 10/231,452.
1.116 Amendment filed Jun. 20, 2008 in U.S. Appl. No. 10/231,452.
Advisory Action issued Aug. 5, 2008 in U.S. Appl. No. 10/231,452.
RCE and 1.114 Amendment filed Aug. 20, 2008 in U.S. Appl. No. 10/231,452.
Notice of Allowance issued Nov. 10, 2008 in U.S. Appl. No. 10/231,452.
Restriction Requirement issued Jan. 19, 2007 in U.S. Appl. No. 11/144,731.
Response to Restriction Requirement filed Feb. 12, 2007 in U.S. Appl. No. 11/144,731.
Non-Final OA issued Mar. 19, 2007 in U.S. Appl. No. 11/144,731.
1.111 Amendment filed Sep. 5, 2007 in U.S. Appl. No. 11/144,731.
Final OA issued Nov. 13, 2007 in U.S. Appl. No. 11/144,731.
RCE and 1.114 Amendment filed May 8, 2008 in U.S. Appl. No. 11/144,731.
Final OA issued May 29, 2008 in U.S. Appl. No. 11/144,731.
1.116 Amendment filed Sep. 29, 2008 in U.S. Appl. No. 11/144,731.
Advisory Action issued Oct. 15, 2008 in U.S. Appl. No. 11/144,731.
Pre-Appeal Brief Request for Review and Notice of Appeal filed Dec. 1, 2008 in U.S. Appl. No. 11/144,731.
Notice of Panel Decision issued Jan. 13, 2009 in U.S. Appl. No. 11/144,731.
RCE filed Feb. 13, 2009 in U.S. Appl. No. 11/144,731.
Notice of Non-Response Amendment issued Jun. 4, 2009 in U.S. Appl. No. 11/144,731.
Restriction Requirement issued Jul. 13, 2007 in U.S. Appl. No. 10/581,413.
Response to Restriction Requirement filed Aug. 27, 2007 in U.S. Appl. No. 10/581,413.

Non-Final OA issued Oct. 17, 2007 in U.S. Appl. No. 10/581,413.
1.111 Amendment filed Apr. 17, 2008 in U.S. Appl. No. 10/581,413.
Restriction Requirement issued Jul. 28, 2008 in U.S. Appl. No. 10/581,413.
Response to Restriction Requirement filed Aug. 28, 2008 in U.S. Appl. No. 10/581,413.
Final OA issued Dec. 11, 2008 in U.S. Appl. No. 10/581,413.
1.116 Amendment and Statement of Availability filed Apr. 13, 2009 in U.S. Appl. No. 10/581,413.
Advisory Action issued Apr. 27, 2009 in U.S. Appl. No. 10/581,413.
RCE filed May 11, 2009 in U.S. Appl. No. 10/581,413.
Restriction Requirement issued Apr. 25, 2008 in U.S. Appl. No. 10/574,016.
Response to Restriction Requirement filed May 27, 2008 in U.S. Appl. No. 10/574,016.
Non-Final OA issued Aug. 4, 2008 in U.S. Appl. No. 10/574,016.
1.111 Amendment filed Nov. 4, 2008 in U.S. Appl. No. 10/574,016.
Non-Final OA issued Jan. 30, 2009 in U.S. Appl. No. 10/574,016.
1.111 Amendment and Rule 1.132 Declaration filed May 29, 2009 in U.S. Appl. No. 10/574,016.
Restriction Requirement issued Mar. 27, 2009 in U.S. Appl. No. 12/019,160.
Response to Restriction Requirement filed Apr. 27, 2009 in U.S. Appl. No. 12/019,160.
Non-Final Office Action issued Jun. 24, 2009, in U.S. Appl. No. 12/019,160.
Rothman, et at , "Antibody-Dependent Cytotoxicity Mediated by Natural Killer Cells is Enhanced by Castanospermine-Induced Alterations of IgG Glycosylation", Molecular Immunology, vol. 26 No. 12, pp. 1113-1123, 1989.
Umana et al., Engineered Glycoforms of an Antineuroblastoma IgG1 with Optimized Antibody-dependent Cellular Cytotoxic Activity, Nature Biotechnology, vol, 17 Feb., 1999 pp. 176-180.
Simonson., et al., Inhibition of Mannosidase in Hybridomas Yields Monoclonal Antibodies with Greater Capacity for Carbohydrate Labeling, Clinical Chemistry, vol. 34, No. 9, 1988 pp. 1713-1716.
EPO letter re: Observations according to Article 115 and Rule 114 EPC, dated Jul. 8, 2009.
Communication Pursuant to Rule 114 (2) EPC, dated Jul. 21, 2009.
RCE filed Jul. 18, 2009, in U.S. Appl. No. 11/686,379.
RCE filed Jul. 18, 2009, in U.S. Appl. No. 11/686,391.
RCE filed Jul. 18, 2009, in U.S. Appl. No. 11/686,404.
RCE filed Jul. 19, 2009, in U.S. Appl. No. 11/686,458.
RCE filed Jul. 20, 2009, in U.S. Appl. No. 11/686,906.
RCE filed Jul. 17, 2009, in U.S. Appl. No. 11/686,911.
RCE filed Jul. 18, 2009, in U.S. Appl. No. 11/686,920.
Final Office Action issued Jul. 24, 2009, in U.S. Appl. No. 11/240,579.
Request for Continued Examination filed Jul. 29, 2009, in U.S. Appl. No. 10/409,598.
Response to Election of Species Requirement and Preliminary Amendment filed Jun. 25, 2009 in U.S. Appl. No. 10/575,261.
Notice of Allowance issued Jul. 23, 2009, in U.S. Appl. No. 10/959,322.
RCE filed Jul. 13, 2009 in U.S. Appl. No. 11/094,718.
Non-Final Office Action issued Jul. 22, 2009, in U.S. Appl. No. 10/581,413.
Restriction Requirement issued Jul. 12, 2009, in U.S. Appl. No. 10/575,114.

* cited by examiner

FIG.1
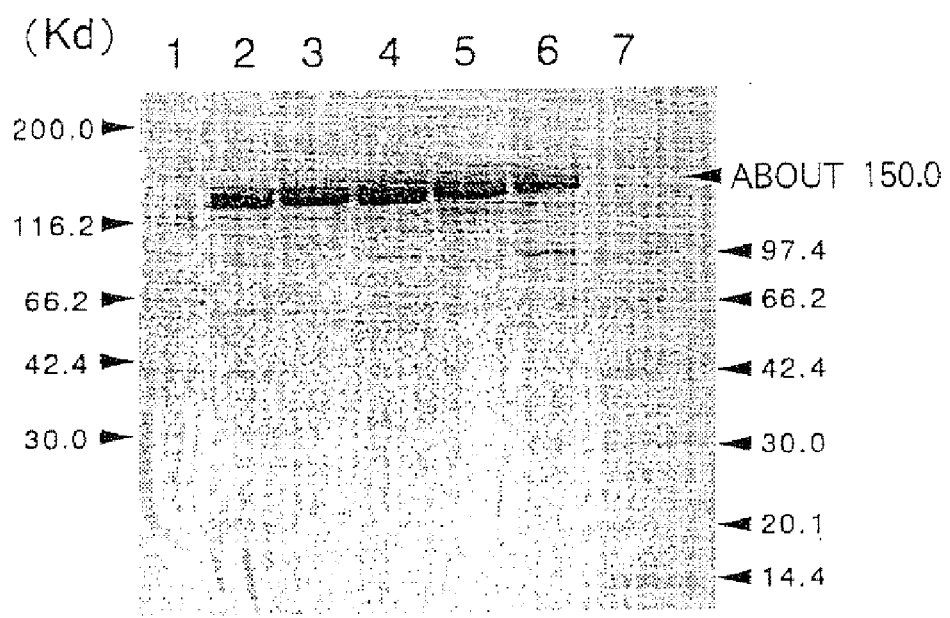
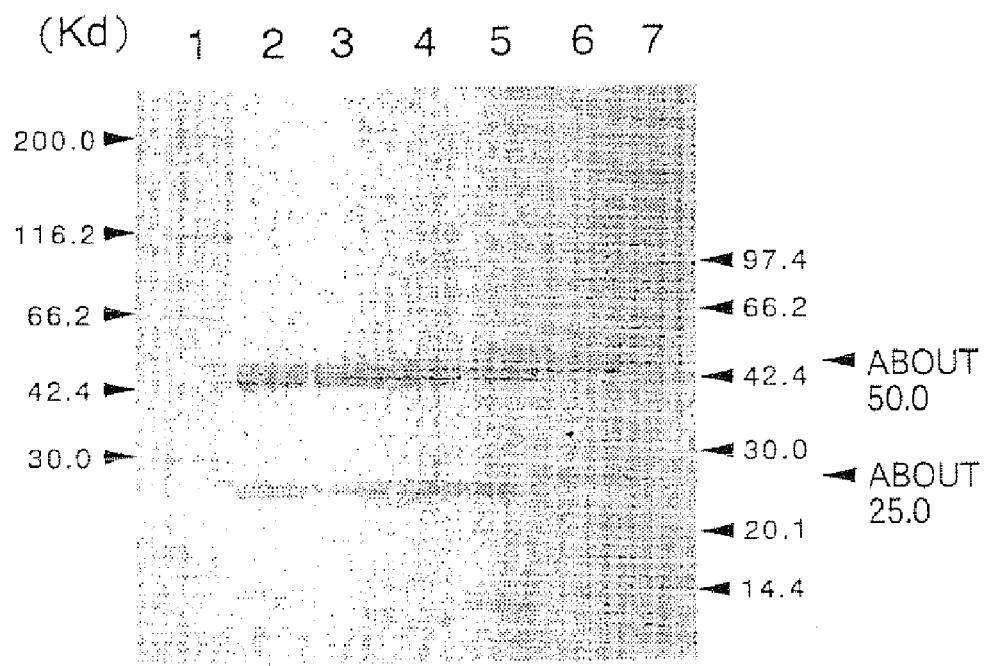

FIG.4
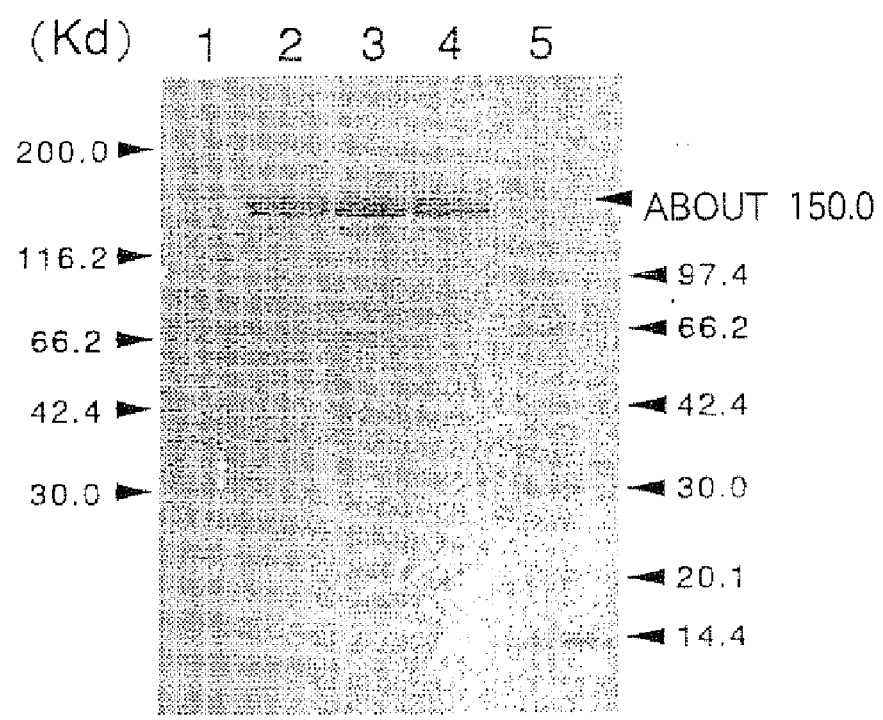
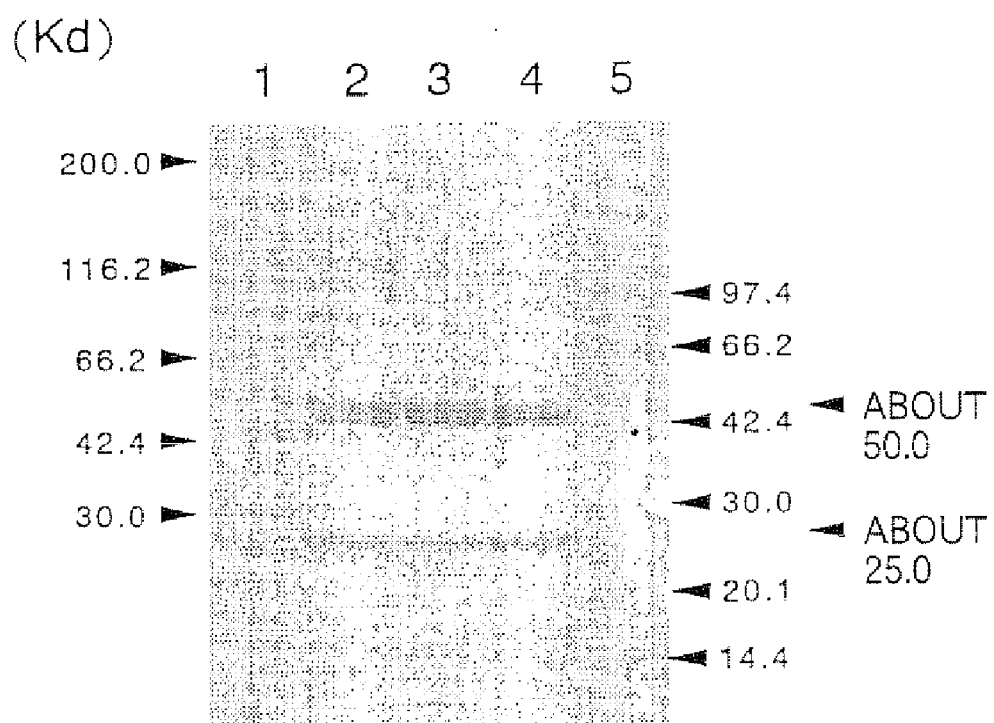

FIG.8
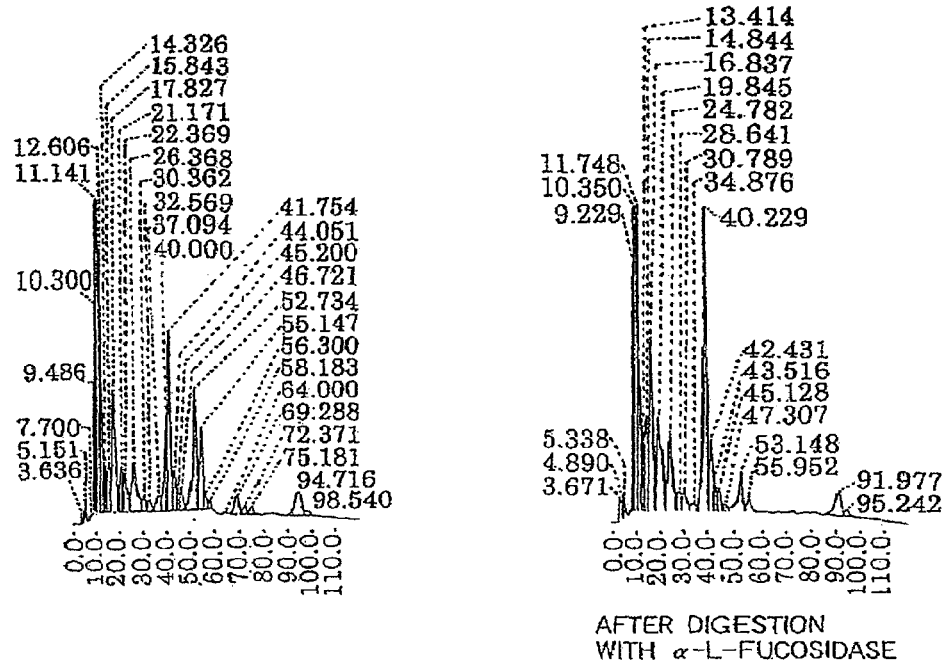
YB2/0-hIL-5RCDR ANTIBODY
AFTER DIGESTION WITH α-L-FUCOSIDASE
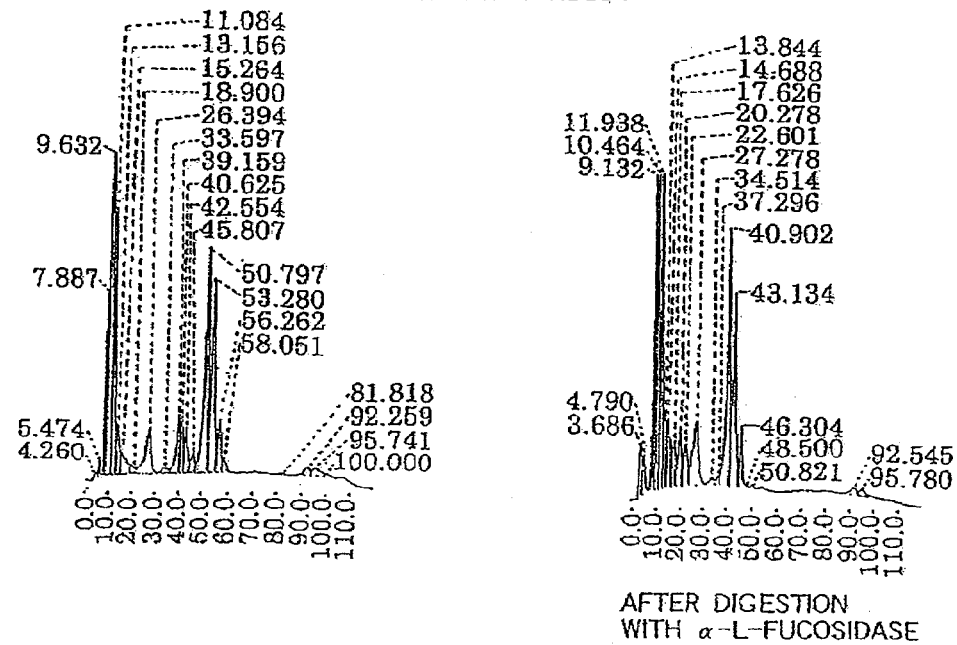
NS0-hIL-5RCDR ANTIBODY
AFTER DIGESTION WITH α-L-FUCOSIDASE

FIG.10
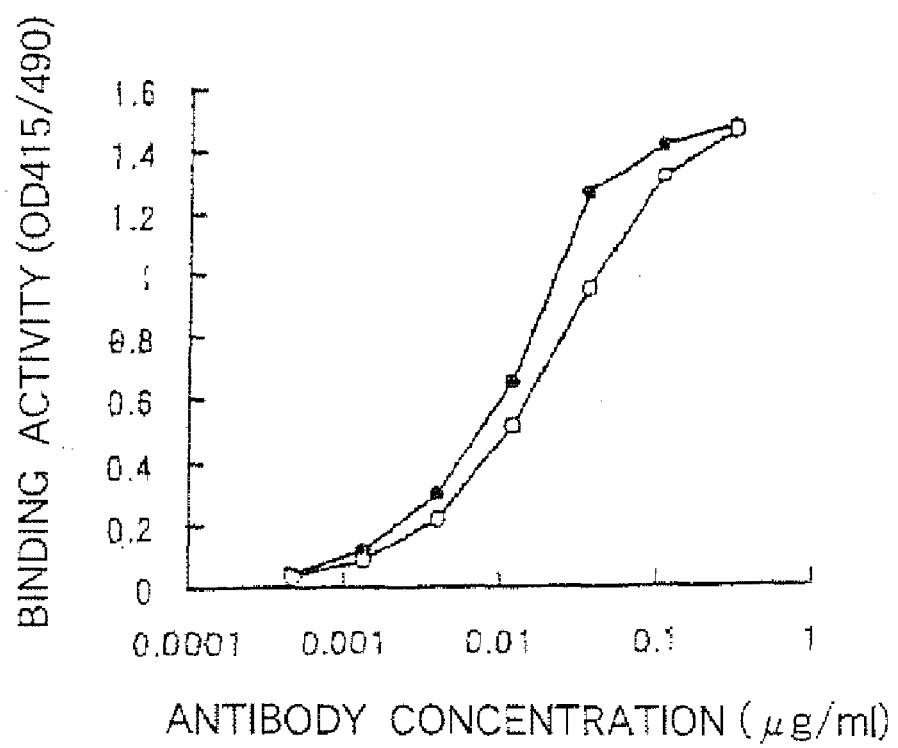
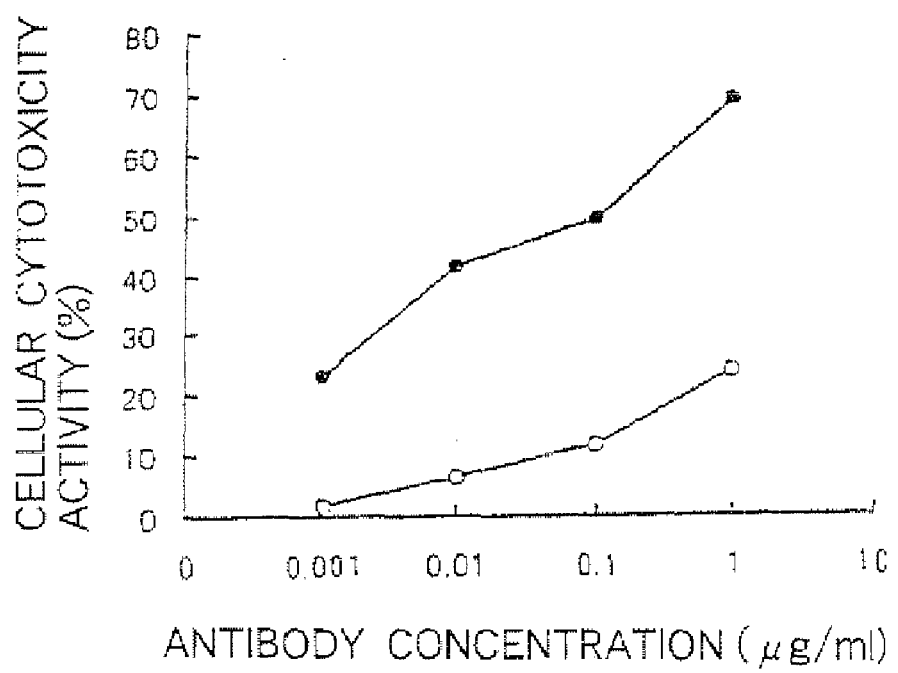

SEQUENCE LISTING

<160> NUMBER OF SEQ ID NOS: 13

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequense : Synthetic DNA end.

<400> SEQUENCE: 1

```
actcatcttg gaatctcaga attgg                                         25

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequense : Synthetic
      DNA end.

<400> SEQUENCE: 2
cttgaccgtt tctatcttct ctcg                                          24

<210> SEQ ID NO 3
<211> LENGTH: 979
<212> TYPE: DNA
<213> ORGANISM: Cricetulus griseus
<220> FEATURE:

<400> SEQUENCE: 3
actcatcttg gaatctcaga attggcgcta tgctactgga ggatgggaga ctgtgtttag    60
acctgtaagt gagacatgca cagacaggtc tggcctctcc actggacact ggtcaggtga   120
agtgaaggac aaaaatgttc aagtggtcga gctccccatt gtagacagcc tccatcctcg   180
tcctccttac ttacccttgg ctgtaccaga agaccttgca gatcgactcc tgagagtcca   240
tggtgatcct gcagtgtggt gggtatccca gtttgtcaaa tacttgatcc gtccacaacc   300
ttggctggaa agggaaatag aagaaccac caagaagctt ggcttcaaac atccagttat   360
tggagtccat gtcagacgca ctgacaaagt gggaacagaa gcagccttcc atcccattga   420
ggaatacatg gtacacgttg aagaacattt tcagcttctc gaacgcagaa tgaaagtgga   480 taaaaaaga gtgtatctgg ccactgatga cccttctttg ttaaaggagg caaagacaaa   540
gtactccaat tatgaattta ttagtgataa ctctatttct tggtcagctg gactacacaa   600
ccgatacaca gaaaattcac ttcggggcgt gatcctggat atacactttc tctcccaggc   660
tgacttcctt gtgtgtactt tttcatccca ggtctgtagg gttgcttatg aaatcatgca   720
aacactgcat cctgatgcct ctgcaaactt ccattcttta gatgacatct actattttgg   780
aggccaaaat gccacaaacc agattgcagt ttatcctcac caacctcgaa ctaaagagga   840
aatccccatg gaacctggag atatcattgg tgtggctgga aaccattgga atggttactc   900
taaaggtgtc aacagaaaac taggaaaaac aggcctgtac ccttcctaca aagtccgaga   960
gaagatagaa acggtcaag                                               979

<210> SEQ ID NO 4
<211> LENGTH: 979
<212> TYPE: DNA
<213> ORGANISM: Rattus
<220> FEATURE:

<400> SEQUENCE: 4
actcatcttg gaatctcaga attggcgcta tgctactggt ggatgggaga ctgtgtttag    60
acctgtaagt gagacatgca cagacagatc tggcctctcc actggacact ggtcaggtga   120
agtgaatgac aaaaatattc aagtggtgga gctccccatt gtagacagcc ttcatcctcg   180
gcctccttac ttaccactgg ctgttccaga agaccttgca gatcgactcg taagagtcca   240
tggtgatcct gcagtgtggt gggtgtccca gttcgtcaaa tatttgattc gtccacaacc   300
ttggctagaa aaggaaatag aagaagccac caagaagctt ggcttcaaac atccagtcat   360
```

-continued

```
tggagtccat gtcagacgca cagacaaagt gggaacagag gcagccttcc atcccatcga    420
agagtacatg gtacatgttg aagaacattt tcagcttctc gcacgcagaa tgcaagtgga    480 taaaaaaga gtatatctgg ctaccgatga ccctgctttg ttaaaggagg caaagacaaa     540
gtactccaat tatgaattta ttagtgataa ctctatttct tggtcagctg gactacacaa    600
tcggtacaca gaaaattcac ttcggggcgt gatcctggat atacactttc tctctcaggc    660
tgacttccta gtgtgtactt tttcatccca ggtctgtcgg gttgcttatg aaatcatgca    720
aaccctgcat cctgatgcct ctgcaaactt ccactcttta gatgacatct actattttgg    780
aggccaaaat gcccacaacc agattgccgt ttatcctcac aaacctcgaa ctgatgagga    840
aattccaatg gaacctggag atatcattgg tgtggctgga aaccattggg atggttattc    900
taaaggtgtc aacagaaaac ttggaaaaac aggcttatat ccctcctaca aagtccgaga    960
gaagatagaa acggtcaag                                                 979
```

```
<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequense : Synthetic
      DNA end.

<400> SEQUENCE: 5
aagtataagc ttacatggat gacgatatcg ctgcgctcgt                          40
```

```
<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequense : Synthetic
      DNA end.

<400> SEQUENCE: 6
atttaactgc aggaagcatt tgcggtggac gatggagggg                          40
```

```
<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequense : Synthetic
      DNA end.

<400> SEQUENCE: 7
atttaaggta ccgaagcatt tgcggtgcac gatggagggg                          40
```

```
<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequense : Synthetic
      DNA end.

<400> SEQUENCE: 8
gtccatggtg atcctgcagt gtgg                                           24
```

```
<210> SEQ ID NO 9
<211> LENGTH: 23
<212> TYPE: DNA
```

```
<213> ORGANISM: Artificial Sequence
<220> FEATURE:
<223> OTHER INFORMATION: Description of Artificial Sequense : Synthetic
      DNA end.

<400> SEQUENCE: 9
caccaatgat atctccaggt tcc                                              23

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequense : Synthetic
      DNA end.

<400> SEQUENCE: 10
gatatcgctg cgctcgttgt cgac                                             24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequense : Synthetic
      DNA end.

<400> SEQUENCE: 11
caggaaggaa ggctggaaaa gagc                                             24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequense : Synthetic
      DNA end.

<400> SEQUENCE: 12
gatatcgctg cgctcgtcgt cgac                                             24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequense : Synthetic
      DNA end.

<400> SEQUENCE: 13
caggaaggaa ggctggaaga gagc                                             24
```

METHOD OF MODULATING THE ACTIVITY OF FUNCTIONAL IMMUNE MOLECULES TO CD52

SPECIFICATION

The present application is a divisional of U.S. Ser. No. 11/126,176, filed May 11, 2005 (now U.S. Pat. No. 7,214, 775), which is a divisional of U.S. Ser. No. 09/958,307, filed Oct. 9, 2001 (abandoned), which is a 371 U.S. national phase of PCT/JP00/02260, filed Apr. 7, 2000, which claims benefit of JP 11-103158, filed Apr. 9, 1999, the entire contents of each of which is hereby incorporated by reference.

TECHNICAL FIELD

The present invention relates to a method for controlling the activity of an immunologically functional molecule, such as an antibody, a protein, a peptide or the like, an agent of promoting the activity of an immunologically functional molecule, and an immunologically functional molecule having the promoted activity.

BACKGROUND ART

Since antibodies have high binding activity, binding specificity and high stability in blood, their applications to the diagnosis, prevention and treatment of various human diseases have been attempted (*Monoclonal Antibodies: Principles and Applications*, Wiley-Liss, Inc., Chapter 2.1 (1995)). However, an antibody derived from an animal other than human, such as a mouse antibody, is recognized as a foreign material when administered to a human, which thereby induces a human antibody against the mouse antibody (human anti mouse antibody: hereinafter referred to as "HAMA") in the human body, and it is known that the HAMA causes side effects by reaction with the administered mouse antibody (*J. Clin. Oncol.*, 2, 881 (1984); *Blood*, 65, 1349 (1985); *J. Natl. Cancer Inst.*, 80, 932 (1988); *Proc. Natl. Acad. Sci. U.S.A.*, 82, 1242 (1985)), promotes disappearance of the administered mouse antibody from blood (*J. Nuc. Med.* 26, 1011 (1985); *Blood*, 65, 1349 (1985); *J. Natl. Cancer Inst.*, 80, 937 (1988)) and reduces diagnostic, preventive and therapeutic effects of the mouse antibody (*J. Immunol.*, 135, 1530 (1985); *Cancer Res.*, 46, 6489 (1936)).

For the purpose of solving these problems, attempts have been made to convert an antibody derived from an animal other than human into a humanized antibody, such as a human chimeric antibody or a human complementarity determining region (hereinafter referred to as "CDR")-grafted antibody, using gene recombination techniques. The human chimeric antibody is an antibody in which its antibody variable region (hereinafter referred to as "V region") is of an antibody of an animal other than human and its constant region (hereinafter referred to as "C region") is of a human antibody (*Proc. Natl. Acad. Sci. U.S.A.*, 81, 6851 (1984)). It has been reported that administration of such chimeric antibodies to humans eliminate serious side effects and the half-life in blood was prolonged about 6 times compared to a mouse antibody (*Proc. Natl. Acad. Sci. U.S.A.*, 86, 4220 (1989)). The human CDR-grafted antibody is an antibody in which CDR of a human antibody is replaced by CDR of an antibody other than human (*Nature*, 321, 522 (1986)). It has been reported that, in an experimentation using monkey, the immunogenicity of a human CDR-grafted antibody was reduced and its half-life in blood was prolonged 4 to 5 times compared to a mouse antibody (*J. Immunol.*, 147, 1352 (1991)). These reports show that a humanized antibody is expected to have sufficient effects, as an antibody to be applied to the diagnosis, prevention and treatment of various human diseases, even though it is not a completely human antibody. Actually, clinical tests have been performed with anti-tumor antibodies, such as an anti-CD20 human chimeric antibody, Rituxan (IDEC, Inc.), and an anti-HER2/neu human CDR-grafted antibody, Herceptin (Genentech, Inc.). The safety and therapeutic effects of the anti-CD20 human chimeric antibody and of the anti-HER2/neu human CDR-grafted antibody, to a certain degree, have been confirmed in B lymphoma and breast cancer, respectively (*J. Clin. Oncol.*, 16, 2825 (1998); *J. National Cancer Institute*, 90, 882 (1998)). Moreover, a fragment (Fab') of an anti-GPIIb/IIIa human chimeric antibody, ReoPro (Centocor, Inc.), is commercially available in Europe and America as a secondary disease preventing drug after percutaneous transluminal coronary angioplasty. Currently, a large number of clinical tests are being conducted with other humanized antibodies. Most of these humanized antibodies have been prepared using gene recombination techniques and produced using appropriate animal cells.

It has been revealed that five classes of antibodies, i.e., IgM, IgD, IgG, IgA and IgE, are present in mammals. Antibodies of human IgG class are mainly used in the diagnosis, prevention and treatment of various human diseases because of their long half-life in blood and functional characteristics, such as various effector functions and the like (*Monoclonal Antibodies: Principles and Applications*, Wiley-Liss, Inc., Chapter 2.1 (1995)). The human IgG class antibody is further classified into the following 4 subclasses: IgG1, IgG2, IgG3 and IgG4. A large number of studies have so far been carried out for the antibody-dependent cellular cytotoxicity activity (hereinafter referred to as "ADCC activity") and complement-dependent cytotoxicity activity (hereinafter referred to as "CDC") as effector functions of the IgG class antibody, and it has been reported that antibodies of the IgG1 subclass have the greatest ADCC activity and CDC activity among the human IgG class antibodies (*Chemical Immunology*, 65, 88 (1997)). Therefore, most of the anti-tumor humanized antibodies which require a high effector function are antibodies of human IgG1 subclass, including the above Rituxan and Herceptin.

Expression of ADCC activity and CDC activity of human IgG1 subclass antibodies requires binding of the Fc region of antibody to an antibody receptor existing on the surface of an effector cell, such as a killer cell, a natural killer cell, an activated macrophage or the like (hereinafter referred to as "FcγR") and various complement components. It has been suggested that several amino acid residues in the second domain of the antibody hinge region and C region (hereinafter referred to as "Cγ2 domain") (*Eur. J. Immunol.*, 23, 1098 (1993), *Immunology*, 86, 319 (1995), *Chemical Immunology*, 65, 88 (1997)) and a sugar chain linked to the Cγ2 domain are also important for this binding reaction (*Chemical Immunology*, 65, 88 (1997)). Regarding the sugar chain, Boyd et al. have examined effects of a sugar chain on the ADCC activity and CDC activity, by treating a human CDR-grafted antibody, CAMPATH-1H (human IgG1 subclass), produced using Chinese hamster ovary cell (CHO cell) or mouse myeloma NS0 cell with various sugar hydrolyzing enzymes, and reported that elimination of sialic acid of the non-reducing terminal does not have influence upon both activities. Further elimination of galactose residue however was reported to exert influence upon only the CDC activity, decreasing about 50% of its activity. Complete elimination of the sugar chain was reported to cause disappearance of both activities (*Molecular Immunol.*, 32, 1311 (1995)). Moreover, Lifely et al. have analyzed the sugar chain of a human CDR-grafted antibody, CAMPATH-1H (human IgG1 subclass) which was produced using CHO cell, NS0 cell or rat myeloma YO cell, measured its ADCC activity and reported that the CAMPATH-1H derived from YO cell shows the greatest ADCC activity, suggesting that N-acetylglucosamine at the bisecting position is important for the activity (*Glycobiology*, 5, 813 (1995): WO 99/54342). These reports show that the structure of sugar chain plays an important role in the effector function of human IgG1 subclass antibodies, and that it may be possible to prepare an antibody having greater effector function by changing the sugar chain structure. Actually, however, structures of sugar chains are complex and vary greatly. There exists a need therefore to further study the structure in order to obtain greater effector function.

DISCLOSURE OF THE INVENTION

An object of the present invention is to specify a sugar chain which increases the ADCC activity, by analyzing sugar chains of human IgG1 subclass antibodies produced by various animal cells, and to thereby also provide a method for controlling the activity of an immunologically functional molecule. Since the ADCC activity is improved in such antibodies, increase in the therapeutic effect for various human diseases can be expected by use of not only anti-tumor antibodies but also anti-other diseases antibodies, as well as proteins or peptides against various diseases. Particularly, in the clinical application of anti-tumor antibodies, the anti-tumor effect of an antibody alone is insufficient in many of current cases. The insufficiencies of known antibodies have required the concomitant use of chemotherapy (*Science*, 280, 1197, 1998). The dependency on chemotherapy however will be reduced, with a reduction of side effects, it a stronger anti-tumor effect of an antibody alone is provided by the improvement of ADCC activity. The present inventors have evaluated in vitro activity of various humanized antibodies of human IgG1 subclass produced by two kinds of Chinese hamster ovary cells, CHO/dhFr cell (ATCC CRL 9096) and CHO/DG44 cell (*Somatic Cell and Molecular Genetics*, 12, 555 (1986)), mouse myeloma NS0 cell (RCB 0213, *BIO/TECH-NOLOGY*, 10, 169 (1992)), mouse myeloma SP2/0-Ag14 cell (hereinafter referred to as "SP2/0 cell"; ATCC CRL 1581) and rat myeloma YB2/3HL.P2.G11.16Ag.20 cell (hereinafter referred to as "YB2/0 cell"; ATCC CRL 1662) and have discovered, as a result, that the ADCC activity of a humanized antibody produced by the rat myeloma YB2/0 cell is considerably higher than that of the humanized antibodies produced by other cells. Further, as a result of an in vivo activity evaluation using *Macaca faseicularis*, it has been discovered that the humanized antibody produced by YB2/0 cell shows the greatest effect, suggesting the utility of an antibody having elevated ADCC activity in a human clinical application. In addition, a sugar chain having the ability to increase the ADCC activity has been identified by analyzing and comparing structures of the sugar chains of humanized antibodies produced by various animal cells in detail, and the present invention has been accomplished.

More specifically, the present invention relates to the following (1) to (62).

(1) A method for controlling the activity of an immunologically functional molecule, which comprises regulating the presence or absence of binding of fucose to N-acetylglucosamine of the reducing terminal of an N-glycoside-linked sugar chain which binds to the immunologically functional molecule.

(2) The method according to (1), wherein the N-glycoside-linked sugar chain which binds to the immunologically functional molecule comprises:

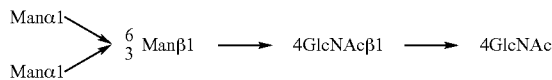

(3) A method for enhancing the activity of an immunologically functional molecule, which comprises binding a sugar chain in which fucose is not present in N-acetylglucosamine of the reducing terminal of an N-glycoside-linked sugar chain to the immunologically functional molecule.

(4) The method according to (3), wherein the sugar chain comprises:

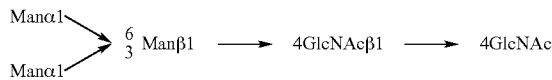

(5) The method according to (3), wherein the sugar chain is synthesized in a cell which has a low enzyme activity of adding fucose to N-acetylglucosamine of the reducing terminal or does not have said enzyme activity.

(6) The method according to (5), wherein the enzyme which adds fucose to N-acetylglucosamine of the reducing terminal is a fucosyltransferase.

(7) The method according to (6), wherein the fucosyltransferase is α1,6-fucosyltransferase.

(8) The method according to (3), wherein the sugar chain is synthesized in a rat myeloma cell.

(9) The method according to (8), wherein the rat myeloma cell is YB2/3HL.P2.G11.16Ag.20 cell (ATCC CRL 1662).

(10) A method for inhibiting the activity of an immunologically functional molecule, which comprises binding a sugar chain in which fucose is present in N-acetylglucosamine of the reducing terminal of an N-glycoside-linked sugar chain to an immunologically functional molecule.

(11) The method according to (10), wherein the sugar chain comprises:

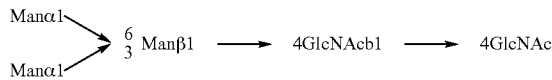

(12) The method according to (10), wherein the sugar chain is synthesized in a cell which has a high enzyme activity of adding fucose to N-acetylglucosamine of the reducing terminal.

(13) The method according to (12), wherein the enzyme which adds fucose to N-acetylglucosamine of the reducing terminal is a fucosyltransferase.

(14) The method according to (13), wherein the fucosyltransferase is α1,6-fucosyltransferase.

(15) The method according to (1) to (14), wherein the immunologically functional molecule is an antibody, a protein or a peptide.

(16) An agent of promoting the activity of an immunologically functional molecule, comprising a sugar chain in which fucose is not present in N-acetylglucosamine of the reducing terminal of an N-glycoside-linked sugar chain.

(17) The agent of promoting the activity of an immunologically functional molecule according to (16), wherein the sugar chain comprises:

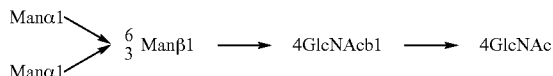

(18) The agent of promoting the activity of an immunologically functional molecule according to (16), wherein the sugar chain is synthesized in a cell which has a low enzyme activity of adding fucose to N-acetylglucosamine of the reducing terminal or does not have said enzyme activity.

(19) The agent of promoting the activity of an immunologically functional molecule according to (18), wherein the enzyme which adds fucose to N-acetylglucosamine of the reducing terminal is a fucosyltransferase.

(20) The agent of promoting the activity of an immunologically functional molecule according to (19), wherein the fucosyltransferase is α1,6-fucosyltransferase.

(21) The agent of promoting the activity of an immunologically functional molecule according to (16), wherein the sugar chain is synthesized in a rat myeloma cell.

(22) The agent of promoting the activity of an immunologically functional molecule according to (21), wherein the rat myeloma cell is YB2/3HL.P2.G11.16Ag.20 cell (ATCC CRL 1662).

(23) The agent of promoting the activity of an immunologically functional molecule according to any one of (16) to (22), wherein the immunologically functional molecule is an antibody, a protein or a peptide.

(24) An immunologically functional molecule having a promoted immunologically functional activity, to which molecule a sugar chain in which fucose is not present in N-acetylglucosamine of the reducing terminal of an N-glycoside-linked sugar chain is bound.

(25) An immunologically functional molecule having an inhibited immunologically functional activity, to which molecule a sugar chain in which fucose is present in N-acetylglucosamine of the reducing terminal of an N-glycoside-linked sugar chain is bound.

(26) The immunologically functional molecule according to (24), wherein the immunologically functional molecule is an antibody, a protein or a peptide.

(27) The immunologically functional molecule according to (25), wherein the immunologically functional molecule is an antibody, a protein or a peptide.

(28) A method for producing the immunologically functional molecule according to (24), which comprises using a cell which has a low enzyme activity of adding fucose to N-acetylglucosamine of the reducing terminal or does not have said enzyme activity.

(29) The method according to (28), wherein the enzyme which adds fucose to N-acetylglucosamine of the reducing terminal is a fucosyltransferase.

(30) The method according to (29), wherein the fucosyltransferase is α1,6-fucosyltransferase.

(31) A method for producing the immunologically functional molecule according to (24), wherein a rat myeloma cell is used in the method for producing an immunologically functional molecule having a promoted immunologically functional activity.

(32) The method according to (31), wherein the rat myeloma cell is YB2/3HL.P2.G11.16Ag.20 cell.

(33) A method for producing the immunologically functional molecule according to (25), wherein a cell having a high enzyme activity of adding fucose to N-acetylglucosamine of the reducing terminal is used.

(34) The method according to (33), wherein the enzyme which adds fucose to N-acetylglucosamine of the reducing terminal is a fucosyltransferase.

(35) The method according to (34), wherein the fucosyltransferase is α1, 6-fucosyltransferase.

(36) The immunologically functional molecule according to (26), wherein the antibody recognizes a tumor-related antigen.

A tumor-related antigen of the present invention is an antigen which is expressed in a tumor cell in greater amount in comparison with normal cells. Examples include ganglioside GD2, GD3 and GM2 (*Cancer Immunol. Immunother.*, 43, 152 (1996)), HER2 (*J. Surgical Research*, 77, 85 (1998)), CD52 (*Leukemia Research*, 22, 185 (1998)), MAGE (*APMIS*, 106, 665 (1998)) and the like. In addition, a factor which induces growth of a tumor cell and its receptor are also tumor-related antigens. Examples include a basic fibroblast growth factor and its receptor (*Pancreas*, 17, 169 (1998)), a vascular endothelial cell growth factor and its receptor (*Pathology International*, 48, 499 (1998)) and the like.

(37) The immunologically functional molecule according to (36), wherein the tumor-related antigen is ganglioside GD3.

(38) The immunologically functional molecule according to (36), wherein the antibody is produced by 7-9-51 (FERM BP-6691).

(39) The immunologically functional molecule according to (26), wherein the antibody recognizes an antigen related to an allergy or inflammation.

An antigen related to an allergy or inflammation according to the present invention is an antigen which induces an allergy or inflammation and an antigen which is induced accompanied by an allergy or inflammation. Examples include interleukin 5 and its receptor (*International Archives. Allergy. Immunol.*, 117, 11 (1998)), a tumor necrosis factor and its receptor (*Cytokine*, 8, 651 (1996)) and the like.

(40) The immunologically functional molecule according to (39), wherein the antigen related to an allergy or inflammation is human interleukin 5 receptor α chain.

(41) The immunologically functional molecule according to (39), wherein the antibody is produced by No. 3 (FERM BP-6690).

(42) The immunologically functional molecule according to (26), wherein the antibody recognizes an antigen related to a cardiovascular disease.

An antigen related to a cardiovascular disease according to the present invention is an antigen which is concerned in a cardiovascular disease induced by thrombus, vascular re-stricture or the like. Examples include platelet GpIIb/IIIa (*Thrombosis Research*, 89, 129 (1998)), a platelet-derived growth factor and its receptor (*American J. Physiology*, 269, 1641 (1995)), a blood coagulation factor (*Thrombosis. Haemostasis*, 79, 14 (1998)) and the like.

(43) The immunologically functional molecule according to (27), wherein the antibody recognizes an antigen related to an autoimmune disease, An antigen related to an autoimmune disease according to the present invention is an autoantigen which induces an immune response as the cause of a disease and an antigen that enhances the response. Examples include auto-DNA (*Rheumatology International*, 17, 223 (1998)), CD4 (*Rheumatic Diseases Clinics. North America*, 24, 567 (1998)) and the like.

(44) The immunologically functional molecule according to (26), wherein the antibody recognizes an antigen related to a viral or bacterial infection.

An antigen related to a viral or bacterial infection according to the present invention is an antigen related to its infection and growth in a viral or bacterial target cell and also includes a viral or bacterial product. Examples include gp120 (*Virology*, 248, 394 (1998)), CXCR4 (*J. Virology*, 72, 8453 (1998)), Vero toxin (*J. Clinical Microbiology*, 34, 2053 (1996)) and the like.

(45) An agent for diagnosing a cancer, comprising the immunologically functional molecule according to (36) as an active ingredient.

(46) An agent for treating a cancer, comprising the immunologically functional molecule according to (36) as an active ingredient.

(47) An agent for preventing a cancer, comprising the immunologically functional molecule according to (36) as an active ingredient.

(48) An agent for diagnosing an allergy or inflammation, comprising the antibody according to (39) as an active ingredient.

(49) An agent for treating an allergy or inflammation, comprising the antibody according to (39) as an active ingredient.

(50) An agent for preventing an allergy or inflammation, comprising the antibody according to (39) as an active ingredient.

(51) An agent for diagnosing a cardiovascular disease, comprising the antibody according to (42) as an active ingredient.

(52) An agent for treating a cardiovascular disease, comprising the antibody according to (42) as an active ingredient.

(53) An agent for preventing a cardiovascular disease, comprising the antibody according to (42) as an active ingredient.

(54) An agent for diagnosing an autoimmune disease, comprising the antibody according to (43) as an active ingredient.

(55) An agent for treating an autoimmune disease, comprising the antibody according to (43) as an active ingredient.

(56) An agent for preventing an autoimmune disease, comprising the antibody according to (43) as an active ingredient.

(57) An agent for diagnosing a viral or bacterial infection, comprising the antibody according to (44) as an active ingredient.

(58) An agent for treating a viral or bacterial infection, comprising the antibody according to (44) as an active ingredient.

(59) An agent for preventing a viral or bacterial infection, comprising the antibody according to (44) as an active ingredient

(60) An agent for diagnosing various diseases, comprising the peptide or protein according to (26) or (27) as an active ingredient.

Examples of the various diseases according to the present invention include a cancer, an allergic disease, an inflammatory disease, a cardiovascular disease, an autoimmune disease, a viral or bacterial infection and the like.

(61) An agent for treating various diseases, comprising the peptide or protein according to (60) as an active ingredient.

(62) An agent for preventing various diseases, comprising the peptide or protein according to (60) as an active ingredient.

Based on the binding form of immunologically functional molecules, the sugar chain is roughly classified into two kinds, namely a sugar chain which binds to asparagine (called N-glycoside-linked sugar chain) and a sugar chain which binds to serine, threonine and the like (called O-glycoside-linked sugar chain).

The N-glycoside-linked sugar chain according to the present invention has various structures (*Biochemical Experimentation Method 23—Method for Studying Glycoprotein Sugar Chains* (Gakkai Shuppan Center), edited by Reiko Takahashi (1989)), but each case has the following common basic core structure.

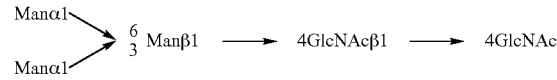

In the above structure, the sugar chain terminal which binds to asparagine is called a reducing terminal, and the opposite side is called a non-reducing terminal. The fucose may be bound to N-acetylglucosamine of the reducing terminal by, for example, an $\alpha 1,3$ bond, an $\alpha 1,6$ bond or the like.

Examples of the N-glycoside-linked sugar chains include a high mannose type, in which only mannose binds to the non-reducing terminal of the core structure; a complex type, in which the non-reducing terminal side of the core structure has one or more branches of galactose-N-acetylglucosamine (hereinafter referred to as "Gal-GlcNAc") and the non-reducing terminal side of Gal-GlcNAc further has a structure such as a sialic acid, bisecting N-acetylglucosamine or the like; a hybrid type, in which the non-reducing terminal side of the core structure has both branches of the high mannose N-glycoside-linked sugar chain and complex N-glycoside-linked sugar chain; and the like.

An immunologically functional molecule is a molecule which is originally derived from the living body and is involved in various immune responses. Specifically, it includes antibodies, proteins, peptides and the like.

An antibody is a protein which is produced in vivo by an immune response as a result of the stimulation by a foreign antigen and has an activity to specifically bind to the antigen. Examples of the antibody include an antibody secreted by a hybridoma cell prepared from spleen cells of an immunized animal after immunization of the animal with an antigen, as well as an antibody prepared by gene recombination techniques, namely an antibody obtained by introducing an antibody encoding gene-inserted antibody expression vector into a host cell. Examples include an antibody produced by a hybridoma, a humanized antibody, a human antibody and the like.

A hybridoma is a cell which produces a monoclonal antibody having a desired antigen specificity and is obtained by cell fusion of a B cell prepared by immunizing a mammal other than human with an antigen, with a myeloma cell derived from a mouse or the like.

Humanized antibodies includes a human chimeric antibody, a human complementarity determining region (hereinafter referred to as "CDR")-grafted antibody and the like.

A human chimeric antibody is an antibody comprising an antibody heavy chain variable region (hereinafter referred also to as "HV" or "VH", wherein the heavy chain is an H chain and the variable region is a V region) and an antibody light chain variable region (hereinafter referred to also as "LV" or "VL", wherein the light chain is an L chain) derived from an animal other than human, a heavy chain constant region (hereinafter referred to also as "CH", wherein the constant region is a C region) of a human antibody and a light chain constant region (hereinafter referred to also as "CL") of a human antibody. Animals other than human may be any of mouser rat, hamster, rabbit and the like, so long as a hybridoma can be prepared from the same.

The human chimeric antibody can be produced by obtaining cDNAs encoding VH and VL from a hybridoma which produces a monoclonal antibody, inserting each of the cDNAs into an expression vector for a host cell having a gene encoding human antibody CH and human antibody CL to construct a human chimeric antibody expression vector, and then introducing the vector into a host cell to express the antibody.

Any CH of the human chimeric antibody may be used, so long as it belongs to a human immunoglobulin (hereinafter referred to as "hIg"), but those of the hIgG class are preferred and any of subclasses belonging to the hIgG class, such as hIgG1, hIgG2, hIgG3 and hIgG4, can be used. Moreover, any CL of the human chimeric antibody may be used, so long as it belongs to hIg, and those of κ class or λ class can be used.

A human CDR-grafted antibody is an antibody in which amino acid sequences of CDRs of the VH and VL of an antibody derived from an animal other than human are grafted to appropriate positions of the VH and VL of a human antibody.

The human CDR-grafted antibody can be produced by constructing cDNAs encoding V regions in which CDR sequences of the VH and VL of an antibody derived from an animal other than human are grafted to CDR sequences of the VH and VL of a human antibody, inserting each of the cDNAs into an expression vector for a host cell having a gene encoding the CH of a human antibody and the CL of a human antibody to construct a human CDR-grafted antibody expression vectors and introducing the expression vector into a host cell to express the human CDR-grafted antibody.

The CH of the human CDR-grafted antibody may be any region which belongs to hIg, but those of the hIgG class are preferred. Any of subclasses belonging to the hIgG class such as hIgG1, hIgG2, hIgG3, hIgG4 and the like can be used. Also, the CL of the human CDR-grafted antibody may be any region which belongs to hIg, and those of κ class or λ class can be used.

A human antibody is originally meant to be an antibody naturally existing in the human body, but it also includes antibodies obtained from a human antibody phage library and a human antibody-producing transgenic animal or a human antibody-producing transgenic plant, which are prepared based on recent advances in genetic engineering, cell engineering and developmental engineering techniques.

The antibody existing in the human body can be obtained, for example, by isolating a human peripheral blood lymphocyte, immortalizing it by its infection with EB virus or the like, followed by cloning, culturing a lymphocyte capable of producing the antibody, and purifying the antibody from the culture mixture.

The human antibody phage library is a library in which an antibody fragment, such as Fab, a single chain antibody or the like, is expressed on the phage surface by inserting an antibody gene prepared from human B cell into a phage gene. A phage expressing an antibody fragment having the desired antigen binding activity can be recovered from this library, using its activity to bind to an antigen-immobilized substrate as the marker. The antibody fragment can be converted further into a human antibody molecule comprising two full H chains and two full L chains by genetic engineering techniques.

A human antibody-producing transgenic non-human animal is an animal in which a human antibody-encoding gene is integrated into cells. Specifically, a human antibody-producing transgenic animal can be prepared by introducing a human antibody-encoding gene into a mouse ES cell, transplanting the ES cell into an early stage embryo of another mouse, and developing an animal. The human antibody may be prepared and accumulated in a culture mixture of the human antibody-producing transgenic animal by obtaining a human antibody-producing hybridoma according to a hybridoma preparation method usually carried out in mammals other than human and then culturing the hybridoma.

An activity of antibodies of the present invention includes ADCC activity.

ADCC activity as used herein refers to an activity to injury a tumor cell or the like by activating an effector cell via the binding of the Fc region of an antibody to an Fc receptor existing on the surface of an effector cell such as a killer cell, a natural killer cell, an activated macrophage or the like (*Monoclonal Antibodies: Principles and Applications*, Wiley-Liss, Inc., Chapter 2.1 (1995)).

Any protein and peptide can be used, so long as they can activate various immune response. Examples include interferon molecules, such as interleukin-2 (IL-2) (*Science,* 193, 1007 (1976)) and interleukin-12 (IL-12) (*J. Leuc. Biol.,* 55, 280 (1994)); colony-stimulating factors, such as granulocyte colony-stimulating factor (G-CSF) (*J. Biol. Chem.,* 258, 9017 (1983)), macrophage colony-stimulating factor (M-CSF) (*J. Exp. Med.,* 173, 269 (1992)) and granulocyte macrophage colony-stimulating factor (MG-CSF) (*J. Biol. Chem.,* 252, 1998 (1977)); growth factors, such as erythropoietin (EPO) (*J. Biol. Chem.,* 252, 5558 (1977)) and thrombopoietin (TPO) (*Nature,* 369, 533 (1994)); and the like.

The activities of protein and peptide of the present invention are activities of various immunocompetent cells including lymphocytes (T cell, B cell and the like) and macrophage, or various immune response reactions, when the sugar chain-containing protein and peptide are administered into the living body.

The promotion of activities of protein and peptide of the present invention includes activation of NK cell and T cell by IL-2 and IL-12, promotion activities of erythrocyte production by EPO and the like which are further increased, 1. Method for Analyzing Sugar Chain of Immunologically Functional Molecule, (1) Compositional Analysis of Neutral Sugar and Aminosugar As described above, the sugar chain of IgG comprises a neutral sugar, such as galactose, mannose, fucose or the like, an aminosugar, such as N-acetylglucosamine or the like, and an acidic sugar, such as sialic acid or the like.

Regarding compositional analysis of the sugar chain of an antibody, the compositional ratio can be analyzed by releasing neutral sugars or amino sugars by acid hydrolysis of the sugar chain.

Specific methods include a method using a sugar composition analyzer (BioLC) manufactured by Dionex. The BioLC is an apparatus for analyzing sugar composition by HPAEC-PAD (high performance anion-exchange chromatography-pulsed amperometric detection) method (*J. Liq. Chromatogr.,* 6, 1577 (1983)).

The compositional ratio can also be analyzed by a fluorescence labeling method using 2-aminopyridine. Specifically, the compositional ratio can be calculated by fluorescence-labeling an acid-hydrolyzed sample with 2-aminopyridine in accordance with a known method (*Agric. Biol. Chem.,* 55 (1), 283-284 (1991)) and carrying out HPLC analysis.

(2) Sugar Chain Structure Analysis

The structure of the sugar chain of an antibody can be analyzed by a two-dimensional sugar chain mapping method (*Anal. Biochem.*, 171, 73 (1988), *Biochemical Experimentation Method 23—Method for Studying Glycoprotein Sugar Chains* (Gakkai Shuppan Center), edited by Reiko Takahashi (1989)). The two-dimensional sugar chain mapping method is a method in which the sugar chain structure is estimated, for example, by plotting the retention time or eluting position of the sugar chain by reverse phase chromatography as the X axis and the retention time or eluting position of the sugar chain by a normal phase chromatography as the Y axis, and comparing the results with those of known sugar chains.

Specifically, the sugar chain is released from the antibody by hydrazinolysis of the antibody, fluorescence labeling of the sugar chain with 2-aminopyridine (hereinafter referred to as "PA") (*J. Biochem.*, 95, 197 (1984)) is carried out, and then the sugar chain is separated from an excess PA reagent and the like by gel filtration and subjected to reverse phase chromatography. Subsequently, each peak of the fractionated sugar chain is analyzed by normal phase chromatography. Based on these results, the sugar chain structure can be estimated by plotting the spots on a two-dimensional sugar chain map and comparing them with those of sugar chain standards (manufactured by Takara Shuzo) or a reference (*Anal. Biochem.*, 171, 73 (1988)).

In addition, the structure estimated by the two-dimensional sugar chain mapping method can be confirmed by mass spectrometry, such as MALDI-TOF-MS or the like, of each sugar chain.

2. Method for Controlling the Activity of Immunologically Functional Molecule

The method of the present invention for controlling the activity of an immunologically functional molecule is described below using immunoglobulin G (hereinafter referred to as "IgG") as an example.

The N-glycoside-linked sugar chain which binds to IgG is a biantennary composite sugar chain mainly having the following structure (hereinafter referred to as "biantennary").

cosamine is added to at least one of the sugar chain binding regions, the activity of the immunologically functional molecule is increased. As an example, the degree of the activity of IgG will be as follows: F0 antibody>F1 antibody>F2 antibody, wherein the F0 antibody designates an antibody in which the N-glycoside-linked sugar chain in which fucose is not bound to N-acetylglucosamine is added to both of the two sugar chain binding regions; the F1 antibody designates an antibody in which the N-glycoside-linked sugar chain in which fucose is not bound to N-acetylglucosamine is added to one of the sugar chain binding regions; and the F2 antibody designates an antibody in which the N-glycoside-linked sugar chain in which fucose is bound to N-acetylglucosamine is added to both of the sugar chain binding regions.

The produced antibody may not always have a single sugar chain structure, and the F0 antibody, F1 antibody and F2 antibody may be present as a mixture when the presence or absence of fucose is taken into consideration. In order to control ADCC activity of the produced antibody, the sugar chain bound to the antibody is analyzed using the above method for analyzing the sugar chain of an immunologically functional molecule, and using the analyzed result as an index.

ADCC activity of the produced antibody may be promoted by increasing the existing ratio of the F1 antibody and F0 antibody. Specifically, the F1 antibody and F0 antibody may be purified, or expression in a host cell may be regulated in such a manner that the N-glycoside-linked sugar chain in which fucose is not bound to N-acetylglucosamine is added to the immunologically functional molecule.

ADCC activity of the produced antibody may be inhibited by increasing the existing ratio of the F2 antibody. Specifically, the F2 antibody may be purified, or expression in a host cell may be regulated in such a manner that the N-glycoside-linked sugar chain in which fucose is bound to N-acetylglucosamine is added to the immunologically functional molecule.

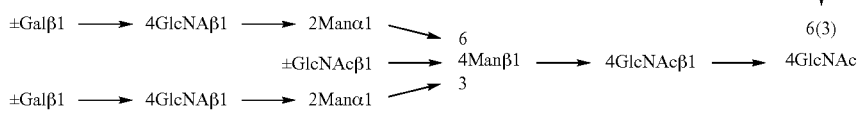

The present invention also includes similar sugar chains wherein an acidic sugar, sialic acid, is further added to Gal of the non-reducing terminal of N-glycoside-linked sugar chain or a bisecting N-acetylglucosamine is added to the N-glycoside-linked sugar chain.

In an IgG type, an N-glycoside-linked sugar chain is bound to one position in the Fc region. Since an IgG type comprises two H chains, the Fc moiety is present at two positions in one antibody molecule. Accordingly, the sugar chain binding region is also present at two positions.

The activity of IgG changes depending on the number of N-glycoside-linked sugar chain in which fucose is not bound to N-acetylglucosamine, to be added to the above two sugar chain binding regions. That is, when the N-glycoside-linked sugar chain in which fucose is not bound to N-acetylglu- As described above, strength of the desired activity can be controlled by regulating the existing ratio of F0 antibody, F1 antibody and F2 antibody.

3. Method for Producing Immunologically Functional Molecule

A method for producing an immunologically functional molecule having an N-glycoside-linked sugar chain in which fucose is not bound to N-acetylglucosamine or an immunologically functional molecule having an N-glycoside-linked sugar chain in which fucose is bound to N-acetylglucosamine is described below.

In order to bind a desired sugar chain to an antibody, a peptide or a protein, it can be produced by introducing a gene encoding the antibody, peptide or protein of interest into a host cell and culturing the resulting cell. Alternatively, it can also be produced by introducing a gene encoding the antibody, peptide or protein of interest into an animal or a plant and culturing the resulting animal or plant.

The host cell, animal or plant useful in the production of an immunologically functional molecule having an N-glycoside-linked sugar chain in which fucose is not bound to N-acetylglucosamine may be any cell, animal or plant, so long as, for example, it has a low enzyme activity of adding fucose to the N-acetylglucosamine which binds to the Fc region of an antibody or does not have the enzyme activity. Examples of the cell which has a low enzyme activity of adding fucose to the N-acetylglucosamine that binds to the Fc region of the antibody or does not have the enzyme activity include a rat myeloma cell, YB2/3HL.P2.G11.16Ag.20 cell (ATCC CRL 1662 (hereinafter referred to as "YB2/0 cell")), and the like.

Also, a cell, animal or plant having a low or no enzyme activity related to an α1,6 bond may be made, for example, by deleting a gene encoding the α1,6 bond-related enzyme in the host cell, animal or plant or by adding a mutation to the gene to reduce or eliminate the enzyme activity, and may be used as a host cell, animal or plant. The α1,6 bond-related enzyme includes fucosyltrarnsferases, and is preferably α1,6-fucosyltransferase (hereinafter referred to as "FUT8").

The host cell, animal or plant for use in the production of an immunologically functional molecule having an N-glycoside-linked sugar chain in which fucose is bound to N-acetylglucosamine may be any cell, animal or plant, so long as, for example, it has a high enzyme activity of adding fucose to the N-acetylglucosamine which binds to the Fc region of an antibody.

Also, a cell, animal or plant which has a high enzyme activity related to an α1,6 bond can be prepared by introducing a gene encoding the α1,6 bond-related enzyme in the host cell, animal or plant or by adding a mutation to the gene to increase the enzyme activity, and may be used as a host cell, animal or plant. The α1,6 bond-related enzyme includes fucosyltransferases, and is preferably FUT8.

Host cells may be any of bacteria, yeast, animal cells, insect cells, plant cells and the like, so long as they can express the gene of interest.

Examples of bacterial host cells include microorganisms belonging to the genus *Escherichia*, the genus *Serratia*, the genus *Bacillus*, the genus *Brevibacterium*, the genus *Corynebacterium*, the genus *Mycobacterium*, the genus *Pseudomonas* and the like, such as *Escherichia coli* XL1-Blue, *Escherichia coli* XL2-Blue, *Escherichia coil* DH1, *Escherichia coli* MC10000, *Escherichia coil* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coil* GI1698, *Escherichia coli* TB1, *Serratia ficaria, Serratia fonticola Serratia liquefaciens, Serratia marcescens, Bacillus subtilis, Bacillus amyloliquefaciens, Brevibacterium ammoniagenes, Brevibacterium immariophilum* ATCC 14068, *Brevibacterium saccharolyticum* ATCC 14066, *Brevibacterium flavum* ATCC 14067, *Brevibacterium lactofermentum* ATCC 13869, *Corynebacterium glutamicum* ATCC 13032, *Corynebacterium glutamicum* ATCC 13869, *Corynebacterium acetoacidophilum* ATCC 13870, *Mycobacterium ammoniaphilum* ATCC 15354, *Pseudomonas putida, Pseudomonas* sp. D-0110 and the like, Examples of yeast host cells includes microorganisms belonging to the genus *Saccharomyces*, the genus *Schizosaccharomyces*, the genus *Kluyveromyces*, the genus *Trichosporon*, the genus *Schwanniomyces*, the genus *Pichia*, the genus *Candida* and the like, such as *Saccharomyces cerevisiae, Schizosaccharomyces pombe, Kluyveromyces lactis, Trichosporon pullulans, Schwanniomyces alluvius, Candida utilis* and the like.

Examples of animal host cells include mouse myeloma cells, such as NS0 cell and SP2/0 cell; Chinese hamster ovary cells, such as CHO/dhfr⁻ cell and CHO/DG44 cell; rat myeloma cells, such as YB2/0 cell and IR983F cell; monkey cells, such as COS cell; human myeloma cells, such as Namalwa cell; and the like. Preferably, Chinese hamster ovary cells, such as CHO/DG44 cell and the like, can be used.

Examples of insect host cells include *Spodoptera frugiperda* ovary cells, such as Sf9 and Sf21 (*Baculovirus Expression Vectors, A Laboratory Manual*, W. H. Freeman and Company, New York (1992)); a *Trichoplusia ni* ovary cell such as High 5 (manufactured by Invitrogen); and the like.

Examples of plant host cells include plant cells of tobacco, potato, tomato, carrot, soybean, rape, alfalfa, rice, wheat, barley and the like.

An immunologically functional molecule can be produced by culturing the obtained transformant in a medium to form and accumulate the immunologically functional molecule in the resulting culture, and then recovering it from the culture.

In addition, an immunologically functional molecule can also be produced by constructing a transgenic animal or plant and culturing the resulting animal or plant.

The animal or plant for the production of an immunologically functional molecule having an N-glycoside-linked sugar chain in which fucose is not bound to N-acetylglucosamine may be any animal or plant, so long as, for example, it has a low enzyme activity of adding fucose to the N-acetylglucosamine which binds to the Fc region of an antibody or does not have the enzyme activity.

Also, a knockout non-human animal or knockout plant having a low or no enzyme activity related to an α1,6 bond may be prepared by deleting a gene encoding the α1,6 bond-related enzyme in the animal or plant or by adding a mutation to the gene to reduce or eliminate the enzyme activity, and may be used. The α1,6 bond-related enzyme includes fucosyltrarnsferases, and is preferably FUT8.

Any animal or plant may be used as an animal or plant for use in the production of an immunologically functional molecule having an N-glycoside-linked sugar chain in which fucose is bound to N-acetylglucosamine, so long as, for example, with regard to an antigen, it has a high enzyme activity of adding fucose to the N-acetylglucosamine which binds to the Fc region of the antibody.

Also, a transgenic non-human animal or transgenic plant which has a high enzyme activity related to an α1,6 bond may be prepared by introducing a gene encoding the α1,6 bond-related enzyme in the animal or plant or by adding a mutation to the gene to increase the enzyme activity, and may be used, The α1,6 bond-related enzyme includes fucosyltrarnsferases, and is preferably FUT8.

The transgenic non-human animal can be obtained by directly injecting a desired gene into a fertilized egg (*Proc. Natl. Acad. Sci. USA.*, 77, 7380 (1980)).

The transgenic non-human animals include mouse, rate rabbit, fowl, goat, cattle and the like.

Also, a transgenic non-human animal or knockout non-human animal having a desired gene can be obtained by introducing the desired gene into an embryonic stem cell and preparing the animal by an aggregation chimera method or injection chimera method (*Manipulating the Mouse Embryo, A Laboratory Manual*, Second Edition, Cold Spring Harbor Laboratory Press (1994); *Gene Targeting, A Practical Approach*, IRL Press at Oxford University Press (1993); *Bio-*

*material Series* 8, Gene Targeting, Preparation of mutation mouse using ES cell, Yodo-sha (1995)).

Examples of the embryonic stem cell include embryonic stem cells of mouse (*Nature*, 292, 154 (1981)), rat, fowl, pig, monkey, goat, cattle and the like.

In addition, the transgenic non-human animal or knockout non-human animal can also be prepared using a clonal technique in which a nucleus into which a desired gene is introduced is transplanted into an enucleated egg (*Science*, 280, 1256, (1998); *Science*, 278, 824, (1997)).

An immunologically functional molecule can be produced by introducing DNA encoding the immunologically functional molecule into an animal prepared by the above method to thereby form and accumulate the immunologically functional molecule in the animal, and then collecting the immunologically functional molecule from the animal. The immunologically functional molecule may be made to be formed and accumulated in the milk (Japanese Published Unexamined Patent Application No. 309192/88), egg or the like of the animal.

The method for producing a transgenic plant is described, for example, in a reference (*Biol. Chem.*, 380, 825 (1999)) and the like. The method for producing a knockout plant is described, for example, in a reference (*Plant Journal*, 11, 1195 (1997)).

Regarding the method for producing an immunologically functional molecule using a plant, the immunologically functional molecule can he produced, for example, by culturing a transgenic plant into which DNA encoding the immunologically functional molecule is introduced, in accordance with a known method (*Tissue Culture*, 20, (1994); *Tissue Culture*, 21, (1995); *Trends in Biotechnology*, 15, 45 (1997)) to thereby form and accumulate the immunologically functional molecule in the plant, and then collecting the immunologically functional molecule from the plant.

In addition, a gene-modified animal capable of producing an immunologically functional molecule having an N-glycoside-linked sugar chain in which fucose is not bound to N-acetylglucosamine or an immunologically functional molecule having an N-glycoside-linked sugar chain in which fucose is bound to N-acetylglucosamine can be obtained by crossing a transgenic non-human animal or knockout non-human animal of a fucosyltransferase, preferably FUT8, with a homologous but different line of the transgenic animal of a desired immunologically functional molecule. The crossing method includes natural crossing, in vitro fertilization and the like.

Also, it is possible to carry out mass production of the sugar chain by introducing a group of genes encoding the isolated enzymes and the like into yeast, *E. coli* and the like (*Nature Biotechnology*, 16, 847 (1998)). Further, the produced enzyme can be used in the modification of an antibody, peptide or protein with the sugar chain or production thereof.

In addition, a sugar chain which promotes the activity of an immunologically functional molecule, according to the present invention, can be substituted with a peptide (*J. Immunol.*, 160, 293 (1998)). Such a peptide has utility in the above method for utilizing sugar chains and is also excellent in view of convenience, because it can be easily fused with an immunologically functional molecule.

A method for producing an immunologically functional molecule having a promoted immunologically functional activity is described below. While a method for producing a humanized antibody is described herein as an example, other immunologically functional molecules can be prepared by the above-mentioned method or in accordance with a method similar thereto.

4. Method for Producing Humanized Antibody (1) Construction of Vector for Humanized Antibody Expression The vector for humanized antibody expression is an expression vector for use in an animal cell into which genes encoding the heavy chain (hereinafter referred to as "H chain") and light chain (hereinafter referred to as "L chain") C regions of a human antibody are inserted, and can be constructed by cloning each of genes encoding the H chain and L chain C regions of a human antibody into an expression vector for animal cell.

The C regions of a human antibody may be H chain and L chain C regions of a suitable human antibody, and examples include the C region of an IgG1 subclass of a human antibody H chain (hereinafter referred to as "hCγ1"), the C region of an κ class of a human antibody L chain (hereinafter referred to as "hCκ") and the like.

The genes encoding the H chain and L chain C regions of a human antibody may be a chromosomal DNA comprising exon and intron, or a cDNA.

The expression vector for animal cell may be any vector, so long as a gene encoding the C region of a human antibody can be inserted and expressed. Examples include pAGE107 (*Cytotechnology*, 3, 133 (1990)), pAGE103 (*J. Biochem.*, 101, 1307 (1987)), pHSG274 (*Gene*, 27, 223 (1984)), pKCR (*Proc. Natl. Acad. Sci. USA*, 78, 1527 (1981), pSG1 β d2-4 (*Cytotechnology*, 4, 173 (1990) ) and the like. The promoter and enhancer to be used in the expression vector for animal cell include SV40 early promoter and enhancer (*J. Biochem.*, 101, 1307 (1987)), Moloney mouse leukemia virus LTR (*Biochem. Biophys. Res. Comun.*, 149, 960 (1987) ), immunoglobulin H chain promoter (*Cell*, 41, 479 (1985)) and enhancer (*Cell*, 33, 717 (1983)) and the like.

The vector for humanized antibody expression may be any of a vector in which the antibody H chain and L chain are present on separate vectors or a vector in which they are present on the same vector (hereinafter referred to as "tandem vector"); however, a tandem vector for humanized antibody expression is preferable because such tandem humanized antibody expression vectors are easily constructed and introduced into an animal cell and expression amounts of the antibody H chain and L chain in the animal cell can be balanced (*J. Immunol. Methods*, 167, 271 (1994)).

The constructed vector for humanized antibody expression can be used for the expression of a human chimeric antibody and a human CDR-grafted antibody in animal cells.

(2) Preparation of cDNA Encoding V Region of Antibody Derived from Animal Other than Human cDNA encoding the H chain and L chain V regions of an antibody derived from an animal other than human, such as a mouse antibody, can be obtained as described below.

cDNA is synthesized by extracting mRNA from a hybridoma cell capable of producing the mouse antibody of interest. The synthesized cDNA is cloned into a vector, such as a phage, a plasmid or the like, to prepare a cDNA library. A recombinant phage or recombinant plasmid containing a cDNA encoding the H chain V region and a recombinant phage or recombinant plasmid containing a cDNA encoding the L chain V region are respectively isolated from the library using a C region moiety or V region moiety of a known mouse antibody as the probe. Complete nucleotide sequences of the mouse antibody H chain and L chain V regions of interest on the recombinant phage or recombinant plasmid are determined, and full amino acid sequences of the H chain and L chain V regions are deduced from the nucleotide sequences.

The animal other than human may be any animal, such as mouse, rat, hamsters rabbit or the like, so long as a hybridoma cell can be produced therefrom.

The method for preparing total RNA from a hybridoma cell includes a guanidine thiocyanate-cesium trifluoroacetate method (*Methods in Enzymol.*, 154, 3 (1987)). The method for preparing mRNA from total RNA includes an oligo (dT) immobilized cellulose column method (*Molecular Cloning: A Laboratory Manual*, Cold Spring Harbor Lab. Press, New York, 1985) and the like. Also, Fast Track mRNA Isolation Kit (manufactured by Invitrogen), Quick Prep mRNA Purification Kit (manufactured by Pharmacia) and the like can be exemplified as a kit for preparing mRNA from a hybridoma cell.

Examples of the method for synthesizing cDNA and preparing a cDNA library include conventional methods (*Molecular Cloning: A Laboratory Manual*, Cold Spring Harbor Lab. Press, New York, 1989; *Current Protocols in Molecular Biology*, Supplement 1-34), a method which uses a commercially available kit, such as Super Script™ Plasmid System for cDNA Synthesis and Plasmid Cloning (manufactured by GIBCO BRL) or ZAP-cDNA Kit (manufactured by Stratagene) and the like.

The vector into which the cDNA synthesized using mRNA extracted from a hybridoma cell is inserted in preparing a cDNA library may be any vector, so long as the cDNA can be inserted. Examples include ZAP Express (*Strategies*, 5, 58 (1992)), pBluescript II SK(+) (*Nucleic Acids Research*, 17, 9494 (1989)), λzapII (manufactured by Stratagene), λgt10 and λgt11 (*DNA Cloning: A Practical Approach, I*, 49 (1985)), Lambda BlueMid (manufactured by Clontech), λExCell and pT7T3 18U (manufactured by Pharmacia), pcD2 (*Mol. Cell. Biol.*, 3, 280 (1983)), pUC18 (*Gene*, 33, 103 (1985)) and the like, The *E. coli* to be used for introducing the cDNA library constructed by a phage or plasmid vector may be any strain, so long as the cDNA library can be introduced, expressed and maintained. Examples include XL1-Blue MRF' (*Strategies*, 5, 81 (1992)), C600 (*Genetics*, 39, 440 (1954)), Y1088 and Y1090 (*Science*, 222, 778 (1983)), NM522 (*J. Mol. Biol.*, 166, 1 (1983)), K802 (*J. Mol. Biol.*, 16, 118 (1966)), JM105 (*Gene*, 38, 275 (1985)) and the like.

A colony hybridization or plaque hybridization method which uses an isotope- or fluorescence-labeled probe may be used for selecting a cDNA clone encoding the H chain and L chain V regions of an antibody derived from an animal other than human from the cDNA library (*Molecular Cloning: A Laboratory Manual*, Cold Spring Harbor Lab. Press, New York, 1989). Also, the cDNA encoding the H chain and L chain V regions can be prepared through polymerase chain reaction (hereinafter referred to as "PCR"; *Molecular Cloning: A Laboratory Manual*, Cold Spring Harbor Lab. Press, New York, 1989; *Current Protocols in Molecular Biology*, Supplement 1-34) by preparing primers and using cDNA prepared from mRNA or a cDNA library as the template.

The nucleotide sequence of the cDNA selected by the above method can be determined by digesting the cDNA with appropriate restriction enzymes and the like, cloning the fragments into a plasmid, such as pBluescript SK(−) (manufactured by Stratagene) or the like, carrying out the reaction by a usually used nucleotide analyzing method, such as the dideoxy method of Sanger et al. (*Proc. Natl. Acad. Sci. USA*, 74, 5463 (1977)) or the like, and then analyzing the sequence using an automatic nucleotide sequence analyzer such as A.L.F. DNA sequencer (manufactured by Pharmacia) or the like.

Whether the obtained cDNA encodes the full amino acid sequence of the H chain and L chain V regions of the antibody containing a secretion signal sequence can be confirmed by estimating the full amino acid sequence of the H chain and L chain V regions from the determined nucleotide sequence and comparing it with full amino acid sequences of the H chain and L chain V regions of known antibodies (*Sequences of Proteins of immunological Interest*, US Dept. Health and Human Services, 1991).

(3) Analysis of V Region Amino Acid Sequence of Antibody Derived from Animal Other than Human Regarding the full amino acid sequence of the H chain and L chain V regions of the antibody comprising a secretion signal sequence, the length and N-terminal amino acid sequence of the secretion signal sequence can be estimated and subgroups to which they belong can be known by comparing it with full amino acid sequences of the H chain and L chain V regions of known antibodies (*Sequences of Proteins of Immunological Interest*, US Dept. Health and Human Services, 1991). Each CDR amino acid sequence of the H chain and L chain V regions can also be identified by comparing it with amino acid sequences of the H chain and L chain V regions of known antibodies (*Sequences of Proteins of Immunological Interest*, US Dep. Health and Human Services, 1991)

(4) Construction of Human Chimeric Antibody Expression Vector

A human chimeric antibody expression vector can be constructed by cloning cDNA encoding the H chain and L chain V regions of an antibody derived from an animal other than human into the upstream of a gene encoding the H chain and L chain C regions of a human antibody on the humanized antibody expression vector described in the item 4(1). For example, a human chimeric antibody expression vector can be produced by connecting cDNAs encoding the H chain and L chain V regions derived from an antibody of an animal other than human respectively with a synthetic cDNA which comprises a 3'-terminal side nucleotide sequences of the H chain and L chain V regions of an antibody derived from an animal other than human, a 5'-terminal side nucleotide sequence of the H chain and L chain C regions derived from a human antibody and appropriate restriction enzyme recognizing sequences on both termini, and cloning them into the upstream of a gene encoding the H chain and L chain C regions of a human antibody on the humanized antibody expression vector described in the item 4(1) in such a manner that they are expressed in a suitable form.

(5) Construction of cDNA Encoding V Region of Human CDR-Grafted Antibody

The cDNA encoding the H chain and L chain V regions derived from a human CDR-grafted antibody can be obtained as described below. First, the amino acid sequence of the framework (hereinafter referred to as "FR") of the H chain and L chain V regions of a human antibody for grafting CDR of the H chain and L chain V regions of an antibody derived from an animal other than human is selected. Any sequence can be used as the amino acid sequence of FR of the H chain and L chain V regions of a human antibody, so long as it is derived from a human antibody. For example, amino acid sequences of FR of the H chain and L chain V regions of human antibodies registered at a data base, such as Protein Data Bank or the like, an amino acid sequence common in each subgroup of FR of the H chain and L chain V regions of human antibodies (*Sequences of Proteins of Immunological Interest*, US Dept. Health and Human Services, 1991) and the like can be used, but in order to prepare a human CDR-grafted antibody having sufficient activity, it is desirable to select an amino acid sequence having a high homology (at least 60% or more) with the objective amino acid sequence of the H chain and L chain V regions of an antibody derived from an animal other than human.

Next, the objective amino acid sequence of CDR of the H chain and L chain V regions of an antibody derived from an animal other than human is grafted to the selected amino acid sequence of FR of the H chain and L chain V regions a human antibody, and amino acid sequences of the H chain and L chain V regions of the human CDR-grafted antibody are designed. Taking the codon usage found in nucleotide sequence of the antibody gene (*Sequences of Proteins of Immunological Interest*, US Dept. Health and Human Services, 1991) into consideration, the designed amino acid sequences are converted into DNA sequences and the DNA sequences encoding the amino acid sequences of the H chain and L chain V regions of the human CDR-grafted antibody are designed. Based on the designed DNA sequences, several synthetic DNA fragments having a length about 100 bases are synthesized, and PCR is carried out using these fragments. In this case, based on the reaction efficiency in the PCR and the length of DNA which can be synthesized, it is desirable to design 6 synthetic DNA fragments for each of the H chain and L chain.

Also, cloning into the vector for humanized antibody expression constructed in the item 4(1) can be easily carried out by introducing appropriate restriction enzyme recognizing sequences into 5'-termini of the synthetic DNA positioned at both termini. After the PCR, a plasmid having a DNA sequence encoding the amino acid sequence of the H chain and L chain V regions of the desired human CDR-grafted antibody is obtained by cloning the amplified product into plasmid, such as pBluescript SK(−) (manufactured by Stratagene) or the like, and determining the nucleotide sequence by the method described in the item 4(2).

(6) Modification of Amino Acid Sequence of V Region of Human CDR-Grafted Antibody It is known that when only the CDR of the H chain and L chain V regions of an antibody derived from an animal other than human of interest is simply grafted to the FR of the H chain and L chain V regions of a human antibody, the antigen binding activity of the human CDR-grafted antibody is reduced in comparison with the activity of the original antibody derived from an animal other than human (*BIO/TECHNOLOGY*, 9, 266 (1991)). As the cause of this, it is considered that not only amino acid sequences of CDR but also several amino acid sequences of FR in the H chain and L chain V regions of the original antibody derived from an animal other than the human are directly or indirectly related to the antigen binding activity, and these amino acid residues are changed into different amino acid residues of FR of the H chain and L chain V regions of the human antibody accompanied by the CDR grafting. In order to resolve this problem, in human CDR-grafted antibodies, attempts have been made to identify, among amino acid sequences of FR of the H chain and L chain V regions of a human antibody, an amino acid residue directly related to the binding to the antibody, an amino acid residue interacting with an amino acid residue of CDR and/or an amino acid residue which keeps three-dimensional structure of the antibody and is directly related to its binding to the antigen, and to increase the reduced antigen binding activity by changing these amino acid residues into amino acid residues found in the original antibody derived from an animal other than human (*BIO/TECHNOLOGY*, 9, 266 (1991)).

In preparing a human CDR-grafted antibody, it is preferable to efficiently identify these FR amino acid residues related to the antigen binding activity, such that construction and analysis of the three-dimensional structure of antibodies is preferably carried out using an x-ray crystal analysis (*J. Mol. Biol.*, 112, 535 (1977)), computer modeling (*Protein Engineering*, 7, 1501 (1994)) and the like. Although information on these three-dimensional structures of antibodies has provided useful information for the preparation of human CDR-grafted antibodies, a method for producing a human CDR-grafted antibody applicable to every antibody has not yet been established. It is preferable therefore to carry out various trial and error experiments on individual antibody, e.g., by preparing several modified products thereof and examining their correlation to the respective antigen binding activities.

Modification of the amino acid residues of the FR of the E chain and L chain V regions of a human antibody can be achieved by the PCR described in the item 4(5) using synthetic DNA for further modification. Achievement of the objective modification is confirmed by determining nucleotide sequence of the amplified fragment after PCR, by the method described in the item 4(2).

(7) Construction of Human CDR-Grafted Antibody Expression Vector

A human CDR-grafted antibody expression vector can be constructed by cloning the cDNA encoding the H chain and L chain V regions of human CDR-grafted antibody constructed in the items 4(5) and 4(6) into the upstream of the gene encoding the H chain and L chain C regions of a human antibody in the humanized antibody expression vector described in the item 4(1). For example, among the synthetic DNA fragments used in constructing the H chain and L chain V regions of human CDR-grafted antibody in (5) and (6) of the item 4, appropriate restriction enzyme recognizing sequences are introduced into 5'-termini of a synthetic DNA fragment positioned at both termini, and cloned into the upstream of the gene encoding the H chain and L chain C regions of a human antibody in the vector for humanized antibody expression described in the item 4(1), in such a manner that they can be expressed in a suitable form to thereby construct a human CDR-grafted antibody expression vector.

(8) Stable Production of Humanized Antibody

A transformant capable of producing a humanized antibody stably can be obtained by introducing the humanized antibody expression vector described in the items 4(4) and 4(7) into an appropriate animal cell.

The method for introducing an expression vector into an animal cell includes an electroporation method (Japanese Published unexamined Patent Application No. 257891/90, *Cytotechnology*, 3, 133 (1990)) and the like.

The animal cell into which a humanized antibody expression vector is introduced may be any cell, so long as it is an animal cell which can produce the humanized antibody. Preferred examples include a cell which has a low enzyme activity of adding fucose to N-acetylglucosamine to be bound to the Fc region of the produced antibody and a cell which has no such enzyme activity.

The cell which has a low enzyme activity of adding fucose to N-acetylglucosamine to be bound to the Fc region of the antibody or has no such enzyme activity is a cell having less or no enzymes related to the α1,6-bond. Examples include a cell which has a low fucosyltransferase activity, preferably FUT8 activity, and a cell which has no such activity.

Examples of the cell which has a low enzyme activity of adding fucose to N-acetylglucosamine to be bound to the Fc region of the antibody or has no enzyme activity include a rat myeloma cell, YB2/0 cell, and the like. A cell in which a gene involved in the α1,6 bond-related enzyme is deleted or the enzyme activity is reduced or eliminated by adding a mutation to the gene can also be used as an antibody producing cell.

Specific examples include mouse myeloma cells, such as NS0 cell and SP2/0 cell; Chinese hamster ovary cells, such as CHO/dhfr⁻ cell and CHO/DG44 cell; rat myeloma cells, such as YB2/0 cell and IR983F cell; human myeloma cells, such as Namalwa cell; and the likes Preferably, Chinese hamster ovary cells, such as CHO/DG44 cell and the like, can be used.

After introduction of the expression vector, the transformant capable of stably producing the humanized antibody can be selected using a medium for animal cell culture containing a drug, such as G418 sulfate (hereinafter referred to as "G418"; manufactured by SIGMA) or the like by the method disclosed in Japanese Published Unexamined Patent Application No. 257891/90. The medium for animal cell culture includes RPMI 1640 medium (manufactured by Nissui Pharmaceutical), CIT medium (manufactured by Nippon Pharmaceutical), EX-CELL 302 medium (manufactured by JRH), IMDM medium (manufactured by GIBCO BRL), Hybridoma-SFM medium (manufactured by GIBCO BRL), or a medium prepared by adding various additives, such as fetal bovine serum (hereinafter referred to as "FBS") and the like, to each of these media, and the like. The humanized antibody can be produced by culturing the obtained transformant in a medium, and accumulated in a culture supernatant. The produced amount and antigen binding activity of the humanized antibody in the culture supernatant can be measured by enzyme-linked immunosorbent assay (hereinafter referred to as "ELISA", *Antibodies: A Laboratory Manual*, Cold Spring Harbor Laboratory, Chapter 14, 1598; *Monoclonal Antibodies: Principles and Practice*, Academic Press Limited, 1996) and the like Also, production of the humanized antibody by the transformant can be increased using a DHFR gene amplification system or the like by the method disclosed in Japanese Published Unexamined Patent Application No. 257891/90.

The humanized antibody can be purified from a transformant-containing culture supernatant using a protein A column (*Antibodies: A Laboratory Manual*, Cold Spring Harbor Laboratory, Chapter 8, 1988; *Monoclonal Antibodies: Principles and Practice*, Academic Press Limited, 1996). Also, other purification methods generally used for the purification of protein can be used. For example, it can be purified by a combination of gel filtration, ion exchange chromatography, ultrafiltration and the like. The molecular weight of the H chain, L chain or whole antibody molecule of the purified humanized antibody can be measured by polyacrylamide gel electrophoresis (hereinafter referred to as "SDS-PAGE"; *Nature*, 227, 680 (1970)), Western blotting method (*Antibodies: A Laboratory Manual*, Cold Spring Harbor Laboratory, Chapter 12, 1988; *Monoclonal Antibodies: Principles and Practice*, Academic Press Limited, 1996) and the like.

An antibody production method has been shown in the above using an animal cell as the host, and as described in the above item 3, it can also be produced by a bacterium, a yeast, an insect cell, a plant cell, an animal or a plant.

(9) Activity Evaluation of Humanized Antibody

The activity of the purified humanized antibody to bind to an antigen or to an antigen-positive cultured cell line can be measured by the ELISA and fluorescence antibody method (*Cancer Immunol. Immunother.*, 36, 373 (1993)) and the like. The cytotoxic activity for antigen-positive cultured cell lines can be evaluated by measuring its CDC activity, ADCC activity and the like (*Cancer Immunol. Immunother.*, 36, 373 (1993)). In addition, safety and therapeutic effects of the humanized antibody in humans can be evaluated using an appropriate model of an animal species relatively close to human, such as *Macaca faseicularis* or the like, 5. Application Method of Immunologically Functional Molecule As shown in the humanized antibody described in the above item 4, an antibody having high ADCC activity is useful in the prevention and treatment of various diseases including a cancer, an allergy, a cardiovascular disease and a viral or bacterial infection.

In cancer, namely a malignant tumor, cancer cells proliferate. Conventional anticancer agents have a characteristic in inhibiting proliferation of cancer cells. On the other hand, since an antibody having high ADCC activity can treat cancers by injuring proliferation of the cancer cells through its cytotoxic effect, it is more effective as a therapeutic drug than conventional anticancer agents.

Since the allergic reaction is induced by the release of a mediator molecule from immune cells, the allergic reaction can be inhibited by removing the immune cells using an antibody having high ADCC activity.

The cardiovascular disease includes arteriosclerosis and the like. Arteriosclerosis is currently treated by balloon catheter, but cardiovascular diseases can be prevented and treated by inhibiting proliferation of arterial cells in re-stricture after the treatment, by using an antibody having high ADCC activity.

Various diseases including viral or bacterial infections can be prevented and treated by inhibiting proliferation of the virus- or bacterium-infected cells using an antibody having high ADCC activity, Also, an antibody having inhibited ADCC activity is useful in the prevention and treatment of autoimmune diseases. The antibody having inhibited ADCC activity is also useful in the prevention and treatment of autoimmune diseases from the viewpoint of suppressing the immune response promoted in autoimmune diseases.

The medicament containing the antibody according to the present invention can be administered as a therapeutic drug alone, but generally, it is desirable to provide it as a pharmaceutical preparation produced by an appropriate method well known in the technical field of manufacturing pharmacy, by mixing it with one or more pharmaceutically acceptable carriers, It is desirable to select a route of administration which is most effective in carrying out a treatment. Examples include oral administration and parenteral administration, such as buccal, airway, rectal, subcutaneous, intramuscular, intravenous or the like. In an antibody preparation, intravenous administration is preferred.

The dosage form includes sprays, capsules, tablets, granules, syrups, emulsions, suppositories, injections, ointments, tapes and the like.

Liquid preparations, such as emulsions and syrups, can be produced using, as additives, water; saccharides, such as sucrose, sorbitol, fructose etc.; glycols, such as polyethylene glycol, propylene glycol, etc.; oils, such as sesame oil, olive oil, soybean oil, etc.; antiseptics, such as p-hydroxybenzoic acid esters, etc.; flavors, such as strawberry flavor, peppermint, etc.; and the like.

Capsules, tablets, powders, granules and the like can be produced using, as additive, fillers, such as lactose, glucose, sucrose, mannitol, etc.; disintegrating agents, such as starch, sodium alginate, etc.; lubricants, such as magnesium stearate, talc, etc.; binders, such as polyvinyl alcohol, hydroxypropylcellulose, gelatin, etc.; surfactants, such as fatty acid ester, etc.; plasticizers, such as glycerol, etc.; and the like.

Examples of the pharmaceutical preparation suitable for parenteral administration include injections, suppositories, sprays and the like.

Injections may be prepared using a carrier, such as a salt solution, a glucose solution, a mixture of both thereof or the like. Alternatively, powdered injections can be prepared by freeze-drying the humanized antibody in the usual way and adding sodium chloride thereto.

Suppositories may be prepared using a carrier such as cacao butter, a hydrogenated fat or carboxylic acid.

Also, sprays may be prepared using the compound as such or using a carrier which does not stimulate the buccal or airway mucous membrane of the patient and can facilitate absorption of the compound by dispersing it as fine particles.

Examples of the carrier include lactose, glycerol and the like. Depending on the properties of the compound and the carrier to be used, it is possible to produce pharmaceutical preparations such as aerosols, dry powders and the like. In addition, the components exemplified as additive agents for oral preparations can also be added to these parenteral preparations.

Although the clinical dose or the frequency of administration varies depending on the objective therapeutic effect, administration method, treating period, age, body weight and the like, it is usually from 10 µg/kg to 20 mg/kg per day and per adult.

Also, regarding the method for examining antitumor effect of the antibody on various tumor cells, in vitro tests include CDC activity measuring method, ADCC activity measuring method and the like, and in vivo tests include an antitumor experiment using a tumor system in an experimental animal such as a mouse or the like.

CDC activity and ADCC activity measurements and antitumor experiments can be carried out in accordance with the methods described in references (*Cancer Immunology Immunotherapy*, 36, 373 (1993); *Cancer Research*, 54, 1511 (1994)) and the like.

6. Method for Promoting or Inhibiting Activity of Immunologically Functional Molecule The activity of an immunologically functional molecule can be promoted by producing an antibody, peptide or protein to which a fucose-free sugar chain is bound by the above method.

When the immunologically functional molecule having the promoted activity is administered to the living body, various immune cells including cells such as killer cells, natural killer cells, activated macrophages and the like as effector cells relating to the ADCC activity are activated in the living body, so that it becomes possible to control various immune responses.

Also, the activity of an immunologically functional molecule can be inhibited by producing an antibody, a peptide or a protein to which a fucose-existing sugar chain is bound by the above method.

When the immunologically functional molecule having the inhibited activity is administered to the living body, activities of various immune cells involved in the ADCC activity are weakened in the living body, so that it becomes possible to control various immune responses.

Examples of the present invention are shown below, but the scope of the present invention is not limited thereto.

BRIEF EXPLANATION OF THE DRAWINGS

FIG. 1 is a graph showing electrophoresis patterns of SDS-PAGE of five purified anti-GD3 chimeric antibodies (using gradient gel from 4 to 15%). The upper drawing and the lower drawing show a result of the electrophoresis under non-reducing conditions and that under reducing conditions, respectively. Lanes 1 to 7 show an electrophoresis pattern of high molecular weight markers, an electrophoresis pattern of YB2/0-GD3 chimeric antibody, an electrophoresis pattern of CHO/DG44-GD3 chimeric antibody, an electrophoresis pattern of SP2/0-GD3 chimeric antibody, an electrophoresis pattern of NS0-GD3 chimeric antibody (302), an electrophoresis pattern of NS0-GD3 chimeric antibody (GIT), and an electrophoresis pattern of low molecular weight markers, respectively.

FIG. 4 is a graph showing electrophoresis patterns of SDS-PAGE of three purified anti-hIL-5Rα CDR-grafted antibodies (using gradient gel from 4 to 15%). The upper drawing and the lower drawing show results of the electrophoresis carried out under non-reducing conditions and those under reducing conditions, respectively. Lanes 1 to 5 show an electrophoresis pattern of high molecular weight markers, an electrophoresis pattern of YB2/0-hIL-5RCDR antibody, an electrophoresis pattern of CHO/d-hIL-5RCDR antibody, an electrophoresis pattern of NS0-hIL-5RCDR antibody, and an electrophoresis pattern of low molecular weight markers, respectively.

FIG. 8 is a graph showing an elution pattern of reverse phase HPLC elution of a PA-treated sugar chain (left side), and an elution pattern obtained by treating the PA-treated sugar chain with α-L-fucosidase and then analyzed by reverse phase HPLC (right side), of the purified anti-hIL-5Rα CDR-grafted antibody produced by YB2/0 (upper side) and the purified anti-hIL-5Rα CDR-grafted antibody produced by NS0 (lower side). The axis of ordinates and the axis of abscissas show relative the fluorescence intensity and the elution time, respectively.

FIG. 10 is a graph showing the GD3-binding activity of non-adsorbed fraction and a part of adsorbed fraction, measured by changing the antibody concentration. The axis of ordinates and the axis of abscissas show the binding activity with GD3 and the antibody concentration, respectively. Closed circles and open circles show the non-adsorbed fraction and a part of the adsorbed fraction, respectively. The lower graph shows the ADCC activity of non-adsorbed fraction and a part of adsorbed fraction for a human melanoma line G-361. The axis of ordinates and the axis of abscissas show the cytotoxic activity and the antibody concentration, respectively. Closed circles and open circles show the non-adsorbed fraction and a part of the adsorbed fraction, respectively.

BEST MODE FOR CARRYING OUT THE INVENTION

EXAMPLE 1

Figure 2:
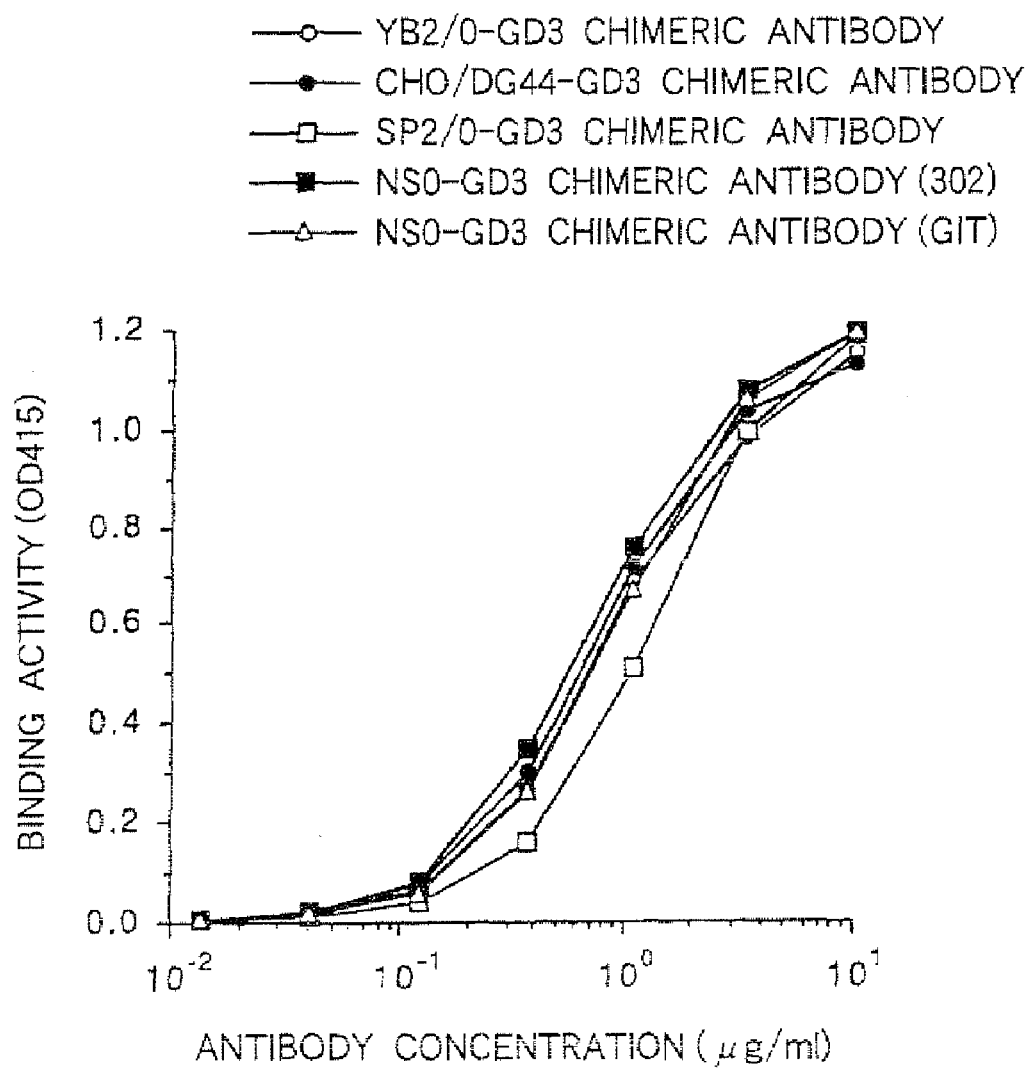
FIG. 2 is a graph showing the activity of five purified anti-GD3 chimeric antibodies to bind to GD3, measured by changing the antibody concentration. The axis of ordinates and the axis of abscissas show the binding activity with GD3 and the antibody concentration, respectively. Open circles, closed circles, open squares, closed squares, and open triangles show the activity of YB2/0-GD3 chimeric antibody, the activity of CHO/DG44-GD3 chimeric antibody, the activity of SP2/0-GD3 chimeric antibody, the activity of NS0-GD3 chimeric antibody (302), and the activity of NS0-GD3 chimeric antibody (GIT), respectively.

Production of Anti-Ganglioside GD3 Human Chimeric Antibody:

1. Construction of Tandem Expression Vector, pChiLHGM4, for Anti-Ganglioside GD3 Human Chimeric Antibody A plasmid, pChi641LGM40, was constructed by ligating a fragment of about 4.03 kb containing an L chain cDNA, obtained by digesting an L chain expression vector, pChi641LGM4 (*J. Immunol. Methods*, 167, 271 (1994)) for anti-ganglioside GD3 human chimeric antibody (hereinafter referred to as "anti-GD3 chimeric antibody") with restriction enzymes, MluI (manufactured by Takara Shuzo) and SalI (manufactured by Takara Shuzo), with a fragment of about 3.40 kb containing a G418-resistant gene and a splicing signal, obtained by digesting an expression vector pAGE107 (*Cytotechnology*, 3, 133 (1990)) for animal cell with restriction enzymes, MluI (manufactured by Takara Shuzo) and SalI (manufactured by Takara Shuzo), using DNA Ligation Kit (manufactured by Takara Shuzo), and then transforming *E. coli* HB101 (*Molecular Cloning; A Laboratory Manual*, Cold Spring Harbor Lab. Press, New York, 1989) with the ligated product using DNA Ligation Kit (manufactured by Takara Shuzo).

Next, a fragment of about 5.68 kb containing an L chain cDNA, obtained by digesting the constructed plasmid pChi641LGM40 with a restriction enzyme, ClaI (manufactured by Takara Shuzo), blunt-ending it using DNA Blunting Kit (manufactured by Takara Shuzo) and further digesting it with MluI (manufactured by Takara Shuzo), was ligated with a fragment of about 8.40 kb containing an H chain cDNA, obtained by digesting an anti-GD3 chimeric antibody H chain expression vector, pChi641HGM4 (*J. Immunol. Methods*, 167, 271 (1994)) with a restriction enzyme, XhoI (manufactured by Takara Shuzo), blunt-ending it using DNA Blunting Kit (manufactured by Takara Shuzo) and further digesting it with MluI (manufactured by Takara shuzo), using DNA Ligation Kit (manufactured by Takara Shuzo), and then *E. coli* HB101 (*Molecular Cloning: A Laboratory Manual*, Cold Spring Harbor Lab. Press, New York, 1989) was transformed with the ligated product to thereby construct a tandem expression vector, pChi641LHGM4, for anti-GD3 chimeric antibody.

2. Production of Cells Stably Producing Anti-GD3 Chimeric Antibody

Using the tandem expression vector pChi641LHGM4, for anti-GD3 chimeric antibody constructed in the item 1 of Example 1, cells capable of stably producing an anti-CD3 chimeric antibody were prepared as described below.

(1) Production of Producer Cell Using Rat Myeloma YB2/0 Cell

After introducing 5 μg of the anti-GD3 chimeric antibody expression vector, pChi641LHGM4, into $4 \times 10^6$ cells of rat myeloma YB2/0 by electroporation (*Cytotechnology*, 3, 133 (1990)), the cells were suspended in 40 ml of RPMI1640-FBS (10) (RPMI1640 medium containing 10% FBS (manufactured by GIBCO BRL)) and dispensed in 200 μl/well into a 96 well culture plate (manufactured by Sumitomo Bakelite).

Twenty-four hours after culturing at 37° C. in a 5% $CO_2$ incubator, G418 was added to a concentration of 0.5 mg/ml, followed by culturing for 1 to 2 weeks. The culture supernatant was recovered from respective well in which colonies of transformants showing G418 resistance were formed and growth of colonies was observed, and the antigen binding activity of the anti-GD3 chimeric antibody in the supernatant was measured by the ELISA shown in the item 3 of Example 1.

Regarding the transformants in wells in which production of the anti-GD3 chimeric antibody was observed in culture supernatants, in order to increase amount of the antibody production using a DHFR gene amplification system, each of them was suspended in the RPMI1640-FBS(10) medium containing 0.5 mg/ml of G418 and 50 nM DHFR inhibitor, methotrexate (hereinafter referred to as "MTX"; manufactured by SIGMA) to give a density of 1 to $2\times10^5$ cells/ml, and the suspension was dispensed in 2 ml into wells of a 24 well plate (manufactured by Greiner). Transformants showing 50 nM MTX resistance were induced by culturing at 37° C. for 1 to 2 weeks in a 5% $CO_2$ incubator. The antigen binding activity of the anti-GD3 chimeric antibody in culture supernatants in wells in which growth of transformants was observed was measured by the ELISA shown in the item 3 of Example 1. Regarding the transformants in wells in which production of the anti-GD3 chimeric antibody was observed in culture supernatants, the MTX concentration was increased to 100 nM and then to 200 nM, and a transformant capable of growing in the RPMI1640-FBS(10) medium containing 0.5 mg/ml of G418 and 200 nM MTX and of producing the anti-GD3 chimeric antibody in a large amount was finally obtained by the same method as described above. The obtained transformant was made into a single cell (cloning) by limiting dilution twice.

The obtained anti-GD3 chimeric antibody-producing transformed cell clone 7-9-51 has been deposited on Apr. 5, 1999, as FERM BP-6691 in National Institute of Bioscience and Human Technology, Agency of Industrial Science and Technology (Higashi 1-1-3, Tsukuba, Ibaraki, Japan).

(2) Production of Producer Cell Using CHO/DG44 Cell

After introducing 4 μg of the anti-GD3 chimeric antibody expression vector, pChi641LHGM4, into $1.6\times10^6$ cells of CHO/DG44 by electroporation (*Cytotechnology*, 3, 133 (1990)), the cells were suspended in 10 ml of IMDM-FBS (10) (IMDM medium containing 10% FBS and 1× concentration of HT supplement (manufactured by GIBCO BRL)) and dispensed in 200 μl/well into a 96 well culture plate (manufactured by Iwaki Glass). Twenty-four hours after culturing at 37° C. in a 5% $CO_2$ incubator, G418 was added to a concentration of 0.5 mg/ml, followed by culturing for 1 to 2 weeks. The culture supernatant was recovered from respective well in which colonies of transformants showing G418 resistance were formed and growth of colonies was observed, and the antigen binding activity of the anti-GD3 chimeric antibody in the supernatant was measured by the ELISA shown in the item 3 of Example 1.

Regarding the transformants in wells in which production of the anti-GD3 chimeric antibody was observed in culture supernatants, in order to increase amount of the antibody production using a DHFR gene amplification system, each of them was suspended in an IMDM-dFBS(10) medium (IMDM medium containing 10% dialyzed fetal bovine serum (hereinafter referred to as "dFBS"; manufactured by GIBCO BRL)) containing 0.5 mg/ml of G418 and 10 nM MTX to give a density of 1 to $2\times10^5$ cells/ml, and the suspension was dispensed in 0.5 ml into wells of a 24 well plate (manufactured by Iwaki Glass). Transformants showing 10 nM MTX resistance were induced by culturing at 37° C. for 1 to 2 weeks in a 5% $CO_2$ incubator. Regarding the transformants in wells in which their growth was observed, the MTX concentration was increased to 100 nM, and a transformant capable of growing in the IMDM-dFBS(10) medium containing 5 mg/ml of G418 and 100 nM MTX and of producing the anti-GD3 chimeric antibody in a large amount was finally obtained by the same method as described above. The obtained transformant was made into a single cell (cloning) by limiting dilution twice.

(3) Production of Producer Cell Using Mouse Myeloma NS0 Cell

After introducing 5 μg of the anti-GD3 chimeric antibody expression vector pChi641LHGM4 into $4\times10^6$ cells of mouse myeloma NS0 by electroporation (*Cytotechnology*, 3, 133 (1990)), the cells were suspended in 40 ml of EX-CELL302-FBS(10) (EX-CELL302 medium containing 10% FBS and 2 mM L-glutamine (hereinafter referred to as "L-Gln"; manufactured by GIBCO BRL)) and dispensed in 200 μl/well into a 96 well culture plate (manufactured by Sumitomo Bakelite). Twenty-four hours after culturing at 37° C. in a 5% $CO_2$ incubator, G418 was added to a concentration of 0.5 mg/ml, followed by culturing for 1 to 2 weeks. The culture supernatant was recovered from respective well in which colonies of transformants showing G418 resistance were formed and growth of colonies was observed, and the antigen binding activity of the anti-GD3 chimeric antibody in the supernatant was measured by the ELISA shown in the item 3 of Example 1.

Regarding the transformants in wells in which production of the anti-GD3 chimeric antibody was observed in culture supernatants, in order to increase amount of the antibody production using a DHFR gene amplification system, each of them was suspended in an EX-CELL302-dFBS(10) medium (EX-CELL302 medium containing 10% dFBS and 2 mM L-Gln) containing 0.5 mg/ml of G418 and 50 nM MTX to give a density of 1 to $2\times10^5$ cells/ml, and the suspension was dispensed in 2 ml into wells of a 24 well plate (manufactured by Greiner). Transformants showing 50 nM MTX resistance were induced by culturing at 37° C. for 1 to 2 weeks in a 5% $CO_2$ incubator. The antigen binding activity of the anti-GD3 chimeric antibody in culture supernatants in wells in which growth of transformants was observed was measured by the ELISA shown in the item 3 of Example 1. Regarding the transformants in wells in which production of the anti-GD3 chimeric antibody was observed in culture supernatants, the MTX concentration was increased to 100 nM and then to 200 nM, and a transformant capable of growing in the EX-CELL302-dFBS(10) medium containing 0.5 mg/ml of G418 and 200 nM MTX and of producing the anti-GD3 chimeric antibody in a large amount was finally obtained by the same method as described above. The obtained transformant was made into a single cell (cloning) by limiting dilution twice.

3. Measurement of Binding Activity of Antibody to GD3 (ELISA)

The binding activity of the antibody to GD3 was measured as described below.

In 2 ml of ethanol solution containing 10 μg of dipalmitoylphosphatidylcholine (manufactured by SIGMA) and 5 μg of cholesterol (manufactured by SIGMA), 4 nmol of GD3 was dissolved. Into each well of a 96 well plate for ELISA (manufactured by Greiner), 20 μl of the solution (40 pmol/well in final concentration) was dispensed, followed by air-drying, 1% bovine serum albumin (hereinafter referred to as "BSA"; manufactured by SIGMA)-containing PBS (hereinafter referred to as "1% BSA-PBS") was dispensed in 100 μl/well and then the reaction was carried out at room temperature for 1 hour for blocking remaining active groups. After discarding 1% BSA-PBS, a culture supernatant of a transformant or a diluted solution of a human chimeric antibody was dispensed in 50 μl/well to carry out the reaction at room temperature for 1 hour. After the reaction, each well was washed with 0.05% Tween 20 (manufactured by wako Pure Chemical Industries)-containing PBS (hereinafter referred to as "Tween-PBS"), a peroxidase-labeled goat anti-human IgG (H & L) antibody solution (manufactured by American Qualex) diluted 3,000 times with 1% BSA-PBS was dispensed in 50 μl/well as a secondary antibody solution, and then the reaction was carried out at room temperature for 1 hour. After the reaction and subsequent washing with Tween-PBS, ABTS substrate solution (a solution prepared by dissolving 0.55 g of 2,2'-azino-bis(3-ethylbenzothiazoline-6-sulfonic acid) ammonium salt in 1 liter of 0.1 M citrate buffer (pH 4.2) and adding 1 μl/ml of hydrogen peroxide to the solution just before use) was dispensed in 50 μl/well for color development, and then absorbance at 415 nm (hereinafter referred to as "OD415") was measured.

4. Purification of Anti-GD3 Chimeric Antibody (1) Culturing of YB2/0 Cell-derived Producer Cell and Purification of Antibody The anti-GD3 chimeric antibody-producing transformed cell clone obtained in the above item 2(1) of Example 1 was suspended in the Hybridoma-SFM medium containing 0.2% BSA, 200 nM MTX and 100 nM triiodothyronine (hereinafter referred to as "T3"; manufactured by SIGMA) to give a density of $3\times10^5$ cells/ml and cultured using a 2.0 liter capacity spinner bottle (manufactured by Iwaki Glass) under agitating at a rate of 50 rpm. Ten days after culturing at 37° C. in a temperature-controlling room, the culture supernatant was recovered. The anti-GD3 chimeric antibody was purified from the culture supernatant using a Prosep-A (manufactured by Bioprocessing) column in accordance with the manufacture's instructions. The purified anti-GD3 chimeric antibody was named YB2/0-GD3 chimeric antibody.

(2) Culturing of CHO/DG44 Cell-derived Producer Cell and Purification of Antibody The anti-GD3 chimeric antibody-producing transformed cell clone obtained in the above item 2(2) of Example 1 was suspended in the EX-CELL302 medium containing 3 mM L-Gln, 0.5% fatty acid concentrated solution (hereinafter referred to as "CDLC"; manufactured by GIBCO BRL) and 0.3% Pluronic F68 (hereinafter referred to as "PF68"; manufactured by GIBCO BRL) to give a density of $1\times10^6$ cells/ml, and the suspension was dispensed in 50 ml into 175 mm$^2$ flasks (manufactured by Greiner). Four days after culturing at 37° C. in a 5% $CO_2$ incubator, the culture supernatant was recovered. The anti-GD3 chimeric antibody was purified from the culture supernatant using a Prosep-A (manufactured by Bioprocessing) column in accordance with the manufacture's instructions. The purified anti-GD3 chimeric antibody was named CHO/DG44-GD3 chimeric antibody.

(3) Culturing of NS0 Cell-derived Producer Cell and Purification of Antibody

The anti-GD3 chimeric antibody-producing transformed cell clone obtained in the above item 2(3) of Example 1 was suspended in the EX-CELL302 medium containing 2 mM L-Gln, 0.5 mg/ml of G418, 200 nM MTX and 1% FBS, to give a density of $1\times10^6$ cells/ml, and the suspension was dispensed in 200 ml into 175 mm$^2$ flasks (manufactured by Greiner). Four days after culturing at 37° C. in a 5% $CO_2$ incubator, the culture supernatant was recovered. The anti-GD3 chimeric antibody was purified from the culture supernatant using a Prosep-A (manufactured by Bioprocessing) column in accordance with the manufacture's instructions. The purified anti-GD3 chimeric antibody was named NS0-GD3 chimeric antibody (302). Also, the transformed cell clone was suspended in the GIT medium containing 0.5 mg/ml of G418 and 200 nM MTX to give a density of $3\times10^5$ cells/ml, and the suspension was dispensed in 200 ml into 175 mm$^2$ flasks (manufactured by Greiner). Ten days after culturing at 37° C. in a 5% $CO_2$ incubator, the culture supernatant was recovered. The anti-GD3 chimeric antibody was purified from the culture supernatant using a Prosep-A (manufactured by Bioprocessing) column in accordance with the manufacture's instructions The purified anti-GD3 chimeric antibody was named NS0-GD3 chimeric antibody (GIT).

(4) Culturing of SP2/0 Cell-derived Producer Cell and Purification of Antibody

The anti-GD3 chimeric antibody-producing transformed cell clone described in Japanese Published Unexamined Patent Application No. 304989/93 was suspended in the GIT medium containing 0.5 mg/ml of G418 and 200 nM MTX to give a density of $3\times10^5$ cells/ml, and the suspension was dispensed in 200 ml into 175 mm$^2$ flasks (manufactured by Greiner). Eight days after culturing at 37° C. in a 5% $CO_2$ incubator, the culture supernatant was recovered. The anti-GD3 chimeric antibody was purified from the culture supernatant using a Prosep-A (manufactured by Bioprocessing) column in accordance with the manufacture's instructions. The purified anti-GD3 chimeric antibody was named SP2/0-GD3 chimeric antibody.

5. Analysis of the Purified Anti-GD3 Chimeric Antibodies

In accordance with a known method (*Nature*, 227, 680, 1970), 4 μg of each of the five anti-GD3 chimeric antibodies produced by and purified from respective animal cells, obtained in the above item 4 of Example 1, was subjected to SDS-PAGE to analyze the molecular weight and purification degree. The results are shown in FIG. 1 As shown in FIG. 1, a single band of about 150 kilodaltons (hereinafter referred to as "Kd") in molecular weight was found under non-reducing conditions, and two bands of about 50 Kd and about 25 Kd under reducing conditions, in each of the purified anti-GD3 chimeric antibodies. These molecular weights almost coincided with the molecular weights deduced from the cDNA nucleotide sequences of H chain and L chain of the antibody (H chain: about 49 Kd, L chain: about 23 Kd, whole molecule: about 144 Kd), and also coincided with the reports stating that the IgG antibody has a molecular weight of about 150 Kd under non-reducing conditions and is degraded into H chains having a molecular weight of about 50 kd and L chains having a molecular weight of about 25 Kd under reducing conditions due to cutting of the disulfide bond (hereinafter referred to as "S-S bond") in the molecule (*Antibodies: A Laboratory Manual*, Cold Spring Harbor Laboratory, Chapter 14, 1998; *Monoclonal Antibodies: Principles and Practice*, Academic Press Limited, 1996), so that it was confirmed that each anti-GD3 chimeric antibody was expressed and purified as an antibody molecule having the true structure.

EXAMPLE 2

Activity Evaluation of Anti-GD3 Chimeric Antibody:

1. Binding Activity of Anti-GD3 Chimeric Antibodies to GD3 (ELISA)

The activity of the five purified anti-GD3 chimeric antibodies obtained in the above item 4 of Example 1 to bind to GD3 (manufactured by Snow Brand Milk Products) was measured by the ELISA shown in the item 3 of Example 1. FIG. 2 shows a result of the examination of the binding activity measured by changing the concentration of the anti-GD3 chimeric antibody to be added. As shown in FIG. 2, the five anti-GD3 chimeric antibodies showed almost the same binding activity to GD3. This result shows that antigen binding activities of these antibodies are constant independently of the antibody producing animal cells and their culturing methods. Also, it was suggested from the comparison of the NS0-GD3 chimeric antibody (302) with the NS0-GD3 chimeric antibody (GIT) that the antigen binding activities are constant independently of the media used in the culturing.

2. In Vitro Cytotoxic Activity (ADCC Activity) of Anti-GD3 Chimeric Antibody

In order to evaluate in vitro cytotoxic activity of the five purified anti-GD3 chimeric antibodies obtained in the above item 4 of Example 1, the ADCC activity was measured in accordance with the following method.

(1) Preparation of Target Cell Solution

A human melanoma cultured cell line G-361 (ATCC CRL 1424) was cultured using the RPMI1640-FBS(10) medium to prepare $1 \times 10^6$ cells, and the cells were radioisotope-labeled by reacting them with 3.7 MBq equivalents of a radioactive substance $Na_2{}^{51}CrO_4$ at 37° C. for 1 hour. After the reaction, the cells were washed three times through their suspension in the RPMI1640-FBS(10) medium and centrifugation, re-suspended in the medium and then allowed to stand at 4° C. for 30 minutes in ice for spontaneous dissolution of the radioactive substance. After centrifugation, the precipitate was adjusted to $2 \times 10^5$ cells/ml by adding 5 ml of the RPMI1640-FBS(10) medium and used as the target cell solution.

(2) Preparation of Effector Cell Solution

From a healthy person, 50 ml of vein blood was collected, and gently mixed with 0.5 ml of heparin sodium (manufactured by Takeda Pharmaceutical). The mixture was centrifuged to isolate a mononuclear cell layer using Lymphoprep (manufactured by Nycomed Pharma AS) in accordance with the manufacture s instructions. After washing with the RPMI1640-FBS(10) medium by centrifugation three times, the resulting precipitate was re-suspended to give a density of $2 \times 10^6$ cells/ml using the medium and used as the effector cell solution.

(3) Measurement of ADCC Activity

Into each well of a 96 well U-shaped bottom plate (manufactured by Falcon), 50 µl of the target cell solution prepared in the above (1) ($1 \times 10^4$ cells/well) was dispensed. Next, 100 µl of the effector cell solution prepared in the above (2) was added thereto ($2 \times 10^5$ cells/well, the ratio of effector cells to target cells becomes 20:1). Subsequently, each of the anti-GD3 chimeric antibodies was added to give a final concentration from 0.0025 to 2.5 µg/ml, followed by reaction at 37° C. for 4 hours. After the reaction, the plate was centrifuged, and the amount of $^{51}Cr$ in the supernatant was measured using a γ-counter. The amount of spontaneously released $^{51}Cr$ was calculated by the same operation using only the medium instead of the effector cell solution and the antibody solution and measuring the amount of $^{51}Cr$ in the supernatant. The amount of total released $^{51}Cr$ was calculated by the same operation using only th medium instead of the antibody solution and adding 1 N hydrochloric acid instead of the effector cell solution, and measuring the amount of $^{51}Cr$ in the supernatant. The ADCC activity was calculated from the following equation.

$$ADCC \text{ activity } (\%) = \frac{{}^{51}Cr \text{ in sample supernatant} - \text{spontaneously released } {}^{51}Cr}{\text{total released } {}^{51}Cr - \text{spontaneously released } {}^{51}Cr} \times 100$$

Figure 3:
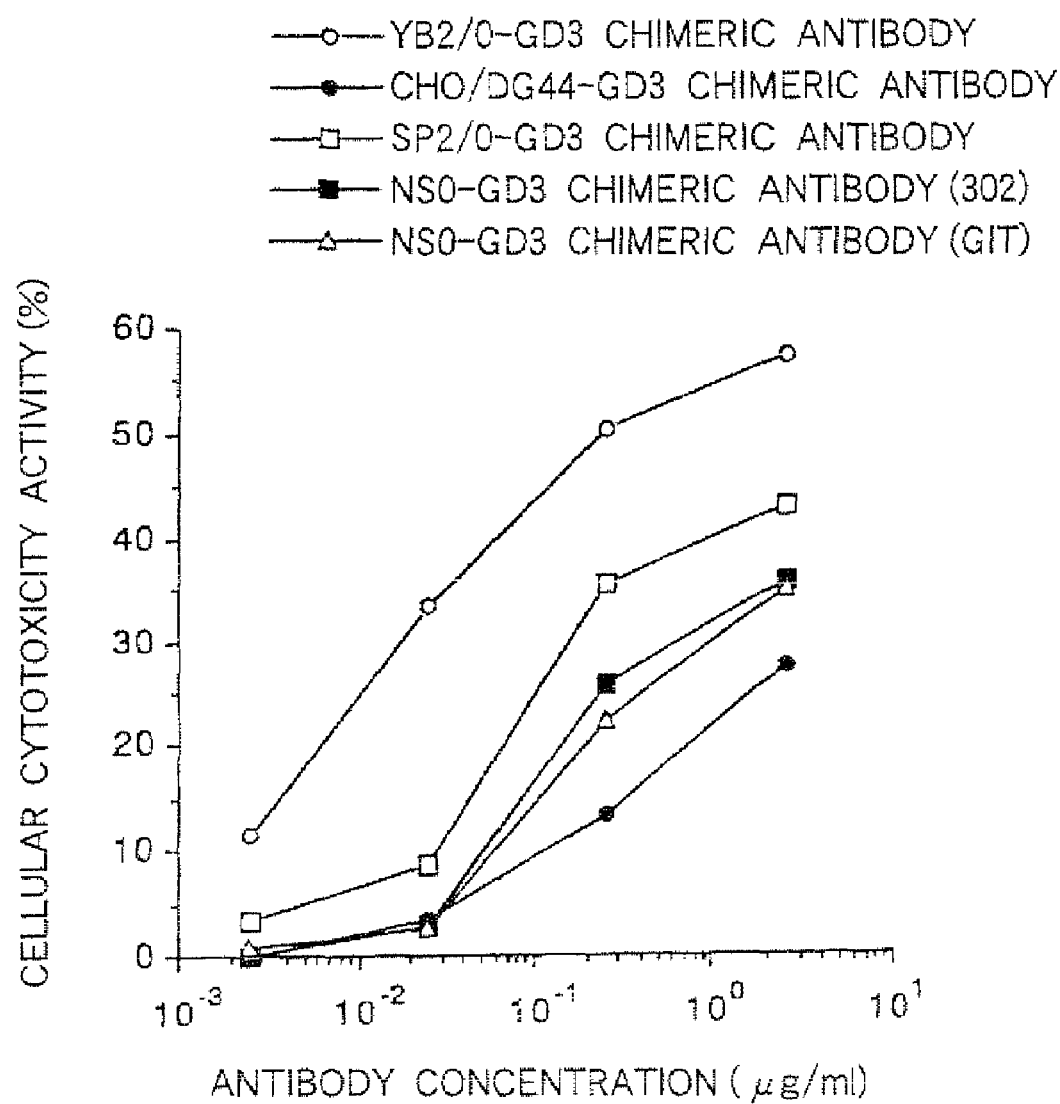
FIG. 3 is a graph showing the ADCC activity of five purified anti-GD3 chimeric antibodies for a human melanoma cell line G-361. The axis of ordinates and the axis of abscissas show the cytotoxic activity and the antibody concentration, respectively. Open circles, closed circles, open squares, closed squares, and open triangles show the activity of YB2/0-GD3 chimeric antibody, the activity of CHO/DG44-GD3 chimeric antibody, the activity of SP2/0-GD3 chimeric antibody, the activity of NS0-GD3 chimeric antibody (302), and the activity of NS0-GD3 chimeric antibody (GIT), respectively.

The results are shown in FIG. 3. As shown in FIG. 3, among the five anti-GD3 chimeric antibodies, the YB2/0-GD3 chimeric antibody showed the highest ADCC activity, followed by the SP2/0-GD3 chimeric antibody, NS0-GD3 chimeric antibody and CHO-GD3 chimeric antibody in that order. No difference in the ADCC activity was found between the NS0-GD3 chimeric antibody (302) and NS0-GD3 chimeric antibody (GIT) prepared using different media in the culturing. The above results show that the ADCC activity of antibodies greatly varies depending on the animal cells to be used in their production. As its mechanism, since their antigen binding activities were identical, it was considered that it is caused by a difference in the structure of the antibody Fc region.

EXAMPLE 3

Production of Anti-Human Interleukin 5 Receptor α Chain Human CDR-Grafted Antibody:

1. Production of Cells Stably Producing Anti-human Interleukin 5 Receptor α Chain Human CDR-Grafted Antibody (1) Production of Producer Cell Using Rat Myeloma YB2/0 Cell Using the anti-human interleukin 5 receptor α chain human CDR-grafted antibody (hereinafter referred to as "anti-hIL-5R α CDR-grafted antibody") expression vector, pKANTEX1259HV3LV0, described in WO 97/10354, cells capable of stably producing anti-hIL-5R α CDR-grafted antibody were prepared as described below.

After introducing 5 µg of the anti-hIL-5R α CDR-grafted antibody expression vector, pKANTEX1259HV3LV0, into $4 \times 10^5$ cells of rat myeloma YB2/0 by electroporation (*Cytotechnology*, 3, 133 (1990)), the cells were suspended in 40 ml of RPMI1640-FBS(10) and dispensed in 200 µl/well into a 96 well culture plate (manufactured by Sumitomo Bakelite). Twenty-four hours after culturing at 37° C. in a 5% $Co_2$ incubator, G418 was added to give a concentration of 0.5 mg/ml, followed by culturing for 1 to 2 weeks. The culture supernatant was recovered from respective well in which colonies of transformants showing G418 resistance were formed and growth of colonies was observed, and the antigen binding activity of the anti-hIL-5R α CDR-grafted antibody in the supernatant was measured by the ELISA shown in the item 2 of Example 3.

Regarding the transformants in wells in which production of the anti-hIL-5R α CDR-grafted antibody was observed in culture supernatants, in order to increase amount of the antibody production using a DHFR gene amplification system, each of the them was suspended in the RPMI1640-FBS(10)

medium containing 0.5 mg/ml of G418 and 50 nM MTX to give a density of 1 to $2\times10^5$ cells/ml, and the suspension was dispensed in 2 ml into wells of a 24 well plate (manufactured by Greiner). Transformants showing 50 nM MTX resistance were induced by culturing at 37° C. for 1 to 2 weeks in a 5% $CO_2$ incubator. The antigen binding activity of the anti-hIL-5R α CDR-grafted antibody in culture supernatants in wells in which growth of transformants was observed was measured by the ELISA shown in the item 2 of Example 3. Regarding the transformants in wells in which production of the anti-hIL-5R α CDR-grafted antibody was observed in culture supernatants, the MTX concentration was increased to 100 nM and then to 200 nM, and a transformant capable of growing in the RPMI1640FBS(10) medium containing 0.5 mg/ml of G418 and 200 nM MTX and of producing the anti-hIL-5R α CDR-grafted antibody in a large amount was finally obtained in the same manner as described above. The obtained transformant was made into a single cell (cloning) by limiting dilution twice. The obtained anti-hIL-5R α CDR-grafted antibody-producing transformed cell clone No. 3 has been deposited on Apr. 5, 1999 as FERM BP-6690 in National Institute of Bioscience and Human Technology, Agency of industrial Science and Technology (Higashi 1-1-3, Tsukuba, Ibaraki, Japan).

(2) Production of Producer Cell Using CHO/dhfr⁻ Cell

After introducing 4 μg of the anti-hIL-5R α CDR-grafted antibody expression vector, pKANTEX1259HV3LV0 described in WO 97/10354 into $1.6\times10^6$ cells of CHO/dhfr⁻ by electroporation (*Cytotechnology*, 3, 133 (1990)), the cells were suspended in 10 ml of IMDM-FBS(10) and dispensed in 200 μl/well into a 96 well culture plate (manufactured by Iwaki Glass). Twenty-four hours after culturing at 37° C. in a 5% $CO_2$ incubator G418 was added to give a concentration of 0.5 mg/ml, followed by culturing for 1 to 2 weeks. The culture supernatant was recovered from respective well in which colonies of transformants showing G418 resistance were formed and growth of colonies was observed, and the antigen binding activity of the anti-hIL5R α CDR-grafted antibody in the supernatant was measured by the ELISA shown in the item 2 of Example 3.

Regarding the transformants in wells in which production of the anti-hIL-5R α CDR-grafted antibody was observed in culture supernatants, in order to increase amount of the antibody production using a DHFR gene amplification system, each of the transformants was suspended in an IMDM-dFBS (10) medium containing 0.5 mg/ml of G418 and 10 nM MTX to give a density of 1 to $2\times10^5$ cells/ml, and the suspension was dispensed in 0.5 ml into wells of a 24 well plate (manufactured by Iwaki Class). Transformants showing 10 nM MTX resistance were induced by culturing at 37° C. for 1 to 2 weeks in a 5% $CO_2$ incubator. Regarding the transformants in wells in which their growth was observed, the MTX concentration was increased to 100 nM and then to 500 nM, and a transformant capable of growing in the IMDM-dFBS(10) medium containing 0.5 mg/ml of G418 and 500 nM MTX and of producing the anti-hIL-5R α CDR-grafted antibody in a large amount was finally obtained in the same manner as described above. The obtained transformant was made into a single cell (cloning) by limiting dilution twice.

(3) Production of Producer Cell Using Mouse Myeloma NS0 Cell

An anti-hIL-5R α CDR-grafted antibody expression vector was prepared in accordance with the method of Yarranton et al. (*BIO/TECHNOLOGY*, 10, 169 (1992)) and using the antibody H chain and L chain cDNA on the anti-hIL-5R α CDR-grafted antibody expression vector, pKANTEX1259HV3LV0, described in WO 97/10354, and NS0 cell was transformed to obtain a transformant capable of producing the anti-hIL-5R α CDR-grafted antibody in a large amount. The obtained transformant was made into a single cell (cloning) by limiting dilution twice.

2. Measurement of Binding Activity of Antibody to hIL-5R α (ELISA)

The binding activity of the antibody to hIL-5R α was measured as described below.

A solution was prepared by diluting the anti-hIL-5R α mouse antibody, KM1257, described in WO 97/10354 with PBS to give a concentration of 10 μg/ml, and 50 μl of the resulting solution was dispensed into each well of a 96 well plate for ELISA (manufactured by Greiner), followed by reaction at 4° C. for 20 hours, After the reaction, 1% BSA-PBS was dispensed in 100 μl/well, and then the reaction was carried out at room temperature for 1 hour for blocking remaining active groups. After discarding 1% BSA-PBS, a solution prepared by diluting the soluble hIL-5R α described in WO 97/10354 with 1% BSA-PBS to give a concentration of 0.5 μg/ml was dispensed in 50 μl/well, followed by reaction at 4° C. for 20 hours. After the reaction, each well was washed with Tween-PBS, culture supernatants of transformants or diluted solutions of a purified human CDR-grafted antibodies were dispensed in 50 μg/well to carry out the reaction at room temperature for 2 hours. After the reaction, each well was washed with Tween-PBS, a peroxidase-labeled goat anti-human IgG (H & L) antibody solution (manufactured by American Qualex) diluted 3,000 times with 1% BSA-PBS was dispensed in 50 μl/well as a secondary antibody solution, followed by reaction at room temperature for 1 hour. After the reaction and subsequent washing with Tween-PBS, ABTS substrate solution (a solution prepared by dissolving 0.55 g of 2,2'-azino-bis(3-ethylbenzothiazoline-6-sulfonic acid) ammonium salt in 1 liter of 0.1 M citrate buffer (pH 4.2) and adding 1 μl/ml of hydrogen peroxide to the solution just before use) was dispensed in 50 μl/well for color development, and then the absorbance at OD415 was measured.

3. Purification of Anti-hIL-5R α CDR-Grafted Antibody (1) Culturing of YB2/0 Cell-Derived Producer Cell and Purification of Antibody The anti-hIL-5R α CDR-grafted antibody-producing transformed cell clone obtained in the above item 1(1) of Example 3 was suspended in the GIT medium containing 0.5 mg/ml of G418 and 200 nM MTX to give a density of $3\times10^5$ cells/ml and dispensed in 200 ml into 175 mm² flasks (manufactured by Greiner). Eight days after culturing at 37° C. in a 5% $CO_2$ incubator, the culture supernatant was recovered. The anti-hIL-5R α CDR-grafted antibody was purified from the culture supernatant using ion exchange chromatography and a gel filtration method. The purified anti-hIL-5R α CDR-grafted antibody was named YB2/0-hIL-5RCDR antibody.

(2) Culturing of CHO/dhfr⁻ Cell-Derived Producer Cell and Purification of Antibody The anti-hIL-5R α CDR-grafted antibody-producing transformed cell clone obtained in the above item 1(2) of Example 3 was suspended in the EX-CELL302 medium containing 3 mM L-Gln, 0.5% CDLC and 0.3% PF68 to give a density of $3\times10^5$ cells/ml and cultured using a 4.0 liter capacity spinner bottle (manufactured by Iwaki Glass) under agitating at a rate of 100 rpm. Ten days after culturing at 37° C. in a temperature-controlling room, the culture supernatant was recovered. The anti-hIL-5R α CDR-grafted antibody was purified from the culture supernatant using ion exchange chromatography and a gel filtration method. The purified anti-hIL-5R α CDR-grafted antibody was named CHO/d-hIL-5RCDR antibody.

(3) Culturing of NS0 Cell-derived Producer Cell and Purification of Antibody

The anti-hIL-5R α CDR-grafted antibody-producing transformed cell clone obtained in the above item 1(3) of Example 3 was cultured in accordance with the method of Yarranton et al. (BIO/TECHNOLOGY, 10, 169 (1992)) and then a culture supernatant was recovered. The anti-hIL-5R α CDR-grafted antibody was purified from the culture supernatant using ion exchange chromatography and the gel filtration method. The purified anti-hIL-5R α CDR-grafted antibody was named NS0-hIL-5RCDR antibody.

4. Analysis of Purified Anti-hIL-5R α CDR-Grafted Antibodies

In accordance with a known method (*Nature*, 227, 680, (1970)), 4 µg of each of the three anti-hIL-5R α CDR-grafted antibodies produced by and purified from respective animal cells, obtained in the above item 3 of Example 3, was subjected to SDS-PAGE to analyze the molecular weight and purification degree. The results are shown in FIG. 4. As shown in FIG. 4, a single band of about 150 Kd in molecular weight was found under non-reducing conditions, and two bands of about 50 Kd and about 25 Kd under reducing conditions, in each of the purified anti-hIL-5R α CDR-grafted antibodies. These molecular weights almost coincided with the molecular weights deduced from the cDNA nucleotide sequences of H chain and L chain of the antibody (H chain: about 49 Kd, L chain: about 23 Kd, whole molecule: about 144 Kd), and also coincided with the reports stating that the IgG antibody has a molecular weight of about 150 Kd under non-reducing conditions and is degraded into H chains having a molecular weight of about 50 Kd and L chains having a molecular weight of about 25 Kd under reducing conditions due to cutting of the disulfide bond (hereinafter referred to as "S-S bond") in the molecule (*Antibodies: A Laboratory Manual*, Cold Spring Harbor Laboratory, Chapter 14, 1998; *Monoclonal Antibodies: Principles and Practice*, Academic Press Limited, 1996), so that it was confirmed that each anti-hIL-5R α CDR-grafted antibody was expressed and purified as an antibody molecule having the true structure.

EXAMPLE 4

Activity Evaluation of Anti-hIL-5R α CDR-Grafted Antibody:

1. Binding Activity of Anti-hIL-5R α CDR-Grafted Antibody to hIL-5R α (ELISA)

Figure 5:
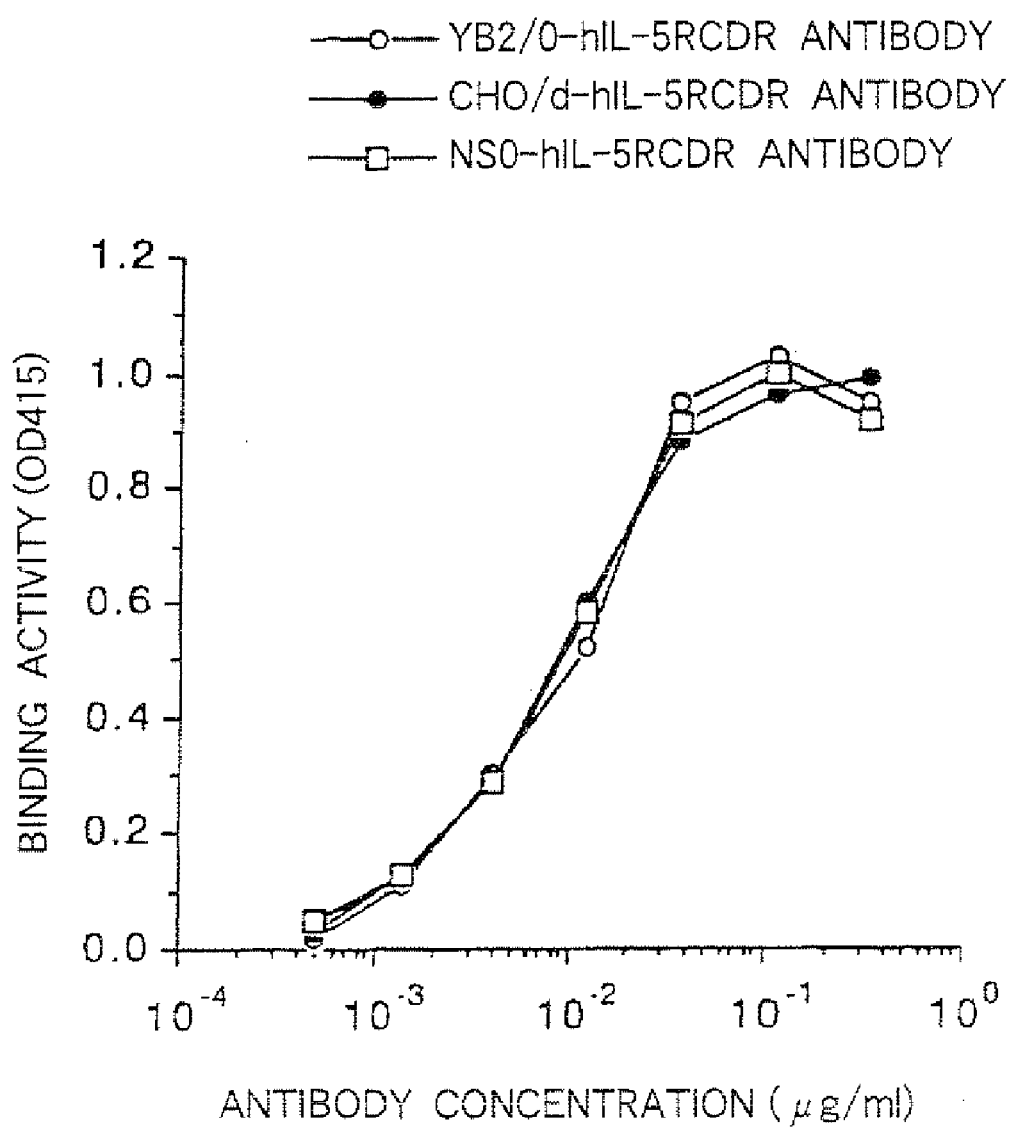
FIG. 5 is a graph showing the activity of three purified anti-hIL-5Rα CDR-grafted antibodies to bind to hIL-5Rα, measured by changing the antibody concentration. The axis of ordinates and the axis of abscissas show the binding activity with hIL-5Rα and the antibody concentration, respectively. Open circles, closed circles, and open squares show the activity of YB2/0-hIL-5RαCDR antibody, the activity of CHO/d-hIL-5RCDR antibody, and the activity of NS0-hIL-5RCDR antibody, respectively.

The activity of the three purified anti-hIL-5R α CDR-grafted antibodies obtained in the above item 2 of Example 3 to bind to hIL-5R α was measured by the ELISA shown in the item 2 of Example 3. FIG. 5 shows a result of the examination of the binding activity measured by changing concentration of the anti-hIL-5R α CDR-grafted antibody to be added. As shown in FIG. 5, the three anti-hIL-5R α CDR-grafted antibodies showed almost the same binding activity to hIL-5R α. This result shows that the antigen binding activities of these antibodies are constant independently of the antibody producing animal cells and their culturing methods, similar to the result of the item 1 of Example 2.

2. In Vitro Cytotoxic Activity (ADCC Activity) of Anti-hIL-5R α CDR-Grafted Antibody In order to evaluate in vitro cytotoxic activity of the three purified anti-hIL-5R α CDR-grafted antibodies obtained in the above item 3 of Example 3, the ADCC activity was measured in accordance with the following method.

(1) Preparation of Target Cell Solution

A mouse T cell line CTLL-2(h5R) expressing the hIL-5R α chain and β chain described in WO 97/10354 was cultured using the RPMI1640-FBS(10) medium to prepare a $1\times10^6$ cells/0.5 ml suspension, and the cells were radioisotope-labeled by reacting them with 3.7 MBq equivalents of a radioactive substance $Na_2{}^{51}CrO_4$ at 37° C. for 1.5 hours. After the reaction, the cells were washed three times through their suspension in the RPMI1640-FBS(10) medium and centrifugation, re-suspended in the medium and then allowed to stand at 4° C. for 30 minutes in ice for spontaneous dissolution of the radioactive substance. After centrifugation, the precipitate was adjusted to $2\times10^5$ cells/ml by adding 5 ml of the RPMI1640-FBS(10) medium and used as the target cell solution.

(2) Preparation of Effector Cell Solution

From a healthy person, 50 ml of vein blood was collected and gently mixed with 0.5 ml of heparin sodium (manufactured by Takeda Pharmaceutical). The mixture was centrifuged to separate a mononuclear cell layer using Polymorphprep (manufactured by Nycomed Pharma AS) and in accordance with the manufacture's instructions. After washing with the RPMI1640-FBS(10) medium by centrifugation three times, the resulting cells were re-suspended to give a density of $9\times10^6$ cells/ml using the medium and used as the effector cell solution.

(3) Measurement of ADCC Activity

Into each well of a 96 well U-shaped bottom plate (manufactured by Falcon), 50 µl of the target cell solution prepared in the above (1) ($1\times10^4$ cells/well) was dispensed. Next, 100 µl of the effector cell solution prepared in the above (2) was dispensed ($9\times10^5$ cells/well, the ratio of effector cells to target cells becomes 90:1). Subsequently, each of the anti-hIL-5R α CDR-grafted antibodies was added to give a final concentration from 0.001 to 0.1 µg/ml, followed by reaction at 37° C. for 4 hours. After the reaction, the plate was centrifuged, and the amount of $^{51}Cr$ in the supernatant was measured using a γ-counter. The amount of spontaneously released $^{51}Cr$ was calculated by the same operation using only the medium instead of the effector cell solution and the antibody solution and measuring the amount of $^{51}Cr$ in the supernatant. The amount of total released $^{51}Cr$ was calculated by the same operation using only the medium instead of the antibody solution and adding 1 N hydrochloric acid instead of the effector cell solution, and measuring the amount of $^{51}Cr$ in the supernatant.

The ADCC activity was calculated from the following equation.

$$ADCC \text{ activity } (\%) = \frac{{}^{51}Cr \text{ in sample supernatant} - \text{spontaneously released } {}^{51}Cr}{\text{total released } {}^{51}Cr - \text{spontaneously released } {}^{51}Cr} \times 100$$

Figure 6:
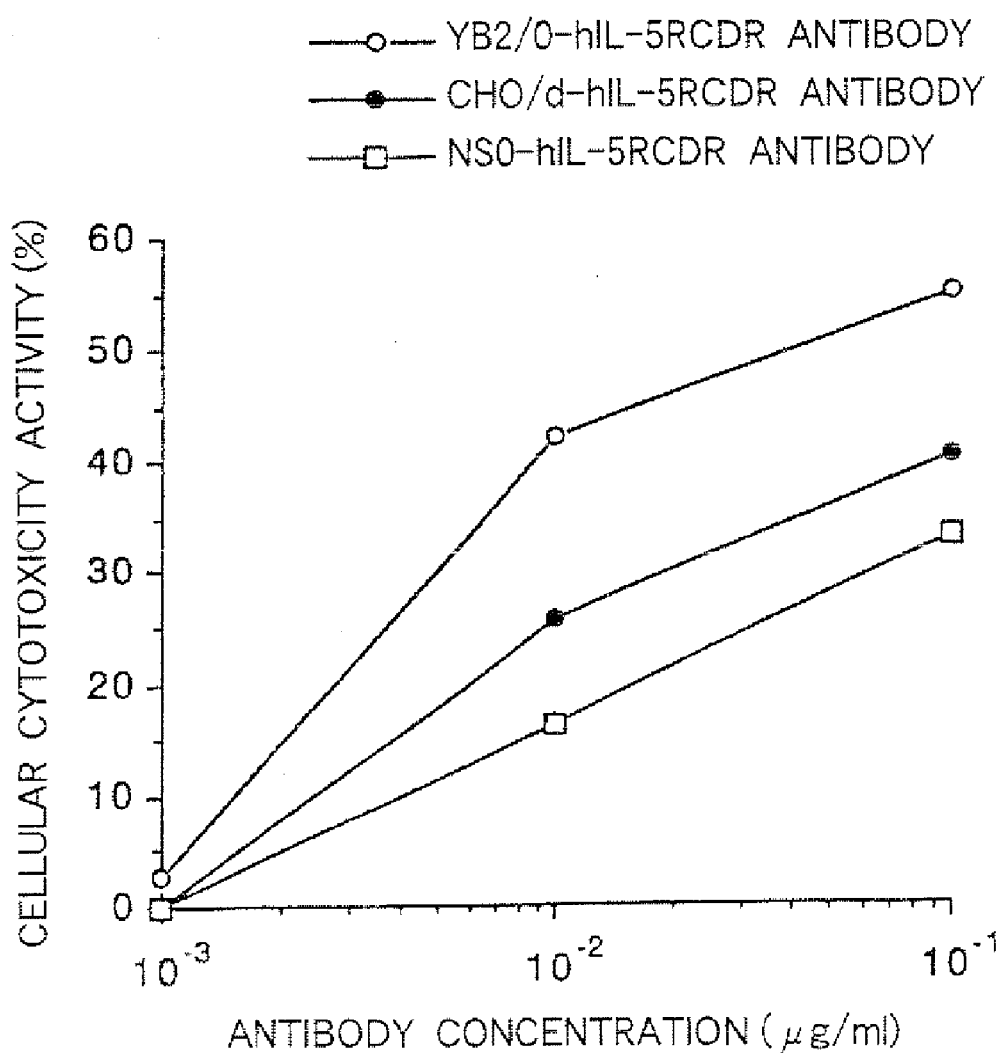
FIG. 6 is a graph showing the ADCC activity of three purified anti-hIL-5Rα CDR-grafted antibodies for an hIL-5R expressing mouse T cell line CTLL-2(h5R). The axis of ordinates and the axis of abscissas show the cytotoxic activity and the antibody concentration, respectively. Open circles, closed circles, and open squares show the activity of YB2/0-hIL- 5Rα CDR antibody, the activity of CHO/d-hIL-5RCDR antibody, and the activity of NS0-hIL-5RCDR antibody, respectively.

The results are shown in FIG. 6. As shown in FIG. 6, among the three anti-hIL-5R α CDR-grafted antibodies, the YB2/0-hIL-5RCDR antibody showed the highest ADCC activity, followed by the CHO/d-hIL-5RCDR antibody and the NS0-hIL-5RCDR antibody in this order. Similar to the result of the item 2 of Example 2, the above results show that the ADCC activity of antibodies greatly varies depending on the animal cells to be used in their production. In addition, since the antibodies produced by the YB2/0 cell showed the highest ADCC activity in both cases of the two humanized antibodies, it was revealed that an antibody having high ADCC activity can be produced by the use of the YB2/0 cell.

3. In Vivo Activity Evaluation of Anti-hIL-5R α CDR-Grafted Antibody

In order to evaluate in vivo activity of the three purified anti-hIL-5R α CDR-grafted antibodies obtained in the above item 3 of Example 3, the inhibition activity in an hIL-5-induced eosinophilia increasing model of *Macaca faseicularis* was examined in accordance with the following method.

Figure 7:
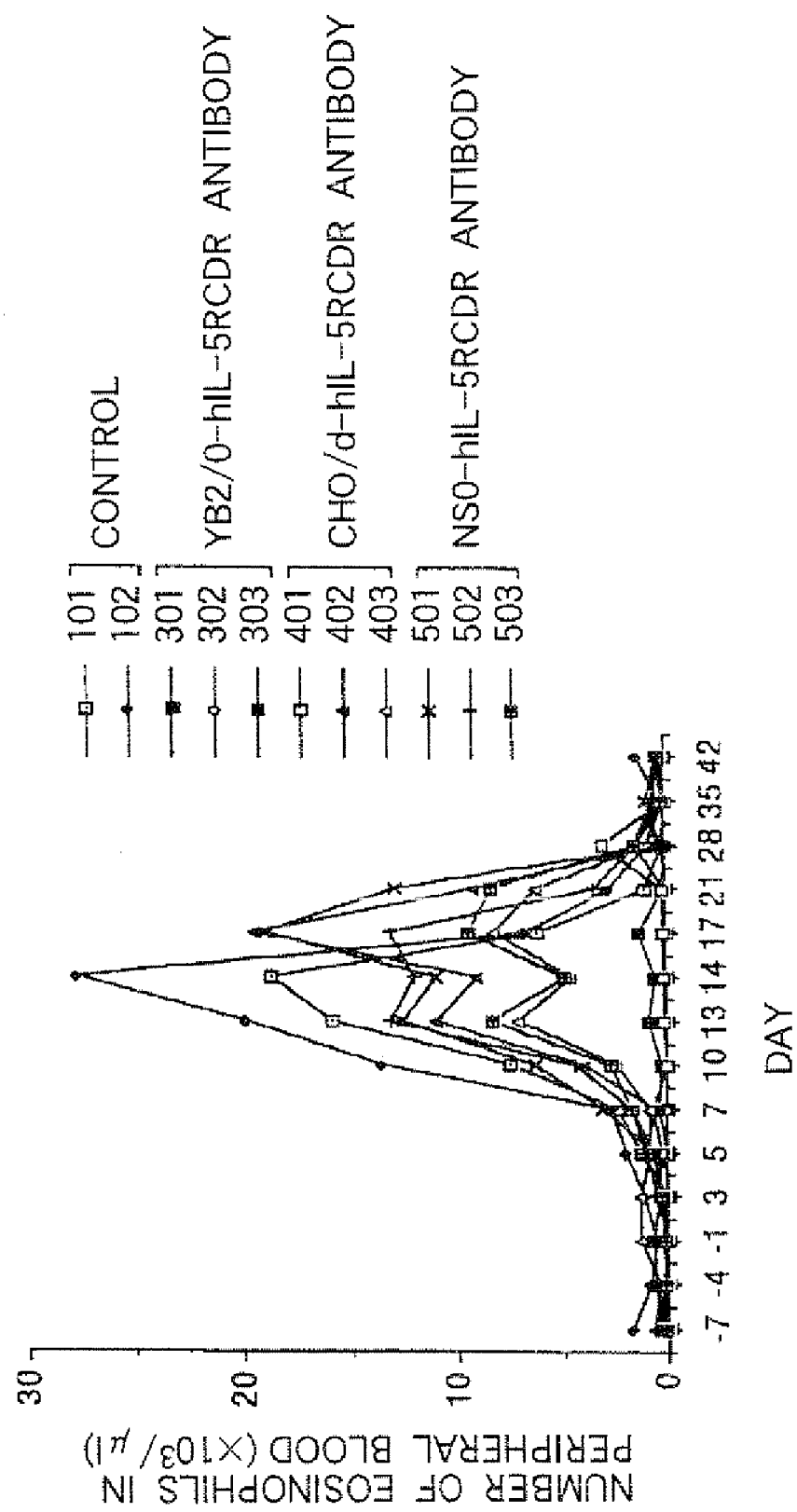
FIG. 7 is a graph showing the inhibition activity of three purified anti-hIL-5Rα CDR-grafted antibodies in an hIL-5-induced eosinophil increasing model of *Macaca faseicularis*. The axis of ordinates and the axis of abscissas show the number of eosinophils in peripheral blood and the number of days (the day of the commencement of antibody and hIL-5 administration was defined as 0 day). Results in the antibody non-administration group are shown by 101 and 102, results in the YB2/0-hIL-5RCDR antibody administered group are shown by 301, 302 and 303, results in the CHO/d-hIL-5RCDR antibody administered group are shown by 401, 402 and 403, and results in the NS0-hIL-5RCDR antibody administered group are shown by 501, 502 and 503.

The hIL-5 (preparation method is described in WO 97/10354) was administered to *Macaca faseicularis* under the dorsal skin at a dose of 1 μg/kg, starting on the first day and once a day for a total of 14 times. Each anti-hIL-5R α CDR-grafted antibody was intravenously administered at a dose of 0.3 mg/kg one hour before the hIL-5 administration on the day zero. An antibody-non-added group was used as the control. In the antibody-administered groups, three animals of *Macaca faseicularis* were used in each group (No. 301, No. 302, No. 303, No. 401, No. 402, No. 403, No. 501, No. 502 and No. 503), and two animals (No. 101 and No. 102) were used in the antibody-non-added group. Starting 7 days before commencement of the administration and until 42 days after the administration, about 1 ml of blood was periodically collected from a saphena or a femoral vein, and the number of eosinophils in 1 μl of peripheral blood was measured. The results are shown in FIG. 7. As shown in FIG. 7, increase in the blood eosinophil was completely inhibited in the group to which the YB2/0-hIL-5RCDR antibody was administered. On the other hand, complete inhibition activity was found in one animal in the group to which the CHO/d-hIL-5RCDR antibody was administered, but the inhibition activity was not sufficient in two animals. In the group to which NS0-hIL-5RCDR antibody was administered, complete inhibition activity was not found and its effect was not sufficient. The above results show that the in vivo activity of antibodies greatly varies depending on the animal cells to be used in their production. In addition, since a positive correlation was found between the degree of the in vivo activity of the anti-hIL-5R α CDR-grafted antibody and the degree of its ADCC activity described in the item 2 of Example 4, it was indicated that the degree of ADCC activity is markedly important for its activity expression.

Based on the above results, it is expected that an antibody having high ADCC activity is useful also in the clinical field for various diseases in human.

EXAMPLE 5

Analysis of ADCC Activity-Increasing Sugar Chain:

1. Preparation of 2-aminopyridine-labeled Sugar Chain (PA-Treated Sugar Chain)

The humanized antibody of the present invention was acid-hydrolyzed with hydrochloric acid to remove sialic acid. After hydrochloric acid was completely removed, the sugar chain was cut off from the protein by hydrazinolysis (*Method of Enzymology*, 83, 263, 1982). Hydrazine was removed, and N-acetylation was carried out by adding an ammonium acetate aqueous solution and acetic anhydride. After freeze-drying, fluorescence labeling with 2-aminopyridine was carried out (*J. Biochem.*, 95, 197 (1984), The fluorescence-labeled sugar chain (PA-treated sugar chain) was separated as an impurity using Surperdex Peptide HR 10/30 Column (manufactured by Pharmacia). The sugar chain fraction was dried using a centrifugal concentrator and used as a purified PA-treated sugar chain.

2. Reverse Phase HPLC Analysis of PA-Treated Sugar Chain of Purified Anti-hIL-5R α CDR-Grafted Antibody Using respective anti-hIL-5R α CDR-grafted antibody PA-treated sugar chains prepared in the above item 1 of Example 5, reverse phase HPLC analysis was carried out by CLC-ODS column (manufactured by Shimadzu). An excess amount of α-L-fucosidase (derived from bovine kidney, manufactured by SIGMA) was added to the PA-treated sugar chain for digestion (37° C., 15 hours), and then the products were analyzed by reverse phase HPLC (FIG. 8). Using PA-treated sugar chain standards manufactured by Takara Shuzo it was confirmed that the asparagine-linked sugar chain is eluted during a period of from 30 minutes to 80 minutes. The ratio of sugar chains whose reverse phase HPLC elution positions were shifted (sugar chains eluted during a period from 48 minutes to 78 minutes) by the α-L-fucosidase digestion was calculated. The results are shown in Table 1.

TABLE 1

| Antibody-producing cell | α-1,6-Fucose-linked sugar chain (%) |
|---|---|
| YB2/0 | 47 |
| NS0 | 73 |

About 47% of the anti-hIL-5RCDR-grafted antibody produced by the YB2/0 cell and about 73% of the anti-hIL-5RCDR-grafted antibody produced by the NS0 cell were sugar chains having α-1,6-fucose. Thus, sugar chains having no α-1,6-fucose were more frequent in the antibody produced by the YB2/0 cell in comparison with the antibody produced by the NS0 cell.

3. Analysis of Monosaccharide Composition of Purified Anti-hIL-5R α CDR-Grafted Antibody Sugar chains of anti-hIL-5R α CDR-grafted antibodies produced by the YB2/0 cell, NS0 cell and CHO/d cell were hydrolyzed into monosaccharides by acid hydrolysis with trifluoroacetic acid, and monosaccharide composition analysis was carried out using BioLC (manufactured by Dionex).

Among N-glycoside-linked sugar chains, there are 3 mannose units in one sugar chain in the complex type N-glycoside-linked sugar chain. A relative ratio of each monosaccharide obtained by calculating the number of mannose as 3 is shown in Table 2.

TABLE 2

| Antibody-producer cell | Fuc | GlcNAc | Gal | Man | ADCC activity (%)* |
|---|---|---|---|---|---|
| YB2/0 | 0.60 | 4.98 | 0.30 | 3.00 | 42.27 |
| NS0 | 1.06 | 3.94 | 0.66 | 3.00 | 16.22 |
| CHO/dhFr⁻ | 0.85 | 3.59 | 0.49 | 3.00 | 25.73 |
| | 0.91 | 3.80 | 0.27 | 3.00 | |

*Antibody concentration: 0.01 μg/ml

Since the relative ratios of fucose were in an order of YB2/0<CHO/d<NS0, the sugar chain produced in the antibody produced by YB2/0 cell showed the lowest fucose content as also shown in the present results.

EXAMPLE 6

Figure 9:
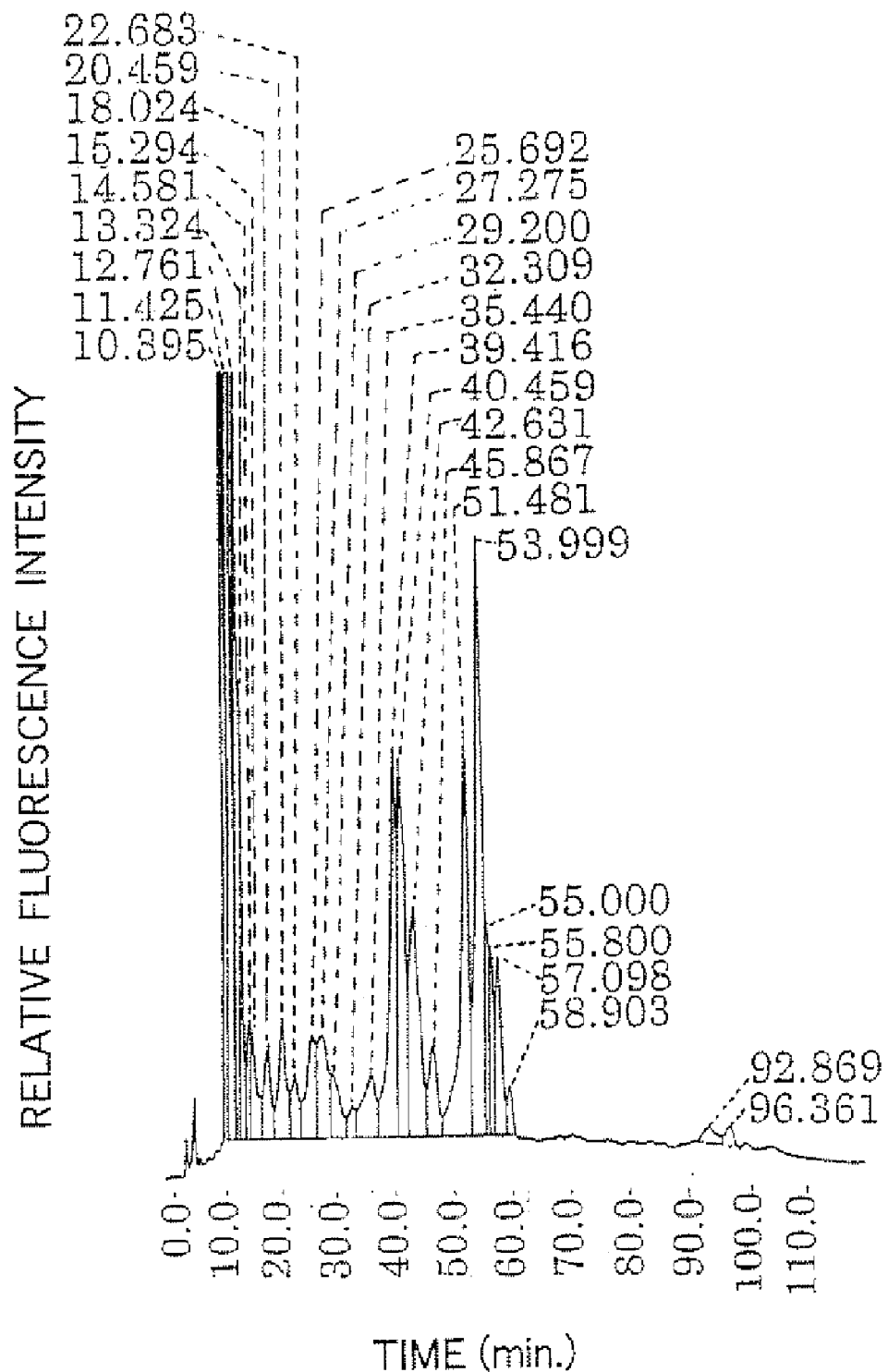
FIG. 9 is a graph showing an elution pattern obtained by preparing a PA-treated sugar chain from the purified anti-hIL-5Rα CDR-grafted antibody produced by CHO/d cell and analyzing it by reverse phase HPLC. The axis of ordinates and the axis of abscissas show the relative fluorescence intensity and the elution time, respectively.

Sugar Chain Analysis of Antibody Produced by CHO/dhfr⁻ Cell:

PA-treated sugar chains were prepared from purified anti-hIL-5R α CDR-grafted antibody produced by CHO/dhfr⁻ cell, and reverse phase HPLC analysis was carried out using CLC-ODS column (manufactured by Shimadzu) (FIG. 9). In FIG. 9, an elution time from 35 to 45 minutes corresponded to sugar chains having no fucose and an elution time from 45 to 60 minutes corresponded to sugar chains having fucose. Similar to the case of the antibody produced by mouse myeloma NS0 cell, the anti-hIL-5R α CDR-grafted antibody produced by CHO/dhfr⁻ cell had less fucose-free sugar chain content than the antibody produced by rat myeloma YB2/0 cell.

EXAMPLE 7

Figure 11:
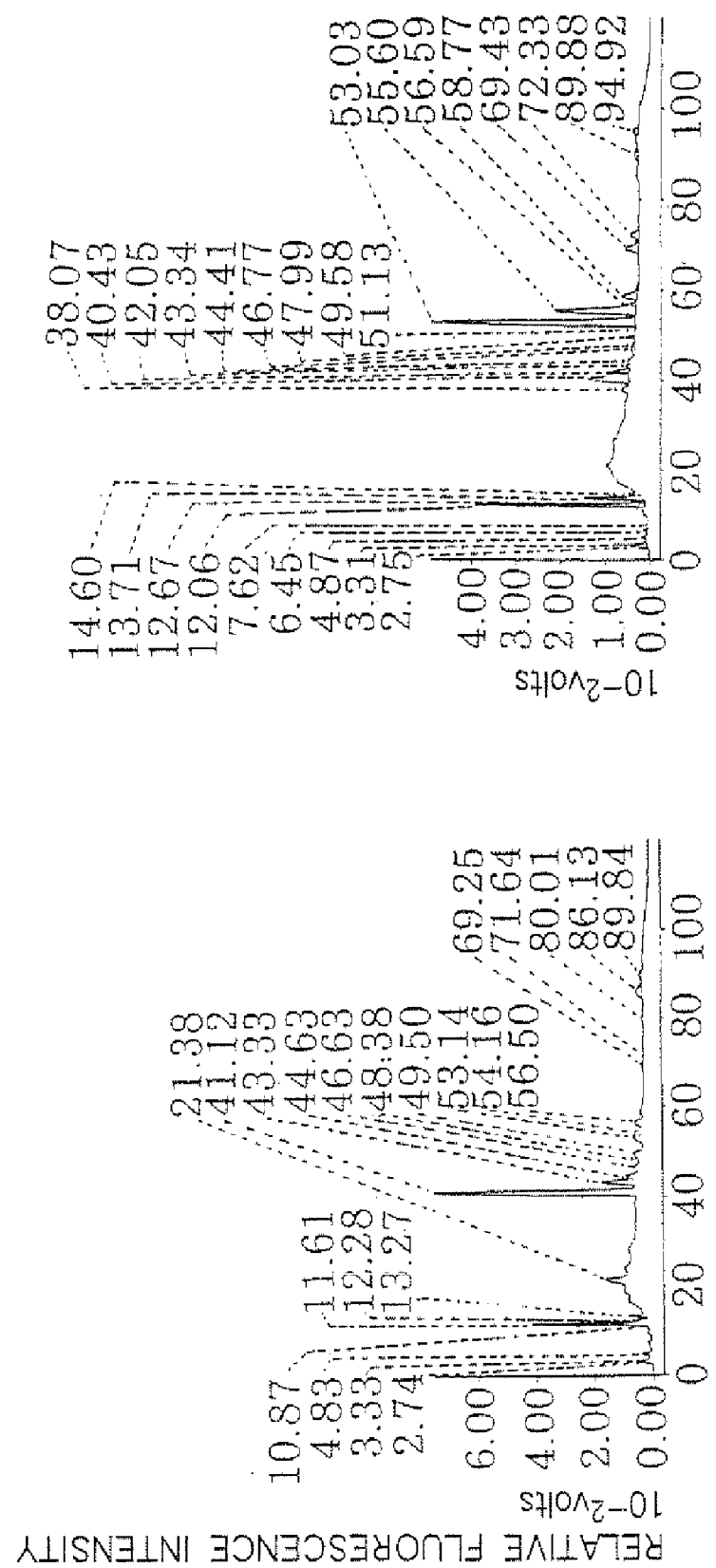
FIG. 11 is a graph showing elution patterns obtained by analyzing PA-treated sugar chains prepared from non-adsorbed fraction and a part of adsorbed fraction by a reverse HPLC. The left side drawing and the right side drawing show an elution pattern of the non-adsorbed fraction and an elution pattern of a part of the adsorbed fraction, respectively. The axis of ordinates and the axis of abscissas show the relative fluorescence strength and the elution time, respectively.

Separation of High ADCC Activity Antibody:

The anti-hIL-5R α CDR-grafted antibody produced by rat myeloma YB2/0 cell was separated using a lectin column which binds to sugar chains having fucose. HPLC was carried out using LC-6A manufactured by Shimadzu at a flow rate of 1 ml/min and at room temperature as the column temperature. After equilibration with 50 mM Tris-sulfate buffer (pH 7.3), the purified anti-hIL-5R α CDR-grafted antibody was injected and then eluted by a linear density gradient (60 minutes) of 0.2 M α-methylmannoside (manufactured by Nakalai Tesque). The anti-hIL-5R α CDR-grafted antibody was separated into non-adsorbed fraction and adsorbed fraction. When the non-adsorbed fraction and a portion of the adsorbed fraction were sampled and their binding activity to hIL-5R α was measured, they showed similar binding activity (FIG. 10, upper graph). When the ADCC activity was measured, the non-adsorbed fraction showed higher ADCC activity than that of the portion of adsorbed fraction (FIG. 10, lower graph). In addition, PA-treated sugar chains were prepared from the non-adsorbed fraction and a portion of the adsorbed fraction, and reverse HPLC analysis was carried out using CLC-ODS column (manufactured by Shimadzu) (FIG. 11). The non-adsorbed fraction was an antibody mainly having fucose-free sugar chains, and the portion of adsorbed fraction was an antibody mainly having fucose-containing sugar chains.

EXAMPLE 8

Determination of Transcription Product of α1,6-fucosyltransferase (FUT8) Gene in Host Cell Line:

(1) Preparation of Single-Stranded cDNA Derived from Various Cell Lines

Chinese hamster ovary-derived CHO/DG44 cell was suspended in the IMDM medium (manufactured by Life Technologies) supplemented with 10% FBS (manufactured by Life Technologies) and 1× concentration of HT supplement (manufactured by Life Technologies) and inoculated into a T75 flask for adhesion cell culture (manufactured by Greiner) at a density of 2×10⁵ cells/ml. Also, the rat myeloma-derived YB2/0 cell was suspended in the RPMI1640 medium (manufactured by Life Technologies) supplemented with 10% FBS (manufactured by Life Technologies) and 4 mM glutamine (manufactured by Life Technologies) and inoculated into a T75 flask for suspension cell culture (manufactured by Greiner) at a density of 2×10⁵ cells/ml. These cells were cultured at 37° C. in a 5% $CO_2$ incubator, and 1×10⁷ cells of each host cell were recovered on the 1st, 2nd, 3rd, 4th and 5th day to extract total RNA using RNAeasy (manufactured by QUIAGEN).

The total RNA was dissolved in 45 μl of sterile water, mixed with 0.5 U/μl of RQ1 RNase-Free DNase (manufactured by Promega) and 5 μl of attached 10× DNase buffer and 0.5 μl of RNasin Ribonuclease inhibitor (manufactured by Promega), followed by reaction at 37° C. for 30 minutes. After the reaction, the total RNA was again purified using RNAeasy (manufactured by QUIAGEN) and dissolved in 50 μl of sterile water.

According to SUPERSCRIPT™ Preamplification System for First Strand cDNA Synthesis (manufactured by Life Technology), 3 μg of the obtained total RNA each was subjected to a reverse transcription reaction in a 20 μl system using oligo (dT) as a primer to thereby synthesize cDNA. A solution of 1× concentration of the solution after the reverse transcription reaction was used for cloning of FUT8 and β-actin derived from each host cell, and a solution after the reverse transcription reaction further diluted 50 times with water was used for the determination of the transcription quantity of each gene using the competitive PCR, and each of the solutions was stored at −80° C. until use.

(2) Preparation of Respective cDNA Partial Fragments of Chinese Hamster FUT8 and Rat FUT8

Respective cDNA partial fragments of Chinese hamster FUT8 and of rat FUT8 were obtained as described below. First, primers (shown in SEQ ID NO:1 and SEQ ID NO:2) specific for nucleotide sequences common in a human FUT8 cDNA (*Journal of Biochemistry*, 121, 626 (1997)) and a swine FUT8 cDNA (*Journal of Biological Chemistry*, 271, 27810 (1996)) were designed.

Next, using a DNA polymerase ExTaq (manufactured by Takara Shuzo), 25 μl of a reaction solution constituted by ExTaq buffer (manufactured by Takara Shuzo), 0.2 mM dNTPs, 0.5 μM of each of the above specific primers (SEQ ID NO:1 and SEQ ID NO:2), and 1 μl of each of the cDNA derived from CHO cell and the cDNA derived from YB2/0 cell, each obtained on the 2nd day of culturing in (1), was prepared, and polymerase chain reaction (PCR) was carried out. The PCR was carried out under conditions in which, after heating at 94° C. for 1 minute, a cycle consisting of reactions at 94° C. for 30 seconds, 55° C. for 30 seconds and 72° C. for 2 minutes is repeated 30 cycles and then the reaction solution is heated at 72° C. for 10 minutes. Each specific amplified fragment of 979 bp obtained by the PCR was connected to a plasmid pCR2.1 using TOPO TA Cloning Kit (manufactured by Invitrogen) to obtain a plasmid containing respective cDNA partial fragment of Chinese hamster FUT8 or rat FUT8 (CHFT8-pCR2.1 or YBFT8-pCR2.1).

The nucleotide sequence of each cDNA obtained was determined using DNA Sequencer 377 (manufactured by Parkin Elmer) and BigDye Terminator Cycle Sequencing FS Ready Reaction Kit (manufactured by Parkin Elmer) to confirm that the obtained cDNAs encode open reading frame (ORF) partial sequences of Chinese hamster FUT8 and rat FUT8 (shown in SEQ ID NOs.3 and 4).

(3) Preparation of Chinese Hamster β-Actin and Rat β-Actin cDNA

Since it is considered that the β-actin gene is constantly transcribed in each cell and its transcription quantity is almost the same among cells, transcription quantity of the β-actin gene is determined as a standard of the efficiency of synthesis reaction of cDNA derived from respective cells.

Chinese hamster β-actin and rat β-actin were obtained by the following method. First, a forward primer (shown in SEQ ID NO:5) specific for a common sequence containing a translation initiation codon and reverse primers (shown in SEQ ID NO:6 and SEQ ID NO:7) specific for the respective sequence containing a translation termination codon were designed from a Chinese hamster β-actin genomic sequence (GenBank, U20114) and a rat β-actin genomic sequence (*Nucleic Acid Research*, 11, 1759 (1983)).

Next, using a DNA polymerase, KOD (manufactured by TOYOBO), 25 µl of a reaction solution constituted by KOD buffer #1 (manufactured by TOYOBO), 0.2 am dNTPs, 1 mM $MgCl_2$, 0.4 µM of each of the above gene specific primers (SEQ ID NO:5 and SEQ ID NO:6, or SEQ ID NO:5 and SEQ ID NO:7), 5% DMSO, and 1 µl of each of the cDNA derived from CHO cell and the cDNA derived from YB2/0 cell, each obtained on the 2nd day of culturing in (1), was prepared, and polymerase chain reaction (PCR) was carried out. The PCR was carried out under a condition in which, after heating at 94° C. for 4 minutes, a cycle consisting of reactions at 98° C. for 15 seconds, 65° C. for 2 seconds and 74° C. for 30 seconds is repeated 25 cycles, The 5'-terminal of each specific amplified fragment of 1,128 bp obtained by the PCR was phosphorylated using MEGALABEL (manufactured by Takara Shuzo) and then digested with a restriction enzyme, EcoRV, and the resulting fragment (2.9 Kb) was connected to pBluescript II (KS(+) (manufactured by Stratagene) using Ligation High (manufactured by TOYOBO) to obtain a plasmid containing an ORF full length of respective cDNA of Chinese hamster β-actin or rat β-actin (CHAc-pBS or YBAc-pBS).

The nucleotide sequence of the respective cDNA obtained was determined using DNA Sequencer 377 (manufactured by Parkin Elmer) and BigDye Terminator Cycle Sequencing FS Ready Reaction Kit (manufactured by Parkin Elmer) to confirm that they respectively encode ORF full length sequences of cDNA of Chinese hamster β-actin and rat β-actin.

(4) Preparation of Standard and Internal Sequence Control

In order to measure the quantity of mRNA transcription from the FUT8 gene in producer cells, a calibration curve was firstly prepared.

As the FUT8 standard to be used in the calibration curve, plasmids, CHFT8-pCR2.1 and YBFT8-pCR2.1, obtained in (2) by inserting respective cDNA partial fragments of Chinese hamster FUT8 or rat FUT8into pCR2.1 were digested with a restriction enzyme, EcoRI, and the resulting DNA fragments were used after making them into linear chains.

As the internal control to be used in the FUT8 determination, among CHFT8pCR2-1 and YBFT8-pCR2.1, CHFT8d-pCR2.1 and YBFT8d-pCR2.1 obtained by deleting 203 bp between ScaI-HindIII of internal nucleotide sequences of Chinese hamster FUT8or rat FUT8 were digested with the restriction enzyme, EcoRI, and the resulting DNA fragments were used after making them into linear chains.

As the standard of the quantity of mRNA transcribed from the β-actin gene in producer cells, plasmids CHAc-pBS and YBAc-pBS obtained in (3) by integrating the ORF full length of respective cDNAs of Chinese hamster β-actin and rat β-actin into pBluescript II KS(+) were respectively digested, the former with HindIII and PstI and the latter with HindIII and KpnI, and the resulting DNA fragments were used by making them into linear chains.

As the internal control for the determination of β-actin, among CHAc-pBS and YBAc-pBS, CHAcd-pBS and YBAcd-pBS obtained by deleting 180 bp between DraIII-DraIII of internal nucleotide sequences of Chinese hamster β-actin and rat β-actin were digested, the former with HindIII and PstI and the latter with HindIII and XpnI, and the resulting DNA fragments were used after making them into linear chains.

(5) Determination of Transcription Quantity by Competitive RT-PCR

First, a primer set (shown in SEQ ID NOs:8 and 9) common sequence-specific for internal sequences of ORF partial sequences of Chinese hamster FUT8 and rat FUT8 obtained in (2) was designed.

Next, PCR was carried out using a DNA polymerase ExTaq (manufactured by Takara Shuzo) in 20 µl in total volume of a reaction solution constituted by ExTaq buffer (manufactured by Takara Shuzo), 0.2 mM dNTPs, 0.5 µM of each of the above gene specific primers (SEQ ID NO:8 and SEQ ID NO:9), 5% DMSO, and 5 µl of a 50 times diluted solution of each of the cDNAs derived from respective host cell lines obtained in (1) and 5 µl (10 fg) of the plasmid for internal control. The PCR was carried out by heating at 94° C. for 3 minutes and then repeating 30 cycles using reactions at 94° C. for 1 minute, 60° C. for 1 minute and 72° C. for 1 minute as one cycle.

The β-actin transcription product was determined as described below. Primer sets gene-specific for internal sequences of the ORF full lengths of Chinese hamster β-actin and rat β-actin obtained in (3) (the former are shown in SEQ ID NO:10 and SEQ ID NO:11, and the latter in SEQ ID NO:12 and SEQ ID NO:13) were respectively designed.

Next, PCR was carried out using a DNA polymerase ExTaq (manufactured by Takara Shuzo) in 20 µl in total volume of a reaction solution constituted by ExTaq buffer (manufactured by Takara Shuzo), 0.2 mM dNTPs, 0.5 µM of the above gene specific primers (SEQ ID NO:10 and SEQ ID NO:11, or SEQ ID NO:12 and SEQ ID NO:13), 5% DMSO, and 5 µl of a 50 times diluted solution of each of the cDNAs derived from respective host cell lines obtained in (1) and 5 µl (1 pg) of the plasmid for internal control. The PCR was carried out by heating at 94° C. for 3 minutes and then repeating 17 cycles using reactions at 94° C. for 30 seconds, 65° C. for 1 minute and 72° C. for 2 minutes as one cycle.

TABLE 3

| Target gene | *Primer set | Size (bp) of PCR amplified product | |
|---|---|---|---|
| | | Target | Competitor |
| FUT8 | F:<br>5'-GTCCATGGTGATCCTGCAGTGTGG-3'<br>(SEQ ID NO:8)<br>R:<br>5'-CACCAATGATATCTCCAGGTTCC-3'<br>(SEQ ID NO:9) | 638 | 431 |

TABLE 3-continued

| Target gene | *Primer set | Size (bp) of PCR amplified product | |
|---|---|---|---|
| | | Target | Competitor |
| β-Actin (Chinese hamster) | F: 5'-GATATCGCTGCGCTCGTTGTCGAC-3' (SEQ ID NO:10)<br>R: 5'-CAGGAAGGAAGGCTGGAAAAGAGC-3' (SEQ ID NO:11) | 789 | 609 |
| β-Actin (rat) | F: 5'-GATATCGCTGCGCTCGTCGTCGAC-3' (SEQ ID NO:12)<br>R: 5'-CAGGAAGGAAGGCTGGAAGAGAGC-3' (SEQ ID NO:13) | 789 | 609 |

*F: forward primer, R: reverse primer

Determinative PCR was carried out using the primer sets shown in Table 3. As a result, the DNA fragment having the size shown in the target column of Table 3 was amplified from the respective gene transcription product and the corresponding standard, and the DNA fragment having the size shown in the competitor column of Table 3 was amplified from the corresponding internal control.

After 7 μl of the solution after PCR was subjected to 1.75% agarose gel electrophoresis, the gel was stained with SYBR Green I Nucleic Acid Gel Stain (manufactured by Molecular Probes). The quantity of the amplified DNA fragments was measured by calculating luminescence strength of each of the amplified DNA fragments using FluorImager SI (manufactured by Molecular Dynamics).

Furthermore, PCR was carried out by changing the amount of the standard plasmid prepared in (4) to 0.1 fg, 1 fg, 5 fg, 10 fg, 50 fg, 100 fg and 500 fg, instead of the cell-derived cDNA, and the amount of amplified products was determined. A calibration curve was prepared by plotting the measured values against the amounts of standard plasmid.

Using this calibration curve, the amount of cDNA of the gene of interest in each cell was calculated from the amount of the amplified product when the total cDNA derived from each cell was used as the template, and the amount was defined as the mRNA transcription quantity in each cell.

Figure 12:
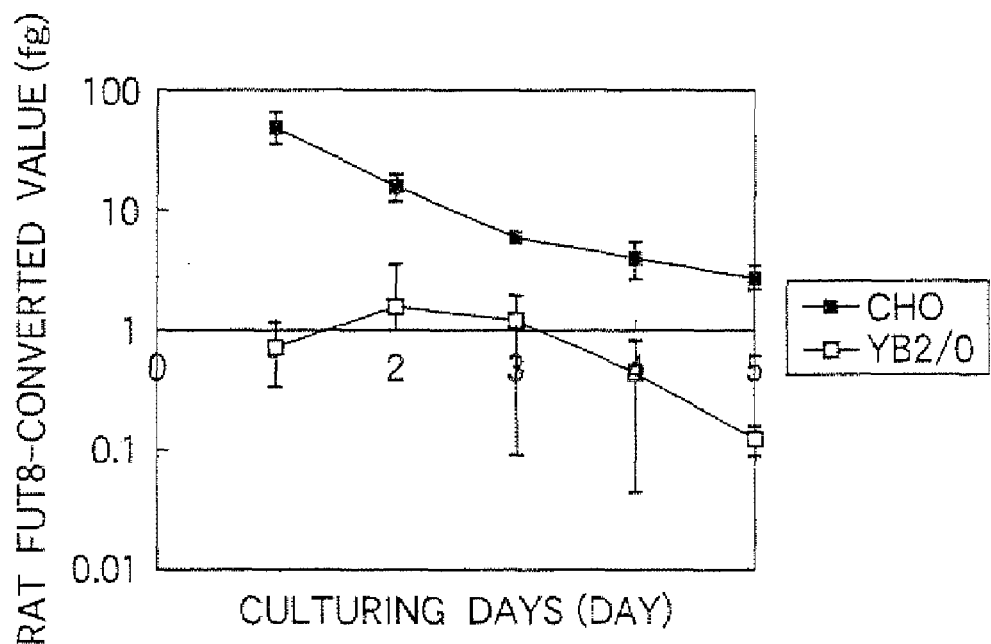
FIG. 12 is a graph showing the amount of FUT8 transcription product by respective host cell lines when a rat FUT8 sequence is used as the standard internal control. Closed circle and open circles show the result when CHO cell line was used and the result when YB2/0 cell line was used, as the host cell, respectively.

Amounts of the FUT8 transcription product in each host cell line in using rat FUT8 sequences as the standard and internal control are shown in FIG. 12. The CHO cell line showed a transcription quantity 10 times or more higher than that of the YB2/0 cell line throughout the culturing period. This tendency was found also when Chinese hamster FUT8 sequences were used as the standard and internal control.

Also, the FUT8 transcription quantity is shown in Table 4 as a relative value to the amount of β-actin transcription product.

TABLE 4

| | Culture days | | | | |
|---|---|---|---|---|---|
| Cell line | Day 1 | Day 2 | Day 3 | Day 4 | Day 5 |
| CHO | 2.0 | 0.90 | 0.57 | 0.52 | 0.54 |
| YB2/0 | 0.07 | 0.13 | 0.13 | 0.05 | 0.02 |

While the FUT8 transcription quantity of the YB2/0 cell line was about 0.1% β-actin, that of the CHO cell line was from 0.5 to 2%.

Based on the above results, it was shown that the amount of the FUT8 transcription product in the YB2/0 cell line was significantly smaller than that in the CHO cell line.

INDUSTRIAL APPLICABILITY

The present invention relates to a sugar chain which controls the activity of an immunologically functional molecule, such as an antibody, a protein, a peptide or the like, as well as an antibody, a protein or a peptide having the sugar chain. The present invention further relates to methods for the production of the sugar chain and an antibody, a protein or a peptide having the sugar chain, as well as a diagnostic agent, a preventive agent and a therapeutic agent which contain these products as an active ingredient.

We claim:

1. An antibody composition comprising antibody molecules, wherein 100% of the antibody molecules comprising a Fc region comprising complex N-glycoside-linked sugar chains bound to the Fc region through N-acetylglucosamines of the reducing terminal of the sugar chains do not contain sugar chains with a fucose bound to the N-acetylglucosamines, wherein said antibody molecules bind to CD52.

2. The antibody composition according to claim 1, wherein the antibody molecules are molecules selected from the group consisting of (a), (b) and (c);
   (a) human antibodies;
   (b) humanized antibodies;
   (c) antibody fragments.

3. The antibody composition according to claim 1, wherein the antibody molecules belong to an IgG class.

* * * * *